US012800578B2

(12) United States Patent
Hegab et al.

(10) Patent No.: US 12,800,578 B2
(45) Date of Patent: Nov. 17, 2026

(54) ENGINEERED BIOSENSORS IN AN ENCAPSULATED AND DEPLOYABLE SYSTEM (eBEADS) FOR ENVIRONMENTAL CHEMICAL DETECTION

(71) Applicant: The Johns Hopkins University, Baltimore, MD (US)

(72) Inventors: Rachel A. Hegab, Fulton, MD (US); Brooke M. Luisi, Silver Spring, MD (US); Julie E. Gleason, Catonsville, MD (US)

(73) Assignee: The Johns Hopkins University, Baltimore, MD (US)

( * ) Notice: Subject to any disclaimer, the term of this patent is extended or adjusted under 35 U.S.C. 154(b) by 943 days.

(21) Appl. No.: 18/053,501

(22) Filed: Nov. 8, 2022

(65) Prior Publication Data

US 2023/0204572 A1 Jun. 29, 2023

Related U.S. Application Data

(60) Provisional application No. 63/277,264, filed on Nov. 9, 2021.

(51) Int. Cl.

*G01N 33/543* (2006.01)
*G01N 33/544* (2006.01)
*G01N 33/84* (2006.01)

(52) U.S. Cl.

CPC ..... *G01N 33/54386* (2013.01); *G01N 33/544* (2013.01); *G01N 33/84* (2013.01); *G01N 2333/21* (2013.01); *G01N 2520/00* (2013.01)

(58) Field of Classification Search

None

See application file for complete search history.

(56) References Cited

PUBLICATIONS

Beggah et al, Mutant HbpR transcription activator isolation for 2-chlorobiphenyl via green fluorescent protein-based flow cytometry and cell sorting, Oct. 2007, Microbial Biotechnology, vol. 1, Issue 1, pp. 68-78 (Year: 2007).*

Wang et al Engineering modular and tunable genetic amplifiers for scaling transcriptional signals in cascaded gene networks, Jul. 2014, Nucleic Acids Research, vol. 42, Issue14, pp. 9484-9492 (Year: 2014).*

Tang et al, Tough Hydrogel-Based Biocontainment of Engineered Organisms for Continuous, Self-Powered Sensing and Computation, Feb. 2020, bioRxiv. (Year: 2020).*

Kamaci et al, Polyurethane-based hydrogels for controlled drug delivery applications, Jan. 2020, European Polymer Journal, vol. 123 (Year: 2020).*

Liu et al, 3D printed hydrogel/PCL core/shell fiber scaffolds with NIR-triggered drug release for cancer therapy and wound healing, Sep. 2021, Acta Biomaterialia, vol. 131, pp. 314-325 (Year: 2021).*

Bradley et al, Designer cell signal processing circuits for biotechnology, New Biotechnology, vol. 32, Issue 6, pp. 635-643 (Year: 2015).*

O'Malley, "Clinical evaluation of pesticide exposure and poisonings," The Lancet, Apr. 1997, vol. 349, 1161-66.

Yang et al., "Determination of ortho-Phenylphenol Residues in Lemon Rind by High-Performance Liquid Chromatography with Electrochemical Detection Using a Microbore Column," Analytical Sciences, Jan. 2004, vol. 20.

Mishra et al.,"Wearable Flexible and Stretchable Glove Biosensor for On-Site Detection of Organophosphorus Chemical Threats," American Chemical Society Sensors, Mar. 2017, vol. 2, 553-561.

Daunert et al., "Genetically Engineered Whole-Cell Sensing Systems: Coupling Biological Recognition with Reporter Genes," Chemical Reviews, Jun. 2000, vol. 100, 2705-2738.

Adeniran et al., "Yeast-Based Biosensors: Design and Applications," FEMS Yeast Research, Feb. 2015, vol. 15, Issue 1, 1-15.

Kim et al., "Wearable Biosensors for Healthcare Monitoring," Nature Biotechnology, Feb. 2019, vol. 37 (4), 389-406.

Choi, J. R., "Development of Point-of-Care Biosensors for COVID-19," Frontiers in Chemistry, May 2020, vol. 8, Article 517.

Gui et al., "The Application of Whole Cell-Based Biosensors for Use in Environmental Analysis and in Medical Diagnostics," Sensors (Switzerland), Jul. 2017,vol. 17, 1623.

Patel et al., "Structure Prediction and Molecular Docking Studies of Aromatic Hydrocarbon Sensing Proteins TbuT, HbpR and PhnR to Detect Priority Pollutants," Journal of Environmental Science and Health, Part A, 2020, vol. 55, No. 2, 126-141.

Sánchez et al., "The Integration of Whole-Cell Biosensors for the Field-Ready Electrochemical Detection of Arsenic," Journal of the Electrochemical Society, Jun. 2021, 168, 067508.

Wei et al., "Specific Detection of Bioavailable Phenanthrene and Mercury by Bacterium Reporters in the Red Soil," International Journal of Environmental Science and Technology, 2014, 11:685-694.

Peltola et al., "Lead and Cu in Contaminated Urban Soils: Extraction with Chemical Reagents and Bioluminescent Bacteria and Yeast," Science of the Total Environment, 2005, 350 (1-3), 194-203.

Whangsuk et al., "Specific Detection of the Pesticide Chlorpyrifos by a Sensitive Genetic-Based Whole Cell Biosensor," Analytical Biochemistry, 2016, 493, 11-13.

Khatun et al., "Bacterial Consortium-Based Sensing System for Detecting Organophosphorus Pesticides," Analytical Chemistry, 2018, vol. 90, No. 17, 10577-10584.

(Continued)

*Primary Examiner* — Allison M Fox
*Assistant Examiner* — Marisol Ann O'Neill
(74) *Attorney, Agent, or Firm* — Todd Richard Farnsworth

(57) ABSTRACT

Provided is a whole-cell biosensor system with robust biocontainment for field deployment and a strong visual reporter for readouts in the deployed environment. The engineered biosensors in an encapsulated and deployable system (eBEADS) demonstrate a portable, no power living sensor for detection of environmental pollutants, e.g., 2-phenylphenol (2-PP). The whole-cell biosensor system uses bacteria engineered to detect an analyte and generate a visual colorimetric output upon being contacted with the analyte. Advantageously, the analyte is detectable with the naked eye and the whole-cell biosensor system enables analyte detection without electronics.

16 Claims, 15 Drawing Sheets

Specification includes a Sequence Listing.

(56) References Cited

PUBLICATIONS

Wick et al., "Source and Chemodynamic Behavior of Diphenyl Sulfone and Ortho- and Para-Hydroxybiphenyl in a Small Lake Receiving Discharges from an Adjacent Superfund Site," Environmental Science & Technology, 1998, vol. 32, No. 9, 1319-1328.
Ye et al., "Automated On-Line Column-Switching HPLC-MS/MS Method with Peak Focusing for the Determination of Nine Environmental Phenols in Urine," Analytical Chemistry, Aug. 2005, vol. 77, No. 16, 5407-5413.
Thompson,R. D., "Determination of Phenolic Disinfectant Agents in Commercial Formulations by Liquid Chromatography," Journal of Aoac International vol. 84, No. 3, May 2001, 815-822.
Coelhan et al., "Determination and Levels of the Biocide Ortho-Phenylphenol in Canned Beers from Different Countries," Journal of Agricultural and Food Chemistry, Jul. 2006, vol. 54, No. 16, 5731-5735.
Jaspers et al., "HbpR, a New Member of the Xylr/DmpR Subclass within the NtrC Family of Bacterial Transcriptional Activators, Regulates Expression of 2-Hydroxybiphenyl Metabolism in Pseudomonas Azelaica HBP1," Journal of Bacteriology, Jan. 2000, vol. 182, No. 2, 405-417.
Turner et al., "Hydroxylated Polychlorinated Biphenyl Detection Based on a Genetically Engineered Bioluminescent Whole-Cell Sensing System," Analytical Chemistry, Aug. 2007, vol. 79, No. 15, 5740-5745.
Zhang et al., "Modular Tuning Engineering and Versatile Applications of Genetically Encoded Biosensors," Critical Reviews in Biotechnology, 2022, vol. 42, No. 7, 1010-1027.
Wang et al., "Engineering Modular and Orthogonal Genetic Logic Gates for Robust Digital-like Synthetic Biology," Nature Communications, 2:508 doi: 10.1038/ncomms1516 (2011).
Ortiz-Martin et al., "Negative Regulation of the Hrp Type III Secretion System in Pseudomonas Syringae Pv. Phaseolicola," Molecular Plant-Microbe Interactions, 2010, vol. 23, No. 5, 682-701.
Nistala et al., "A Modular Positive Feedback-Based Gene Amplifier," Journal of Biological Engineering, Feb. 2010, 4:4.
Wook Lee et al., "Next-Generation Biocontainment Systems for Engineered Organisms," Nature Chemical Biology, Jun. 2018, vol. 14, 530-537.
Tang et al., "Hydrogel-Based Biocontainment of Bacteria for Continuous Sensing and Computation," Nature Chemical Biology, Apr. 2021, vol. 17, 724-731.
Liu et al., "Stretchable Living Materials and Devices with Hydrogel-Elastomer Hybrids Hosting Programmed Cells," Proceedings of the National Academy of Sciences, Feb. 2017, vol. 114, No. 9, 2200-2205.
Lee et al., "Implementation of Combinatorial Genetic and Microenvironmental Engineering to Microbial-Based Field-Deployable Microbead Biosensors for Highly Sensitive and Remote Chemical Detection," American Chemical Society Senors, Sep. 2019, vol. 4, 2716-2723.
Karsi et al., "Broad Host Range Fluorescence and Bioluminescence Expression Vectors for Gram-Negative Bacteria," PLASMID, May 2007, vol. 57, Issue 3, 286-295.
De Lorenzo et al., "Analysis of Pseudomonas Gene Products Using LacP/Ptrp-Lac Plasmids and Transposons That Confer Conditional Phenotypes," Gene Jan. 1993, vol. 123, Issue 1, 17-24.
Zou et al., "A Sodium Alginate-Based Sustained-Release IPN Hydrogel and Its Applications," The Royal Society of Chemistry Advances, Oct. 2020, 10, 39722-39730.
Rana et al., "Cell-Laden Alginate/Polyacrylamide Beads as Carriers for Stem Cell Delivery: Preparation and Characterization," The Royal Society of Chemistry Advances, Feb. 2016, 6, 20475-20484.
Sun et al., "Highly Stretchable and Tough Hydrogels," Nature, Sep. 2012, vol. 489, 133-136.
Darnell et al., "Performance and Biocompatibility of Extremely Tough Alginate/Polyacrylamide Hydrogels," Biomaterials, Jul. 2013, vol. 34, Issue 33, 8042-8048.
Hutcheson et al., "Enhancer-Binding Proteins HrpR and HrpS Interact To Regulate Hrp-Encoded Type III Protein Secretion in Pseudomonas Syringae Strains," Journal of Bacteriology, Oct. 2001, vol. 183, No. 19, 5589-5598.
Liljeruhm et al., "Engineering a Palette of Eukaryotic Chromoproteins for Bacterial Synthetic Biology," Journal of Biological Engineering, May 2018, 12:8, 1-10.
Moraski et al., "Microbial Whole-Cell Biosensors: Current Applications, Challenges, and Future Perspectives," Biosensors and Bioelectronics, Nov. 2021, vol. 191, 113359.
Jayaraman et al., "Repurposing a Two-Component System-Based Biosensor for the Killing of Vibrio Cholerae," American Chemical Society Synthetic Biology, Jul. 2017, vol. 6, 1403-1415.
Borrero et al., "Modified Lactic Acid Bacteria Detect and Inhibit Multiresistant Enterococci," American Chemical Society Synthetic Biology, Mar. 2015, vol. 4, 299-306.
Lubkowicz et al., "Reprogramming Probiotic Lactobacillus Reuteri as a Biosensor for *Staphylococcus aureus* Derived AIP-I Detection," American Chemical Society Synthetic Biology, May 2018, vol. 7, 1229-1237.
Wu et al., "A Whole-Cell Biosensor for Point-of-Care Detection of Waterborne Bacterial Pathogens," American Chemical Society Synthetic Biology, Jan. 2021, vol. 10, 333-344.
Subraveti et al., "A Simple Way to Synthesize a Protective 'Skin' around Any Hydrogel," American Chemical Society Applied Materials & Interfaces, Jul. 2021, vol. 13, 37645-37654.
Yuk et al., "Skin-Inspired Hydrogel-Elastomer Hybrids with Robust Interfaces and Functional Microstructures," Nature Communications, 7:12028 doi: 10.1038/ncomms12028 (2016).
Kakizuka et al., "An Improved Fluorescent Protein-Based Expression Reporter System That Utilizes Bioluminescence Resonance Energy Transfer and Peptide-Assisted Complementation," The Royal Society of Chemistry, Chemical Communications Journal, Feb. 2020, vol. 56, 3625-3628.
United States Environmental Protection Agency, "Reregistration Eligibility Decision for 2-Phenylphenol and Salts (Orthophenylphenol or OPP)," Office of Prevention, Pesticides and Toxic Substances, Jul. 2006.
Zubiate et al., "Fiber-Based Early Diagnosis of Venous Thromboembolic Disease by Label-Free D-Dimer Detection," Biosensors and Bioelectronics: X (2019) 100026.
Chiavaioli et al., "Detection by Nanocoated Fiber Label-Free Biosensors," American Chemical Society Sensors, May 2018, vol. 3, 936-943.
Hooshangi, Ultrasensitivity and noise propagation in a synthetic transcriptional cascade, PNAS, Mar. 8, 2005, pp. 3581-3586, vol. 102 No. 10, The National Academy of Sciences of the USA.

* cited by examiner

FIG. 2B
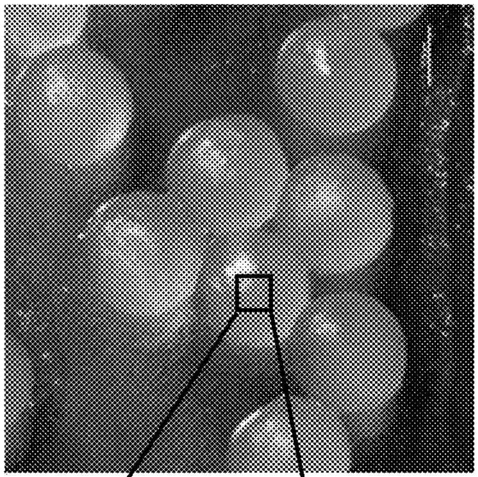
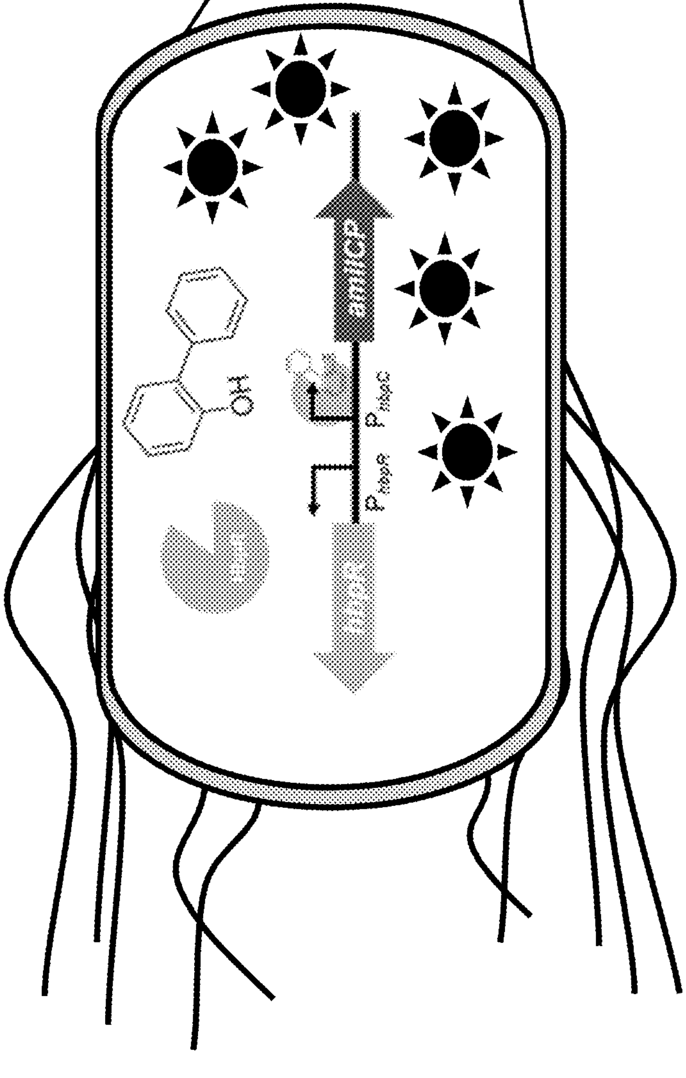
FIG. 2A

ENGINEERED BIOSENSORS IN AN ENCAPSULATED AND DEPLOYABLE SYSTEM (eBEADS) FOR ENVIRONMENTAL CHEMICAL DETECTION

CROSS REFERENCE TO RELATED APPLICATIONS

This application claims the benefit of U.S. Provisional Application No. 63/277,264, filed Nov. 9, 2021, the contents of which are incorporated by reference herein in its entirety.

REFERENCE TO SEQUENCE LISTING SUBMITTED ELECTRONICALLY

The content of the electronically submitted sequence listing in ASCII text file (Name 4831.014STR0_Seqlisting_ST26; Size: 103,411 bytes; and Date of Creation: Nov. 8, 2022) filed with the application is incorporated herein by reference in its entirety.

BACKGROUND

The long-term exposure of low levels of pollutants and chemicals in an environment can present a hazard to human and aquatic health. Early indications of exposure may help mitigate these long-term adverse effects (O'Malley, M., Lancet 1997, 349 (9059), 1161-1166; Zubiate, P. et al., Biosens. Bioelectron. X 2019, 2, 100026; Chiavaioli, F. et al., ACS Sensors 2018, 3 (5), 936-943). Chemical detection methods lack the sensitivity and specificity of mass spectrometry; however, mass spectrometry methods are high cost and lack the portability of chemical detection (Yang, L. et al., Anal. Sci. 2004, 20 (1), 199-203; Mishra, R. K. et al., ACS Sensors 2017, 2 (4), 553-561). Microbes have naturally evolved receptors to detect and respond to known human health hazards, like phenanthrene, lead, copper, and organophosphate pesticides (Wei H. et al., Int. J. Environ. Sci. Technol. 2014, 11 (3), 685-694; Peltola, P. et al., Sci. Total Environ. 2005, 350 (1-3), 194-203; Whangsuk, W. et al., Anal. Biochem. 2016, 493, 11-13; Khatun, M. A., et al., Anal. Chem. 2018, 90 (17), 10577-10584).

One environmental pollutant for which there is currently not a zero-power monitoring technology is the fungicide, 2-phenylphenol (2-PP). This molecule is used to preserve citrus fruits and vegetables and is used in the manufacturing of other fungicides, dyes, resins, and rubber chemicals (Yang, L., et al. Anal. Sci. 2004, 20 (1), 199-203; Wick, L. Y. et al. Environ. Sci. Technol. 1998, 32 (9), 1319-1328). According to the EPA, regulatory tolerance levels for 2-PP are as low as 10 ppm for certain fruits and the $LC_{50}$ for some aquatic organisms can be as low as 0.32 mg/L (EPA. Reregistration Eligibility Decision for 2-Phenylphenol and Salts (Orthophenylphenol or OPP); 2006). While 2-PP has been found in urine, its toxicity to humans is unknown, but it is toxic to aquatic life (Ye, X. et al., Anal. Chem. 2005, 77 (16), 5407-5413). Current detection methods for 2-PP include high performance liquid chromatography with UV, electrochemical detection, and gas chromatography with mass spectrometric detection (Thompson, R. D. Determination of Phenolic Disinfectant Agents in Commercial Formulations by Liquid Chromatography; 2001; Vol. 84). These methods, which apply to detection of other pollutants or chemicals in an environment, require extractions, are labor intensive, require expensive equipment, or are low throughput and are not suitable for applications like personal protection and persistent environmental monitoring of large areas. Biosensors that are portable, deployable and require no power for detection of 2-PP, and other analytes such as pollutants or chemicals, in the environment are needed.

BRIEF SUMMARY OF THE DISCLOSURE

Provided is a polynucleotide comprising a *Pseudomonas azelaica* hbpR (hbpR) promoter operably linked to a polynucleotide encoding a HbpR protein and a heterologous promoter operably linked to a polynucleotide encoding a marker protein, wherein the marker protein creates an output signal. In some aspects, the output signal is in the visible spectrum.

In some aspects, the hbpR promoter and the heterologous promoter direct transcription in opposite directions.

In some aspects, the heterologous promoter is a *Pseudomonas azelaica* hbpC promoter.

In some aspects, the polynucleotide further comprises an amplification cassette comprising: a polynucleotide encoding a *Pseudomonas syringae* hrpR (HrpR) protein that is operably linked to the hbpC promoter.

In some aspects, the amplification cassette further comprises a polynucleotide encoding a *Pseudomonas syringae* hrpS (HrpS) protein downstream of the polynucleotide encoding the HrpR protein.

In some aspects, the polynucleotide further comprises a *P. syringae* hrpL (hrpL) promoter operably linked to a polynucleotide encoding a HrpR protein, a polynucleotide encoding a HrpS protein, and a polynucleotide encoding a marker protein.

In some aspects, the polynucleotide comprises a hrpL promoter operably linked to a polynucleotide encoding a HrpS protein, a polynucleotide encoding a HrpR protein, and a polynucleotide encoding a marker protein.

In some aspects, the HbpR protein encoded by the polynucleotide binds an analyte of interest.

In some aspects, the analyte of interest is a polyphenyl selected from the group consisting of 2-hydoxybiphenyl, 2,2'-dihydroxybiphenyl, 2-aminobiphenyl, and 2-hydroxybiphenylmethane.

In some aspects, the polynucleotide encoding the HbpR protein comprises at least one mutation compared to a polynucleotide encoding a wild-type HbpR protein.

In some aspects, the HbpR protein that comprises the at least one mutation binds a different analyte of interest than a wild-type HbpR protein. In some aspects, the different analyte of interest is a chlorinated polyphenyl. In some aspects, the analyte is a polychlorinated polyphenyl.

In some aspects, the marker protein is an amilCP protein.

Further provided is a polynucleotide comprising a *P. syringae* hrpL promoter operably linked to a polynucleotide encoding a HrpR protein and a polynucleotide encoding a marker. In some aspects, the polynucleotide comprises a hrpL promoter operably linked to a polynucleotide encoding a HrpS protein and a polynucleotide encoding a marker protein.

In some aspects, the polynucleotide comprises a *P. syringae* hrpL promoter operably linked to a polynucleotide encoding a HrpR protein, a polynucleotide encoding a HrpS protein, and a polynucleotide encoding a marker.

Also provide is a biocontainment material for containment and maintenance of a microbe comprising a polynucleotide as described herein.

In some aspects, the biocontainment material comprises a polymer-based hydrogel, a multi-layer hydrogel comprising a hydrogel and an elastomer outer layer, or a polymer-inorganic material hybrid hydrogel.

In some aspects, the polymer-based hydrogel comprises polyacrylamide alginate, chitosan, agarose, agar, gelatin, or pullulan.

In some aspects, the polyacrylamide alginate comprises alginate and polyacrylamide at a ratio of alginate to polyacrylamide of about 1:50.

In some aspects, the elastomer outer layer of the multilayer hydrogel comprises a polyurethane skin.

In some aspects, the polymer-inorganic material hybrid hydrogel comprises alginate polyacrylamide and polycaprolactone.

Further provided is a method of preparing a biosensor system, wherein the method comprises (i) preparing a polymer solution; (ii) polymerizing the polymer solution; (iii) suspending a microbe comprising a polynucleotide as described herein in the polymer solution to prepare a polymer cell suspension; and (iv) cross-linking the polymer cell suspension to prepare a biosensor system.

In some aspects, the polymer used in the method is polyacrylamide alginate, chitosan, agarose, agar, gelatin, or pullulan.

BRIEF DESCRIPTION OF THE FIGURES

FIG. 2A shows a schematic of a bacterial cell containing a nucleic acid with an HbpR expression cassette and an amilCP reporter gene under the control of a hbpC promoter; an unbound HbpR protein; a 2-phenylphenol molecule; an HbpR protein/2-phenylphenol complex bound to an hbpC promoter; and amilCP reporter proteins. FIG. 2B shows a photograph of an end-to-end living sensor.

DETAILED DESCRIPTION OF THE DISCLOSURE

Figure 1A:
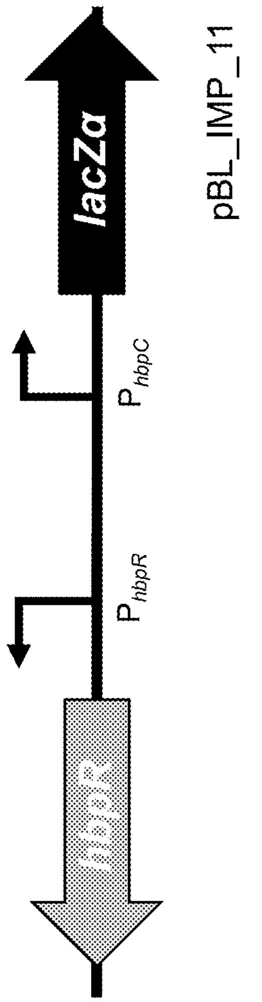
FIG. 1A shows a plasmid (pBL_IMP_11) containing a hbpR expression cassette and a lacZ reporter gene under the control of a hbpC promoter.
Figure 1B:
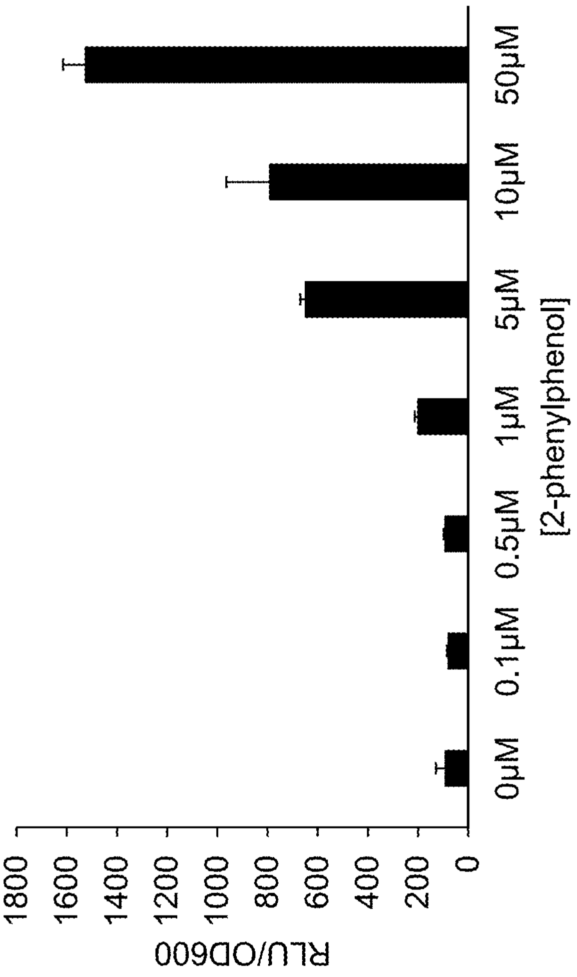
FIG. 1B shows a lacZ signal generated by bacterial sensor cells transfected with plasmid pBL_IMP_11 and cultured in the presence of increasing concentrations of a 2-phenylphenol analyte.

Provided is a whole-cell biosensor system with robust biocontainment for field deployment and a strong visual reporter for readouts in the deployed environment. The engineered biosensors in an encapsulated and deployable system (eBEADS) demonstrate a portable, no power living sensor for detection of a phenylphenol compound, 2-PP, in the environment. In some aspects, a whole-cell living sensor to detect a phenylphenol compound is provided that is developed in *Escherichia coli* by utilizing the 2-PP degradation pathway with an amplification circuit to produce a visual colorimetric output. Such whole-cell biosensors can also be used to detect other analytes, including compounds that HbpR proteins bind to naturally or by engineering of the HbpR protein, e.g., by mutation of the protein. To enable field deployment, a physical biocontainment system is used. In some aspects, the biocontainment system comprises polyacrylamide alginate (PAA) beads to encapsulate the bacterial sensor strains, support long-term viability without supplemental nutrients, and allow permeability of the target analyte.

In some aspects, provided are polynucleotides, bacterial sensor cells, and biosensor systems engineered to sense analytes in an environment, e.g., an ecosystem such as in an urban, rural, or wild area. The biosensor system described herein comprises a bacterial cell that is engineered to express a marker protein upon contact with an analyte. In some aspects, the bacterial cell comprises a polynucleotide comprising a *Pseudomonas azelaica* HbpR protein expression cassette and a marker protein expression cassette under the control of a promoter that is inducible by a complex of HbpR protein and an analyte.

In some aspects, in the presence of the analyte, HbpR binds the analyte to form an HbpR/analyte complex, and the HbpR/analyte complex binds and activates the HbpR/analyte-inducible promoter leading to marker protein expression. In some aspects, the level of marker protein expressed correlates with the amount of HbpR/analyte complex bound to the inducible promoter, and, thus, the amount of analyte in contact with or that contacted the bacterial cell.

In some aspects, polynucleotides provided herein further comprise an amplification circuit that utilizes components of the Hrp Type III secretion system from *Pseudomonas syringae*. In some aspects, the amplification system comprises a polynucleotide encoding transcriptional activator proteins of *P. syringae* downstream of a HbpR/analyte complex inducible promoter. In some aspects, the HbpR/analyte complex inducible promoter is a hbpC promoter. In some aspects, the bacterial cell further comprises a polynucleotide encoding additional transcriptional activator proteins of *P. syringae* downstream of a hrpL promoter. Upon exposure of a bacterial cell to an analyte, the HbpR protein expressed by the HbpR expression cassette binds the analyte and the HbpR/analyte complex binds and activates the hbpC promoter to induce expression of the transcriptional activator proteins. The transcriptional activator protein in turn forms a hexameric complex and binds and activates the hrpL promoter that controls the expression of a marker protein and further transcriptional activator proteins, thereby amplifying the activation circuit and increasing marker protein expression. The amplification circuit leads to an amplified marker protein signal that can be detected with the naked eye.

Further provided is a biocontainment system that contains the engineered bacterial cells. The biocontainment system allows entry of water, nutrients and environmental analytes and prevents biosensor cells from leaking out of the biocontainment system.

Definitions

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

The term "approximately" or "about" as applied to one or more values of interest, refers to a value that is similar to a stated reference value and within a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). When the term "approximately" or "about" is applied herein to a particular value, the value without the term "approximately" or "about is also disclosed herein.

As described herein, any concentration range, percentage range, ratio range, or integer range is to be understood to include the value of any integer within the recited range and, when appropriate, fractions thereof (such as one tenth and one hundredth of an integer), unless otherwise indicated.

The terms "ug" and "uM" are used herein interchangeably with "µg" and "µM," respectively.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The terms "nucleic acids," "nucleic acid molecules," "nucleotides," "nucleotide(s) sequence," and "polynucleotide" can be used interchangeably and refer to the phosphate ester polymeric form of ribonucleosides (adenosine, guanosine, uridine or cytidine; "RNA molecules", including mRNA) or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA). A "nucleic acid composition" comprises one or more nucleic acids as described herein. RNA can be obtained by transcription of a DNA-sequence, e.g., inside a cell. In a prokaryotic cell, transcription of DNA usually results in premature RNA, which has to be processed into messenger RNA (mRNA). Processing of the premature RNA comprises a variety of different posttranscriptional-modifications such as splicing, 5'-capping, polyadenylation, export from the nucleus or the mitochondria and the like. The sum of these processes is also called maturation of RNA. The mature mRNA provides the nucleotide sequence that can be translated into an amino acid sequence of a particular peptide, or protein. Typically a mature mRNA comprises a 5' cap, optionally a 5' UTR, an open reading frame, optionally a 3' UTR, and a poly(A) sequence.

The term "mRNA," as used herein, refers to a single stranded RNA that encodes the amino acid sequence of one or more polypeptide chains.

As used herein, the terms "derived from" or "derivative" refer to a component that is isolated from or made using a specified molecule, or information (e.g., a nucleic acid sequence) from the specified molecule. For example, a polynucleotide sequence that is derived from another polynucleotide sequence can include a polynucleotide sequence that is identical or substantially similar to the polynucleotide sequence it derives from. In the case of polynucleotides, the derived species can be obtained by, for example, naturally occurring mutagenesis, artificial directed mutagenesis, or artificial random mutagenesis. The mutagenesis used to derive polynucleotides can be intentionally directed or intentionally random, or a mixture of both. The mutagenesis of a polynucleotide to create a different polynucleotide derived from the first polynucleotide can be a random event (e.g., caused by polymerase infidelity) and the identification of the derived polynucleotide can be made by appropriate screening methods known in the art. In some aspects, the screening methods comprise exposure to analytes and detection of growth of polynucleotide containing cells in the presence of the analytes. In some aspects, a polynucleotide sequence that is derived from a first polynucleotide sequence has a sequence identity of at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identity to the first polynucleotide sequence, respectively, wherein the derived polynucleotide sequence retains the biological activity of the original polynucleotide. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

As used herein, the term "transfecting" or "transfection" refers to the transport of nucleic acids from the environment external to a cell to the internal cellular environment, with particular reference to the cytoplasm of a prokaryotic cell. Without being bound by any particular theory, it is to be understood that nucleic acids can be delivered to a cell either after being encapsulated within or adhering to one or more cationic polymer/nucleic acid complexes or being entrained therewith or by electroporation or calcium chloride. Nucleic acids include DNA and RNA as well as synthetic congeners thereof. Such nucleic acids include missense, antisense, nonsense, as well as protein producing nucleotides. In particular, but not limited to, they can be genomic DNA, cDNA, mRNA, tRNA, rRNA, hybrid sequences or synthetic or semi-synthetic sequences, and of natural or artificial origin. In addition, the nucleic acid can be variable in size, ranging from oligonucleotides to chromosomes. These nucleic acids can be of mammalian, bacterial, viral, or synthetic origin. They can be obtained by any technique known to a person skilled in the art.

"Percent (%) sequence identity" or "percent identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values can be generated using the sequence comparison computer program BLAST.

By "level" is meant a level or activity of a protein, or mRNA encoding the protein, optionally as compared to a reference. The reference can be any useful reference, as defined herein. By a "decreased level" or an "increased level" of a protein is meant a decrease or increase in protein level, as compared to a reference. A level of a protein can be expressed in mass/vol (e.g., g/dL, mg/mL, g/mL, ng/mL) or percentage relative to total protein or mRNA in a sample.

By a "reference" is meant any useful reference used to compare protein or mRNA levels or activity. The reference can be any sample, standard, standard curve, or level that is used for comparison purposes. The reference can be a normal reference sample or a reference standard or level.

The term "recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed cells. The cell expresses the foreign gene to produce the protein under expression conditions.

The terms "recombinant host cells", "host cells," "cells", "cell lines," "cell cultures", and other such terms denoting microorganisms cultured as unicellular entities refer to cells which can be, or have been, used as recipients for recombinant nuclei acid, and include the original progeny of the original cell which has been transfected.

"Operably linked" refers to an arrangement of elements wherein the components so described are configured so as to perform their usual function. Thus, a given promoter operably linked to a coding sequence is capable of effecting the expression of the coding sequence when the proper enzymes are present. Expression is meant to include the transcription of mRNA from a DNA or RNA template and can further include translation of a protein from an mRNA template. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

As used herein, the term "promoter" refers to DNA sequence capable of controlling the expression of a coding sequence or functional RNA. In some aspects, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters."

Promoters that are induced and cause a gene to be expressed following exposure or treatment of the cell with an agent, biological molecule, chemical, ligand, light, or the like that induces the promoter are commonly referred to as "inducible promoters" or "regulatable promoters." Inducible promoter include any promoter whose activity is affected by a cis or trans-acting factor. In some aspects, an inducible promoter includes a promoter that is induced by binding, e.g., of a transcription factor/analyte complex. In some aspects, the inducible promoter is one derived from an inducible promoter present in nature. In some aspects, an inducible promoter is one generated by DNA synthesis or cloning techniques. In some aspects, an inducible promoter can combine promoter elements originating from several different naturally occurring promoters.

The term "hbpR promoter," as used herein refers to a region upstream of a HbpR protein encoding region of *Pseudomonas azelaica* HBP1, a soil bacterium that is able to grow on the fungicide 2-hydroxybiphenyl as sole source of carbon and energy. The hbpR promoter drives expression of a 63 kDa Hrp regulatory protein. In some aspects, the hbpR promoter comprises the nucleic acid sequence of SEQ ID NO: 1.

The term "hbpC promoter," as used herein refers to a region upstream of a hbpC gene which is the first gene of the 2-hydroxybiphenyl degradation pathway in *Pseudomonas azelaica* HBP1. In some aspects, the hbpC promoter comprises the nucleic acid sequence of SEQ ID NO: 2.

The term "hrpL promoter," as used herein refers to a hrpL promoter of *Pseudomonas syringae*. In some aspects, the hrpL promoter comprises the nucleic acid sequence of SEQ ID NO: 3.

It is further recognized that since in most cases the exact boundaries of regulatory sequences have not been completely defined, DNA fragments of different lengths can have identical promoter activity.

The terms "transcriptional regulatory protein," "transcriptional regulatory factor," and "transcription factor" are used interchangeably herein, and refer to a protein that binds a DNA response element and thereby transcriptionally regulates the expression of an associated gene or genes. Transcriptional regulatory proteins generally bind directly to a DNA response element, however in some cases binding to DNA can be indirect by way of binding to another protein or small molecule and the protein/small molecule complex in turn binds to, or is bound to a DNA response element. In some cases, transcriptional regulatory proteins bind to a DNA response element only when in a complex with an activating moiety. In some aspects, the activating moiety can be an analyte.

The terms "coding sequence" or a sequence "encoding" a particular molecule (e.g., a selectable marker protein) as used herein refer to a nucleic acid that is transcribed (in the case of DNA) or translated (in the case of mRNA) into polypeptide, in vitro or in vivo, when operably linked to an appropriate regulatory sequence, such as a promoter. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the coding sequence.

The term "termination signal sequence" as used herein refers to any genetic element that causes RNA polymerase to terminate transcription, such as for example a polyadenylation signal sequence. A polyadenylation signal sequence is a recognition region necessary for endonuclease cleavage of an RNA transcript that is followed by the polyadenylation consensus sequence AATAAA. A polyadenylation signal sequence provides a "polyA site," i.e., a site on a RNA transcript to which adenine residues will be added by post-transcriptional polyadenylation.

The term "mutation" as used herein refers to any changing of the structure of a gene, resulting in a variant (also called "mutant") form that can be transmitted to subsequent generations. Mutations in a gene can be caused by the alternation of single base in DNA, or the deletion, insertion, or rearrangement of larger sections of genes or chromosomes.

The term "modified" as used herein refers to a changed state or structure of a molecule of the disclosure. Molecules can be modified in many ways including chemically, structurally, and functionally. In some aspects, the modification is relative to a reference wild-type molecule.

The term "synthetic" as used herein refers to produced, prepared, and/or manufactured by the hand of man. Synthesis of polynucleotides or polypeptides or other molecules of the present disclosure can be chemical or enzymatic.

The term "polypeptide" as used herein is intended to encompass a singular "polypeptide" as well as plural "polypeptides," and comprises any chain or chains of two or more amino acids. Thus, as used herein, a "peptide," a "peptide subunit," a "protein," an "amino acid chain," an "amino acid sequence," or any other term used to refer to a chain or chains of two or more amino acids, are included in the definition of a "polypeptide," even though each of these terms can have a more specific meaning. The term "polypeptide" can be used instead of, or interchangeably with any of these terms.

The term "hydrogel" as used herein refers to a cross-linked hydrophilic polymer that is water soluble before cross-linking and includes, but is not limited to, a polyacrylamide hydrogel; polyacrylic acid hydrogel, polymethacrylic acid hydrogel, polyvinylalcohol hydrogel, polyethyleneglycol hydrogel, polylactic acid hydrogel; polyglycolic acid hydrogel, poly(lactic-co-glycolic acid) hydrogel, alginate polyacrylamide hydrogel; alginate polyacrylic acid hydrogel, alginate polymethacrylic acid hydrogel, alginate polyvinylalcohol hydrogel, alginate polyethyleneglycol hydrogel, alginate polylactic acid hydrogel; alginate polyglycolic acid hydrogel, alginate poly(lactic-co-glycolic acid) hydrogel; carboxymethyl cellulose hydrogel, hydroxyethyl cellulose hydrogel, and a starch-acrylic acid copolymer hydrogel. After cross-linking the hydrogel may degrade in water over time where the degradation rate depends on the composition of the hydrogel.

The term "hybrid" material, as used herein, refers to a material that contains at least two different components including, but not limited to, two materials with different tensile strengths and/or transparency.

The term "elastomer skinned polymer-based hydrogel," as used herein, refers to a hydrogel that comprises a polymer-based component and an elastomer component that surrounds the polymer-based component in a skin-like manner.

The terms "analyte" or "analyte of interest," as used herein, refers to a compound or substance that is capable of detection using the whole-cell biosensor systems described herein, where an HbpR protein expressed by the bacterial sensors is capable of binding the analyte and is capable of activating the transcriptional activator protein HbpR. Example analytes described herein include, but are not limited to, phenylphenol compounds, such as 2-PP, chlorinated polyphenyl compounds, and chlorinated biphenyl compounds.

The term "phenylphenol" refers to a diphenyl-based compound that may contain a substitution in one of the phenyl rings and is capable of interacting with a HpR protein as disclosed herein. An example phenylphenol described herein includes "hydroxyl-phenylphenol," "OH-phenylphenol," "substituted diphenyl," "2-phenylphenol," "2-PP," "2-HBP," "2-OH-PP," or "2-OH-BP," which are used interchangeably.

The term "whole cell biosensor," as used herein, refers to an analyte detection system that uses whole cells, e.g., whole bacterial cells for the expression of an analyte detection system that enables detection of an analyte through, e.g., a color change of the whole cell biosensor.

Polynucleotides

Provided are polynucleotides comprising an HbpR/analyte complex-inducible marker protein expression system for biosensing analytes in an environment.

The polynucleotides comprise components of the 2-phenylphenol and 2,2'-biphenol degradation pathway of *Pseudomonas azelaica* HBP1. This pathway is regulated by the transcriptional activator protein HbpR.

In some aspects, a polynucleotide comprises a *Pseudomonas azelaica* HbpR protein expression cassette comprising a *P. azelaica* hbpR promoter operably linked to a polynucleotide encoding a *P. azelaica* HbpR protein. In some aspects, the hbpR promoter comprises SEQ ID NO: 1. In some aspects, the polynucleotide further comprises a promoter that is inducible by a HbpR/analyte complex operably linked to a polynucleotide encoding a marker protein.

In some aspects, the polynucleotide further comprises a polynucleotide encoding a *P. syringae* HrpR transcriptional activator protein. In some aspects, the polynucleotide further comprises a polynucleotide encoding a *P. syringae* HrpS transcriptional activator protein. In some aspects, the polynucleotide encoding the *P. syringae* HrpR transcriptional activator protein and the polynucleotide encoding a *P. syringae* HrpS transcriptional activator protein are under the control of a hbpC promoter. In some aspects, the hbpC promoter comprises SEQ ID NO: 2. In some aspects, the polynucleotide encoding the *P. syringae* HrpR transcriptional activator protein is operably linked to the hbpC promoter and the polynucleotide encoding the *P. syringae* HrpS transcriptional activator protein is downstream of the polynucleotide encoding the *P. syringae* HrpR transcriptional activator. In some aspects, the polynucleotide encoding the *P. syringae* HrpS transcriptional activator protein is operably linked to the hbpC promoter and the polynucleotide encoding the *P. syringae* HrpR transcriptional activator protein is downstream of the polynucleotide encoding the *P. syringae* HrpS transcriptional activator protein.

In some aspects, the polynucleotide encoding a *P. syringae* HrpR transcriptional activator protein and the polynucleotide encoding a *P. syringae* HrpS transcriptional activator protein are linked through an IRES.

In some aspects, the polynucleotide encoding a *P. syringae* HrpR transcriptional activator protein and the polynucleotide encoding a *P. syringae* HrpS transcriptional activator protein are linked through a self-cleaving peptide.

In some aspects, provided is a polynucleotide comprising a *P. syringae* HrpL promoter operably linked to a marker protein, a *P. syringae* HrpR protein, and a *P. syringae* HrpS protein. In some aspects, the hrpL promoter comprises SEQ ID NO: 3. When co-expressed, HrpR and HrpS proteins form a hetero-hexameric complex that binds to and activates the *P. syringae* HrpL promoter, thereby inducing enhanced expression of the complex components, HrpR and HrpS protein, and of the marker protein. Therefore, the polynucleotide provides an amplification of the marker protein signal.

In some aspects, the *P. azelaica* HbpR expression cassette and the HbpR/analyte complex-inducible promoter-HrpR-HrpS-marker protein expression cassette are present in the same polynucleotide. In some aspects, the *P. azelaica* HbpR expression cassette promoter and the HbpR/analyte complex-inducible-HrpR-HrpS-marker protein expression cassette are transcribed in opposite directions.

In some aspects, the *P. azelaica* HbpR expression cassette and the HbpR/analyte complex-inducible-HrpR-HrpS-marker protein expression cassette are present in different polynucleotides.

In some aspects, the hrpL promoter-HrpR-HrpS-marker protein expression cassette, the *P. azelaica* HbpR expression cassette, and the HbpR/analyte complex-inducible promoter-HrpR-HrpS-marker protein expression cassette are present in one polynucleotide.

In some aspects, the hrpL promoter-HrpR-HrpS-marker protein expression cassette and the HbpR/analyte complex-inducible-HrpR-HrpS-marker protein expression cassette are present in one polynucleotide and the *P. azelaica* HbpR expression cassette.

In some aspects, the hrpL promoter-HrpR-HrpS-marker protein expression cassette and the *P. azelaica* HbpR expression cassette are present in one polynucleotide and the HbpR/analyte complex-inducible-HrpR-HrpS-marker protein expression cassette is present in a separate polynucleotide.

In some aspects, the marker protein is a LacZ gene, a green fluorescent protein (GFP) gene, a red fluorescent protein (RFP) gene, a yellow fluorescent protein (YFP) gene, or an amilCP protein. In some aspects, the marker protein is amilCP and the purple-blue color produced by the expressed amilCP causes a whole cell biosensor containing the amilCP-expressing bacteria to turn purple blue, wherein the purple blue color of the biosensor can be detected with the naked eye.

In some aspects, the *P. azelaica* HbpR expression cassette encodes a wild-type HbpR. In some aspects, the wild-type HbpR binds a hydroxylated biphenyl. In some aspects, the wild-type HbpR binds a 2-hydroxy-biphenyl, 1,2-diphenyl hydrazine, 1-bromo-4-phenoxy benzene, 1-chloro-4-phenoxy benzene, 2-chloronaphtalene, benzidine, or 1-fluoro-4-phenoxy-benzene.

In some aspects, the HbpR encoding polynucleotide comprises at least one mutation compared to a wild-type HbpR encoding polynucleotide, wherein the at least one mutation changes the analyte affinity and/or specificity of the HbpR protein.

In some aspects, the mutant HbpR binds a chlorinated biphenyl. In some aspects, the mutant HbpR binds a polychlorinated biphenyl. In some aspects, the polychlorinated biphenyl is polychlorinated biphenyl-1 (PCB-1). In some aspects, the polychlorinated biphenyl is polychlorinated biphenyl-3 (PCB-3). In some aspects, the mutant HbpR does not bind 2-phenylphenol and does bind PCB-1. In some aspects, the mutant HbpR does not bind 2-phenylphenol and does bind PCB-3. In some aspects, the mutant HbpR binds 2-phenylphenol with low affinity and PCB-1 with high affinity. In some aspects, the mutant HbpR binds 2-phenylphenol with low affinity and PCB-3 with high affinity.

In some aspects, the mutant HbpR protein is encoded by a polynucleotide comprising SEQ ID NO: 5. In some aspects, the mutant HbpR protein is encoded by a polynucleotide comprising SEQ ID NO: 6. In some aspects, the mutant HbpR protein is encoded by a polynucleotide comprising SEQ ID NO: 7.

Microbes

In some aspects, the polynucleotides described herein are present in a bacterial cell. In some aspects, the bacteria are transformed to contain at least one polynucleotide as described herein. In some aspects, the bacteria are transformed to contain at least two polynucleotides as described herein.

In some aspects, the bacterial cell is a soil bacterium. In some aspects, the soil bacterium includes, but is not limited to, the genera *Rhizobium, Bacillus, Mycobacterium, Streptomyces, Xanthomonas, Arthrobacter, Micrococcus, Pseudomonas, Corynebacterium, Agrobacterium, Flavobacterium, Alcaligenes, Clostridium*, or *Azospirillum*.

In some aspects, the polynucleotides used with the soil bacteria comprise modifications. In some aspects, the modifications comprise changes to promoters, ribosomal binding sites, or other genetic regulatory elements that can be used in the respective soil bacterium, and combinations thereof.

In some aspects, the bacterial cell is *Escherichia* co/i.

In some aspects, the bacterial cells are whole cell biosensors that express a marker protein upon being contacted with an analyte. In some aspects, the expression levels of the marker protein in the bacterial cell are directly correlated to the amount of analyte the bacterial cell was contacted with.

In some aspects, the bacterial whole cell biosensor is contained within a biocontainment element such that expression of the marker protein by the bacterial cell induces a color change of the biocontainment element.

Biocontainment Elements

Provided are materials and method of using the same to contain a bacterial whole cell biosensor such that entry of the bacterial cell into the environment is prevented. In some aspects, the integration of biocontainment materials and sensing bacterial strains provides a deployable end-to-end living whole cell biosensor system. In some aspects, the biosensor system comprises a β-galactosidase reporter. In some aspects, the biosensor system comprises an amplification circuit. In some aspects, the biosensor system enables an up to 66-fold increase in β-galactosidase reporter output with the addition of the amplification circuit. In some aspects, the whole cell biosensor responds to as little as about 1 μM 2-PP when unencapsulated. In some aspects, the whole cell biosensor system when contained in a biocontainment element responds to about 10 μM 2-PP.

In some aspects, the biocontainment material comprises pores that are large enough to allow entry of water, nutrients and analytes into the interior of the biocontainment element and small enough to prevent whole cell biosensor bacteria to leave the biocontainment element. In some aspects, the biocontainment materials comprise ion crosslinked hydrogels. In some aspects, the biocontainment materials comprise several components that are selected based on their capability of forming pores of desired diameters upon crosslinking. In some aspects, the biocontainment elements are customized according to the size of whole cell biosensor bacteria they are to contain and according to the environment in which the biocontained whole cell sensors are to be deployed. In some aspects, when the biocontained whole cell sensors are to be deployed in a dry environment, the biocontainment materials are selected to enable sufficient hydration and may include a hydration retention additive such as, e.g., glycerol.

In some aspects, the biocontainment material comprises a polymer-based hydrogel, a polymer-based multilayer hydrogel, an elastomer skinned polymer-based hydrogel, or a polymer-inorganic material hybrid hydrogel.

In some aspects, the polymer is a polyacrylamide-alginate, alginate, chitosan, agarose, agar, gelatin, or pullulan.

In some aspects, the polymer-based hydrogel is a polyacrylamide-alginate hydrogel and comprises alginate, polyacrylamide and N,N'-Methylenebisacrylamide (MBAA).

In some aspects, the alginate polyacrylamide hydrogel comprises alginate and polyacrylamide in a ratio of alginate to polyacrylamide of about 1:40, about 1:42, about 1:44, about 1:46, about 1:48, about 1:50, about 1:52, about 1:54, about 1:56, about 1:58 or about 1:60. In some aspects, the ratio of alginate to polyacrylamide is from about 1:40 to about 1:50; about 1:40 to about 1:60; or about 1:42 to about 1:60; about 1:44 to about 1:58; about 1:46 to about 1:56; about 1:48 to about 1:54; or about 1:50 to about 1:52.

In some aspects, the ratio of alginate to polyacrylamide is from about 1:40 to about 1:60. In some aspects, the ratio of alginate to polyacrylamide is from about 1:45 to about 1:55. In some aspects, the ratio of alginate to polyacrylamide is about 1:45. In some aspects, the ratio of alginate to polyacrylamide is about 1:55.

In some aspects, the ratio of alginate to polyacrylamide is about 1:50.

In some aspects, the alginate polyacrylamide hydrogel comprises about 1.0, 1.1, 1.2, 1.3, 1.4, 1.5, 1.6, 1.7, 1.8, 1.9, or 2.0% of MBAA. In some aspects, the alginate polyacrylamide hydrogel comprises about 1.0 to about 1.4; about 1.5 to about 1.7; or about 1.8 to about 2.0% MBAA. In some aspects, the alginate polyacrylamide hydrogel comprises about 1.0 to about 2.0; about 1.1 to about 1.9; about 1.2 to about 1.8, about 1.3 to about 1.7, or about 1.4 to about 1.6% MBAA.

In some aspects, the alginate polyacrylamide hydrogel comprises about 1.65, about 1.66, about 1.67, about 1.68, about 1.69, about 1.75, about 1.85, or about 1.95% of MBAA. In some aspects, the alginate polyacrylamide hydrogel comprises about 1.65 to about 1.67, about 1.68 to about 1.75, or about 1.76 to about 1.95% MBAA. In some aspects, the alginate polyacrylamide hydrogel comprises about 1.65 to about 1.95, about 1.66 to about 1.9, about 1.67 to about 1.85, about 1.68 to about 1.8, or about 1.69 to about 1.75% of MBAA.

In some aspects, the polymer-based hydrogel comprises an elastomer skin. In some aspects, the elastomer skinned polymer-based hydrogel comprises a polyurethane skin.

In some aspects, the polymer-inorganic material hybrid hydrogel comprises an inorganic nanomaterial reinforced hydrogel. In some aspects, the inorganic nanomaterial reinforced hydrogel comprises alginate polyacrylamide and polycaprolactone.

In some aspects, the inorganic nanomaterial reinforced hydrogel comprises between about 0.1 mg/ml and about 10 mg/ml of polycaprolactone. In some aspects, the inorganic nanomaterial reinforced hydrogel comprises about 0.1 mg/ml to about 1 mg/ml; about 1.1 mg/ml to about 2 mg/ml; about 2.1 mg/ml to about 3 mg/ml; about 3.1 mg/ml to about 4 mg/ml; about 4.1 mg/ml to about 5 mg/ml; about 5.1 mg/ml to about 6 mg/ml; about 6.1 mg/ml to about 7 mg/ml; about 7.1 mg/ml to about 8 mg/ml; about 8.1 mg/ml to about 9 mg/ml; about 9.1 mg/ml to about 10 mg/ml of polycaprolactone.

In some aspects, the inorganic nanomaterial reinforced hydrogel comprises about 1 mg/ml of polycaprolactone.

In some aspects, the polymer-inorganic material hybrid hydrogel comprises a polycrystalline polymer. In some aspects, the polymer-inorganic material hybrid hydrogel comprises a polycrystalline polymer that is shear thinning. In some aspects, the shear thinning polycrystalline polymer hybrid hydrogel can be used for 3D extrusion printing.

In some aspects, the polymer-inorganic material hybrid hydrogel comprises clay. In some aspects, the polymer-inorganic material hybrid hydrogel comprises laponite. In some aspects, the polymer-inorganic material hybrid hydrogel comprises silica.

Biosensor System

Provided is a biosensor system comprising a bacterial cell described herein and a biocontainment material described herein encapsulating the bacterial cell.

In some aspects, the biosensor system further comprising a hydration retention additive. In some aspects, the hydration retention additive is glycerol.

In some aspects, the biosensor system is designed such that the biocontainment material contains the bacterial cells within the biosensor system and allows nutrients, water and analytes to penetrate the biocontainment material. In some aspects, the bacterial cell does not leak out of the engineered biocontainment material for at least about nine days. In some aspects, the bacterial cell does not leak out of the engineered biocontainment material for about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56 days. In some aspects, the bacterial cell does not leak out of the engineered biocontainment material for about 10 to about 15, about 16 to about 20, about 21 to about 25, about 26 to about 30, about 31 to about 35, about 36 to about 40, about 41 to about 45, about 46 to about 50, about 51 to about 56 days; or about 10 to about 56, about 12 to about 54, about 14 to about 52, about 16 to about 50, about 18 to about 48, about 20 to about 46, about 22 to about 42, about 24 to about 40, about 26 to about 38, about 28 to about 36, or about 30 to about 34 days.

In some aspects, the bacterial cell remains viable in the biosensor system for about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56 days. In some aspects, the bacterial cell remains viable in the biosensor system for about 10 to about 15, about 16 to about 20, about 21 to about 25, about 26 to about 30, about 31 to about 35, about 36 to about 40, about 41 to about 45, about 46 to about 50, about 51 to about 56 days; or about 10 to about 56, about 12 to about 54, about 14 to about 52, about 16 to about 50, about 18 to about 48, about 20 to about 46, about 22 to about 42, about 24 to about 40, about 26 to about 38, about 28 to about 36, or about 30 to about 34 days.

In some aspects, the bacterial cell of the biosensor system remains viable for between about 9 days and about 56 days.

In some aspects, the biosensor system comprises a bacterial cell that expresses an amilCP marker protein from a polynucleotide as described herein and the biosensor system adopts a purple-blue color when contacted with an analyte.

In some aspects, the biosensor system adopts a purple-blue color between about 6 hours and 24 hours after being contacted with an analyte. In some aspects, the biosensor system adopts a purple-blue color between about 2 hours and 6 hours after being contacted with an analyte.

In some aspects, the biosensor system is contained in a particle. In some aspects, the biosensor system is contained in a microparticle. In some aspects, the microparticle comprising the biosensor system comprising bacterial sensor cells adopts a blue-purple color when contacted with an analyte. In some aspects, the microparticle comprises more than one biosensor system.

In some aspects, the microparticle comprises a polymer.

In some aspects, the microparticle comprises a polymer-based hydrogel. In some aspects the microparticle hydrogel comprises polyacrylamide alginate, chitosan, agarose, agar, gelatin, or pullulan.

In some aspects, the microparticle comprises biosensor systems with bacterial sensor cells comprising polynucleotides encoding different analyte-binding transcriptional activator proteins for detection of different analytes. In some aspects, the marker proteins contained within the different biosensor systems of a microparticle generate a same color and the intensity of the color change of the microparticle is a measure for the presence of different analytes.

In some aspects, the marker proteins contained within the different biosensor systems are different and the colors generated by each biosensor system are a measure for the analyte detected by the respective biosensor system. In some aspects, the different colors generated by the different marker proteins create a distinct combination color indication. In some aspects, one marker protein contained in the biosensor system generates a red fluorescent protein upon being contacted with an analyte and a second marker protein contained in the biosensor system generates a green fluorescent protein upon being contacted with an analyte and, when exposed to light of a wavelength that excites the red and green marker proteins, the biosensor system generates a yellow color if both marker proteins are generated at about equal amounts. In some aspects, the biosensor system generates a green-yellow color when more of the second marker protein is generated. In some aspects, the biosensor system generates an orange color when more of the first marker protein is generated.

In some aspects, a marker protein contained in the biosensor system is amilGFP and generates a yellow color upon being contacted with an analyte. In some aspects, a marker protein contained in the biosensor system is fwYellow and generates a yellow color upon being contacted with an analyte.

In some aspects, a marker protein contained in the biosensor system is meffRFP and generates a red color upon being contacted with an analyte. In some aspects, a marker protein contained in the biosensor system is eforCP and generates a red color upon being contacted with an analyte.

In some aspects, a first marker protein contained in the biosensor system is selected from the group consisting of amilGFP and fwYellow and generates a yellow color upon being contacted with an analyte. In some aspects, a second marker protein contained in the biosensor system is selected from the group consisting of meffRFP and eforCPfwYellow and generates a red color upon being contacted with an analyte.

In some aspects, the marker proteins are generated when contacted with the same analyte. In some aspects, the marker proteins are generated when contacted with different analytes. In some aspects, the biosensor system generates a yellow color when contacted with a first analyte and a red color when contacted with a second analyte. In some aspects, when contacted with both analytes the biosensor generates an orange color. In some aspects, when contacted with more of the first analyte than the second analyte, the biosensor generates a yellow-orange color. In some aspects, when contacted with more of the second analyte than the first analyte, the biosensor generates a red-orange color.

In some aspects, the biosensor system comprises an agent that is cytotoxic to the bacterial sensor cells. In some aspects, the biosensor system further comprises a trigger release system. In some aspects, the release of the cytotoxic agent is triggered by an environmental condition. In some aspects, the release is caused by UV light, magnetic field, pH or temperature. In some aspects, upon triggering the release of the cytotoxic agent within the biosensor system, the bacterial cells of the biosensor system are neutralized.

Methods of Making

Provided is a method of preparing a biosensor system as described herein.

In some aspects, the method comprises: (i) preparing a polymer solution; (ii) polymerizing the polymer solution; and (iii) suspending a bacterial cell comprising a polynucleotide as described herein to prepare a polymer cell suspension.

In some aspects, the method further comprises mixing a polymer cell suspension with a mechanically hard polymer. In some aspects, the mechanically hard polymer is polycaprolactone.

In some aspects, the ratio of cross-linked polymer cell suspension and mechanically hard polymer is from about 50:1 to about 1:50, or any ratio in between.

In some aspects, the method further comprises coating a cross-linked polymer cell suspension with an elastomer skin. In some aspects, the elastomer skin is a polyurethane skin.

In some aspects, the method further comprises co-printing a cross-linked cell polymer suspension using a 3D printer. In some aspects, the 3D printed cross-linked polymer cell suspension is in the form of a film. In some aspects, the 3D printed cross-linked polymer cell suspension is deposited on a particle. In some aspects, the 3D printed cross-linked polymer cell suspension film is deposited on an adhesive structure. In some aspects, the 3D printed cross-linked polymer cell suspension film is deposited on a device deployable into an environment. In some aspects, the 3D printed cross-linked polymer cell suspension film is deposited on a bead. In some aspects, the 3D printed cross-linked polymer cell film is deposited on a microbead.

The engineered biosensors described herein are encapsulated and deployable systems (eBEADS) comprising an amplification circuit that enhances sensor output and, by expressing an amilCP marker protein when exposed to micromolar quantities of, e.g., 2-PP, generate a purple-blue color that is visible to the human eye.

Methods of Using Biosensor Systems and Microparticles for Analyte Detection

Provided are methods for detecting the presence of an analyte in an environment, the method comprising: (i) deploying a biosensor system described herein or a microparticle described herein in an environment; and (ii) detecting an output signal of the biosensor system or microparticle.

In some aspects, provided is a method for measuring a quantity of an analyte in an environment, the method comprising: (i) deploying a biosensor system described herein or a microparticle described herein in an environment; (ii) detecting an output signal of the biosensor system or microparticle; (iii) quantifying the output signal of the biosensor system or microparticle using an output signal scale that indicates a quantity of an analyte for a specified output signal intensity. In some aspects, the output signal scale provides output signal intensities for specified or known quantities of analyte such that an output signal intensity detected with an eBEAD can be quantified.

In some aspects, the quantification of the output signal is after about 1, 2, 3, 4, 5, 6, 7, 8, 9, 10, 12, 14, 16, 18, 20, 22, 24 hours or after about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days of deployment.

EXAMPLES

Materials

All chemicals including 2-phenylphenol (2-PP), ethanol, isopropyl β-D-1-thiogalactopyranoside (IPTG), acrylamide, N,N' methylenebisacrylamide (MBAA), alginic acid sodium salt from brown algae (alginate, medium viscosity), and calcium chloride were obtained from MilliporeSigma (St. Louis, MO).

Media and Growth Conditions for Bacteria

Unless otherwise noted, bacteria were grown at 30° C. in Lysogeny Broth (LB) media (10 g NaCl, 10 g tryptone, and 5 g yeast extract per liter) with carbenicillin (100 μg/mL) and/or kanamycin (50 μg/mL) for selection of plasmids. Plasmids were directly transformed into chemically competent *Escherichia coli* (*E. coli*) NEB5α cells (New England Biolabs, NEB; Ipswich, MA). Strains containing plasmid for plasmid preparation were incubated at 37° C.

Determination of β-Galactosidase Activity for Sensing Strains in Liquid Culture

Cultures were grown overnight to saturation and then diluted to an OD600 of 0.2. Cultures were incubated at 30° C. with shaking until an OD600 of 0.7-1 before inducing cultures with 2-phenylphenol dissolved in 100% ethanol. Cultures were incubate for 3 hours or 1 mL samples were taken every hour. For experiments where 2-PP was removed after incubating for 3 hours, cultures were divided in two tubes and centrifuged. One half of the cultures were washed with 1×PBS to remove 2-phenylphenol and resuspended in fresh medium with antibiotics and without 2-phenylphenol. The other half was resuspended in their original medium without washing. Aliquots were taken every hour. Cells were harvested, washed with 1×PBS, and resuspended in one volume of 1×PBS. One hundred μl were used for analysis using the Beta-Glo Assay System (Promega; Madison, WI) according to the manufacturer's instructions. Statistical significance of results was determined using a Student's two-tailed t-test. The limit of detection (LOD) was calculated using GraphPad Prism software and is defined as the blank plus three times the standard deviation of the blank.

Visual Reporter Demonstration with Amil CP on Plates

Strains containing AmilCP reporters were incubated overnight to saturation at 30° C. with shaking. Three μl of culture were pipetted onto 6 cm LB-agar plates containing 0.2 mM IPTG, 100 μg/mL carbenicillin, 50 μg/mL kanamycin, and 0 μM, 1 μM, or 10 μM of 2-phenylphenol. Images of the plates were taken at time points 0, 6, 12, 24, and 48 hours with a Nikon SMZ25 stereoscope.

Validation of Hydrogel Formulation for Leakage Free Matrix

Using the same encapsulation protocol as the sensing strain beads, positive control strain cultures containing plasmids pBL_IMP_25 and pBL_IMP_26 that constitutively express the reporter were used to fabricate triplicate samples. Negative control beads lacking cells were also fabricated. The sensing strain microbeads were cultured at 30° C., 200 RPM in LB medium with no salt. OD600 measurements of the LB medium surrounding the beads were taken with a NanoDrop One MicroVolume UV-Vis Spectrometer (Thermo Scientific; Waltham, MA) every 24 hours for a nine-day period.

Characterization of Encapsulated Cell Viability

The encapsulation matrix's ability to support cell viability and long-term shelf life was assessed using the Live/Dead BacLight Bacterial Viability assay (ThermoFisher). Briefly, cells constitutively expressing AmilCP were encapsulated in hydrogel formulations as described above and stored at 4° C. or 25° C. without supplemental nutrients or liquid in a closed 50 mL conical tube in biological triplicate "batches". Cell viability was evaluated for each storage condition immediately after encapsulation, 24 hours, and weekly for one month. At each time point and storage condition, a single bead from each replicate "batch" was stained with 1 ml of 3 l/ml equal parts SYTO9 (live stain) and propidium iodide (dead stain) for 30 minutes, washed with 1×PBS, and imaged as an end point measurement on Zeiss Confocal Microscope (LSM 900 Airy scan 2). Images were processed using ImageJ.

Demonstration of Sensor Induction in Hydrogel Microbeads

The encapsulated sensing strain's ability to detect low concentrations of 2-PP and produce a visible output signal were evaluated by time series of microscope images. Briefly, the positive control strain and 2-PP with amplification circuit strain were encapsulated in the PAA formulation as previously described above. The microbeads were placed on LB agar plates containing 0.2 mM IPTG, 100 µg/mL carbenicillin, and 50 µg/mL kanamycin supplemented with 0, 1 or 10 µM 2-phenylphenol and incubated at 30° C. Images of the sensing strain microbeads were taken at time points 0, 6, 12, 24, and 48 hours with a Nikon SMZ25 stereoscope.

Example 1—Plasmid Construction

The plasmids constructed are listed in Table 1. HbpR, its 654 bp upstream region containing the hbpC promoter (Accession U73900), and lacZα were cloned into pAKgfp132 to make pBL_IMP_11. LacZα was replaced with the amilCP reporting gene to make pBL_IMP_31. For the amplification plasmids, hrpR and hrpS were inserted downstream of the hbpC promoter and upstream of either the lacZα or amilCP reporter to make pBL_IMP_32 and pBL_IMP_28, respectively. A ribosome binding site (BBa_B0034, Registry of Standard Biological Parts) was inserted upstream of each hrpR, hrpS, and the reporter gene. For the second amplification plasmid, the entire hrpR, hrpS, and either lacZα or amilCP were cloned downstream of the hrpL promoter into the pVLT3333 plasmid backbone to make pBL_IMP_33 and pBL_IMP_25, respectively. For the positive control plasmids that constitutively express the reporter, the hbpC promoter in pBL_IMP_28 was replaced with the tac promoter to produce pBL_IMP_26. All genetic components were amplified using Q5 polymerase and assembled using NEBluilder® HiFi DNA Assembly Master Mix (NEB). All PCR primers and gBlocks were purchased from Integrated DNA Technologies (IDT; Coralville, Iowa).

TABLE 1

| SEQ ID NO: | Plasmid | Description | Target analyte |
|---|---|---|---|
| 8 | pBL_EB_02 | hbpR library; NNK | PCB-1, PCB-3 |
| 9 | pBL_IMP_11 | pAKgfp1; $P_{hbpR}$-hbpR; $P_{hbpC}$-lacZα; bla | 2-phenylphenol-β-galactosidase |
| 13 | pBL_IMP_31 | pAKgfp1; $P_{hbpR}$-hbpR; $P_{hbpC}$-amilCP; bla | 2-phenylphenol-AmilCP |
| 14 | pBL_IMP_32 | pAKgfp1; $P_{hbpR}$-hbpR; $P_{hbpC}$-hrpR-hrpS-lacZα; bla | 2-phenylphenol amplification circuit-β-galactosidase |
| 15 | pBL_IMP_33 | pVLT33; $P_{hrpL}$-hrpR-hrpS-lacZα; kan | β-galactosidase amplification circuit |
| 12 | pBL_IMP_28 | pAKgfp1; $P_{hbpR}$-hbpR; $P_{hbpC}$-hrpR-hrpS-amilCP; bla | 2-phenylphenol amplification circuit-AmilCP |
| 10 | pBL_IMP_25 | pVLT33; PhrpL-hrpR-hrpS-amilCP; kan | AmilCP amplification circuit |
| 11 | pBL_IMP_26 | pAKgfp1; $P_{lac}$-hrpR-hrpS-amilCP; bla | IPTG induce amplification circuit-AmilCP |

Example 2—Fabrication of Hydrogel Microencapsulation of Sensor Strains

Bacterial sensor cells were prepared by electroporation of the plasmids described above into the bacteria and bacteria were grown overnight as described above.

The bacterial sensing cells were entrapped in a semi-interpenetrating network of alginate and polyacrylamide hydrogel microbeads. To this end, alginate, acrylamide, and MBAA were dissolved in deionized water. The total weight percent of alginate and acrylamide was 33.3% (w/v) at a ratio of 1:50 (w/w) alginate to acrylamide. MBAA was added to a final concentration of 1.67% (w/v). The polymer solution was polymerized in a Branson 1800 sonicator bath containing water at 60° C. for 3 hours and allowed to cool overnight. Overnight cultures of bacteria containing the plasmids (grown as described above) were pelleted and resuspended into the polymer solution at an OD600 of 3 per ml. The polymer cell suspension was then extruded through a sterile 18G needle into 1 M calcium chloride bath and allowed to cross-link for 30 minutes in the bath. The sensing strain microbeads were then filtered and rinsed twice with sterile deionized water.

In the bacterial sensor cells when exposed to 2-PP, the HbpR promoter is activated by 2-PP and HbpR protein is expressed from the transfected plasmids. HbpR protein binds to 2-PP to form a HbpR/2-PP complex that binds to and activates the hbpC promoter also present in the transfected plasmids. Activation of the hbpC promoter results in expression of a lacZα reporter gene (FIGS. 1A and 1*i*). Expression of the HbpR protein increases over time and after three hours in the presence of 2-PP, the lacZ reporter can be activated by as little as 1 M of 2-PP analyte. The Limit of Detection (LOD) was calculated to be 0.863 μM for this sensor strain (FIG. 1*i*). There was no detectable activation at lower concentrations of 2-PP when compared to the negative control.

Figure 1C:
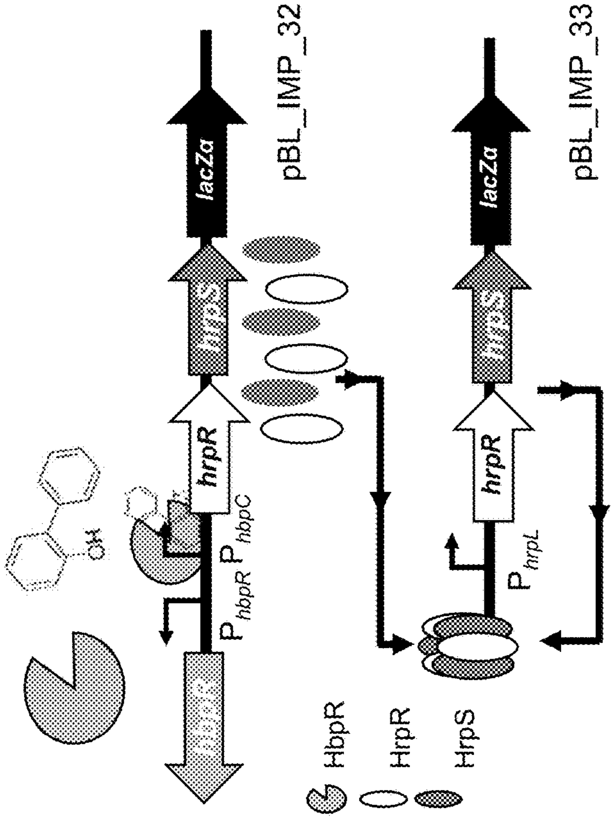
FIG. 1C shows two plasmids of an amplification circuit with one plasmid (pBL_IMP_32) containing the hbpR expression cassette and a hrpR gene, a hrpS gene, and a lacZ reporter gene under the control of a hbpC promoter and a second plasmid (pBL_IMP_33) containing a hrpR gene, hrpS gene, and a lacZ reporter gene under the control of a hrpL promoter.
Figure 1D:
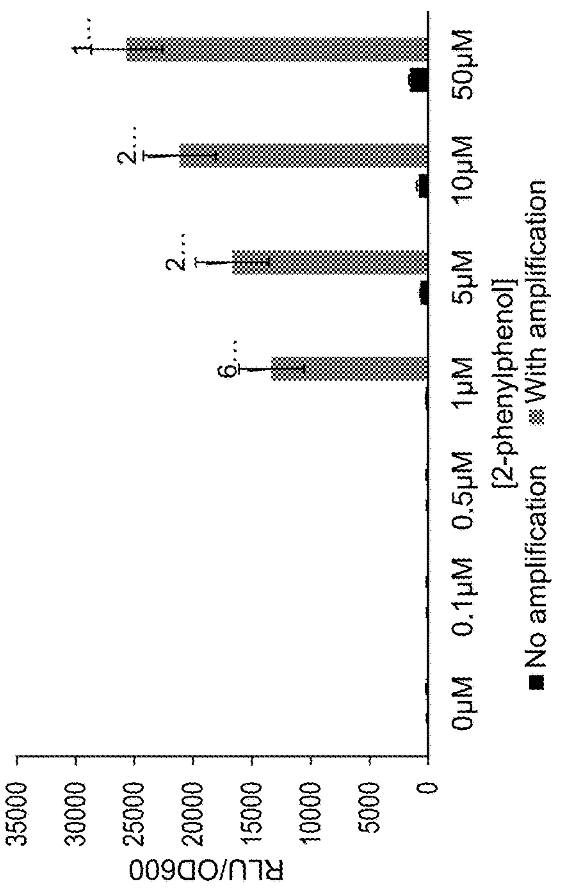
FIG. 1D shows a lacZ signal generated by bacterial sensor cells transfected with either plasmid pBL_IMP_11 (No amplification) or plasmids pBL_IMP_32 and pBL_IMP_33 (With amplification) and cultured in the presence of increasing concentrations of a 2-phenylphenol analyte.

To enhance reporter production, an amplification circuit was added to the bacterial sensor cells. HrpR and HrpS are transcriptional activators that form a hetero-hexameric complex to activate the hrpL promoter. An amplification circuit was generated using two plasmids. The first plasmid was derived from pBL_IMP_11 and contained the hrpR and hrpS genes downstream of the hbpC promoter, before the reporter gene (FIG. 1C, Table 1). The second plasmid contained the hrpR and hrpS genes and a reporter inserted downstream of the hrpL promoter. In the presence of 2-PP, HbpR protein was expressed from the first plasmid. HbpR protein bound to 2-PP and formed a HbpR/2-PP complex which complex bound to the hbpC promoter and induced expression of the hrpR and hrpS genes and the reporter gene from the hbpC promoter on the first plasmid. The HrpR and HrpS proteins expressed from the first plasmid associated into hetero-hexameric complexes that bound to the hrpL promoter of the second plasmid and induced expression of additional HrpR and HrpS proteins and reporter protein from the hrpL promoter (FIG. 1C). The reporter protein signal was amplified in this system by the expression of reporter protein from the first plasmid and HrpR/HrpS hetero-hexamer complex induced additional reporter protein expression from the second plasmid resulting in an up to 66-fold amplified reporter protein signal (FIG. 1D).

Inclusion of the amplification circuit resulted in an increase in reporter activity for all concentrations of 2-PP greater than 1 μM 2-PP. Increases in reporter gene expression ranged from 17 to 66-fold after three hours of incubation (FIG. 1D). For concentrations below 1 M, an increase in reporter protein production was not observed with the amplification circuit, suggesting the overall sensitivity was determined by HbpR. The amplification circuit led to a slight increase in background activity when compared to sensors lacking the circuit; however, the background activity was minimal compared to samples exposed to 2-PP.

Figure 3B:
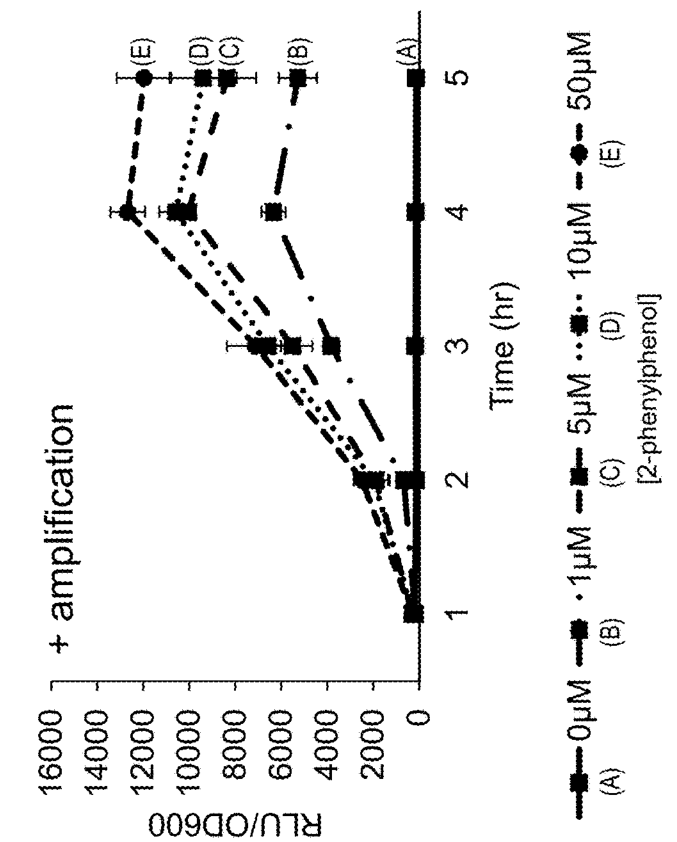
FIG. 3B shows lacZ reporter expression over time in bacterial sensor cells containing the pBL_IMP_32 and pBL_IMP_33 plasmids (+amplification) cultured in the presence of increasing concentrations of 2-phenlyphenol analyte.
Figure 3A:
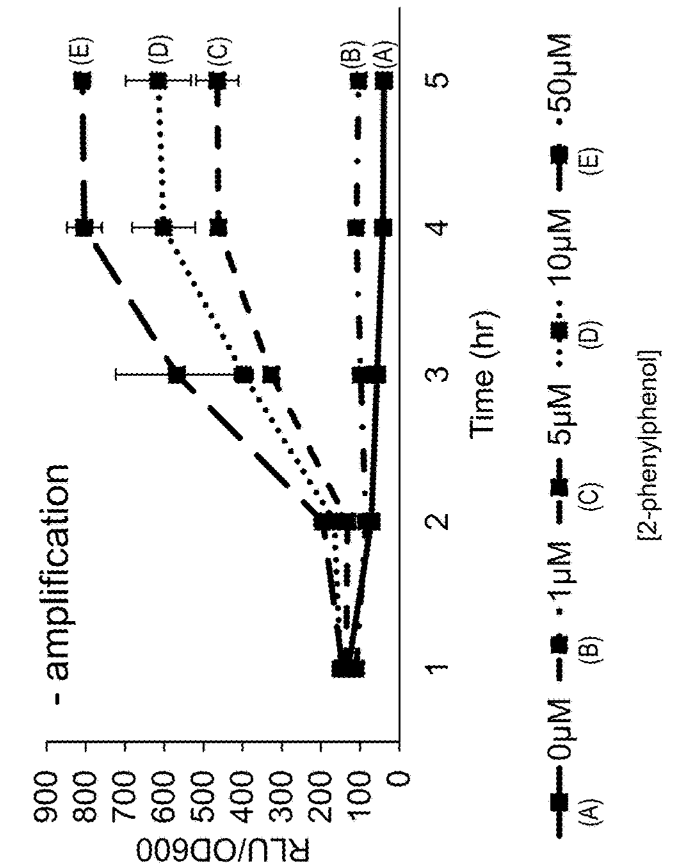
FIG. 3A shows lacZ reporter expression over time in bacterial sensor cells containing the pBL_IMP_11 plasmid (-amplification) cultured in the presence of increasing concentrations of 2-phenylphenol analyte.

In order to test the response of the reporter over time, the sensor strains were treated with various amounts of 2-PP and reporter activity was measured every hour for five hours. After two hours, there was an increase in reporter activity for the 5 μM, 10 μM, and 50 μM 2-PP treatments for strains that lacked an amplification circuit when compared to the 0 μM 2-PP control (FIG. 3A). For the strains with the amplification circuit, all of the 2-PP treatments showed an increase in reporter activity after two hours when compared to the 0 μM 2-PP control (FIG. 3B) Treatment with 1 μM 2-PP in the strain with the amplification circuit showed the highest fold-increase throughout the five-hour time course when compared to the same treatment in the strains without the amplification circuit. The 5 μM, 10 μM, and 50 μM 2-PP treatments showed similar fold-increases across the five-hour time course when compared to their respective strains without an amplification circuit. For both strains, the reporter activity continued to increase for four hours before plateauing. Addition of the amplification circuit did not seem to affect timing of the initial response of HbpR to 2-PP.

To demonstrate that this sensor strain could be used for visual detection without the use of any additional equipment, the lacZα gene in all plasmids was replaced with amilCP, a purple-blue chromoprotein from *Acropora millepora* (Table 1).

Figure 4A:
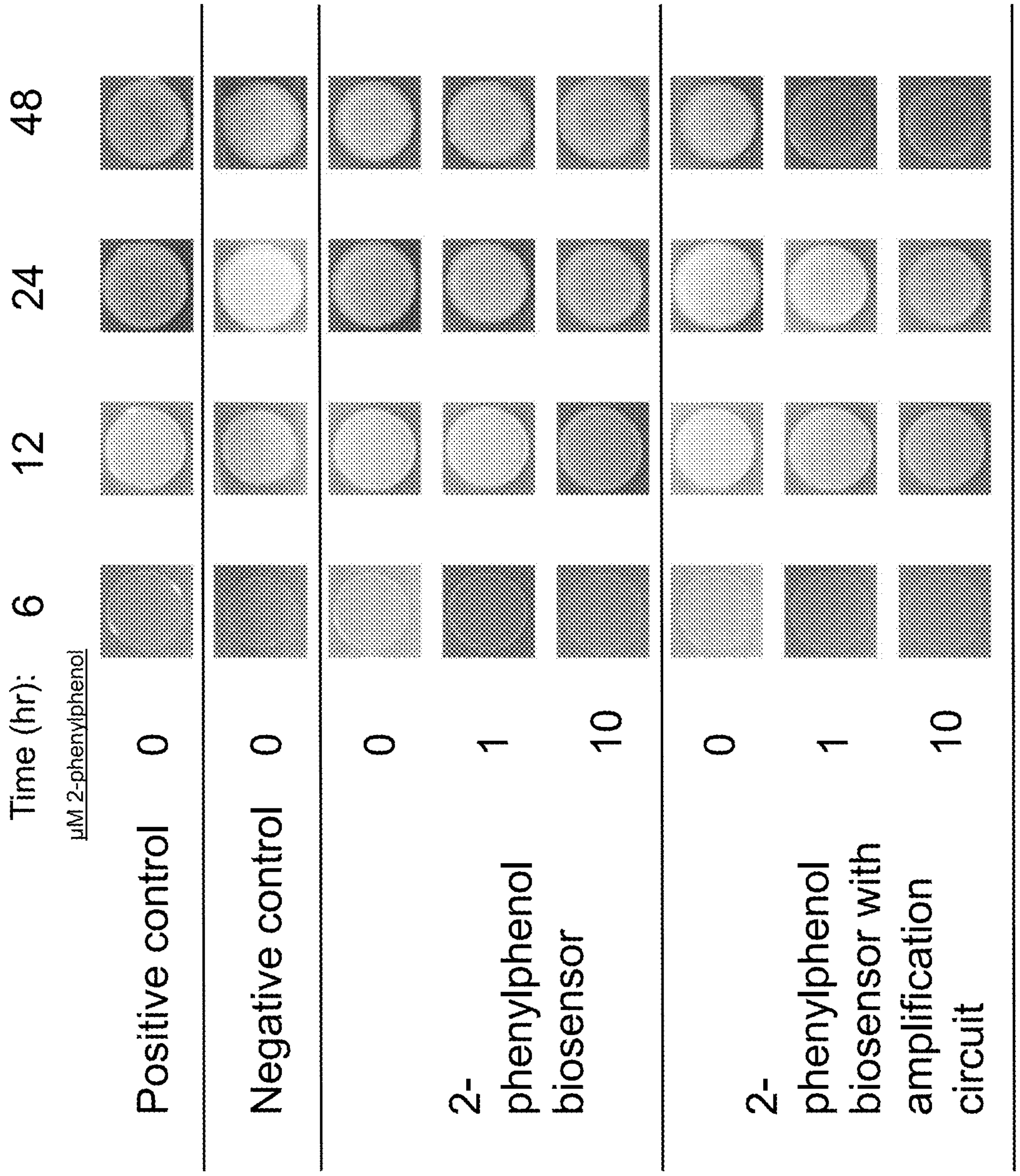
FIG. 4A shows photographs of agar plates with bacteria containing amilCP reporter-2-phenylphenol biosensors with (lower panels) or without (middle panels) an amplification circuit, grown for 6-48 hours in the presence of 0-10 μM 2-phenylphenol.

After 12-24 hours on agar plates containing 10 μM 2-phenylphenol, the strains with amplification circuit produced enough AmilCP purple reporter to become just barely visible. After 48 hours on agar plates containing 1 μM and 10 μM 2-phenylphenol, the AmilCP purple color became faintly visible in the strain without amplification circuit while strains with the amplification circuit produced a vibrant purple color (FIG. 4A, darker coloration versus lighter).

Figure 4B:
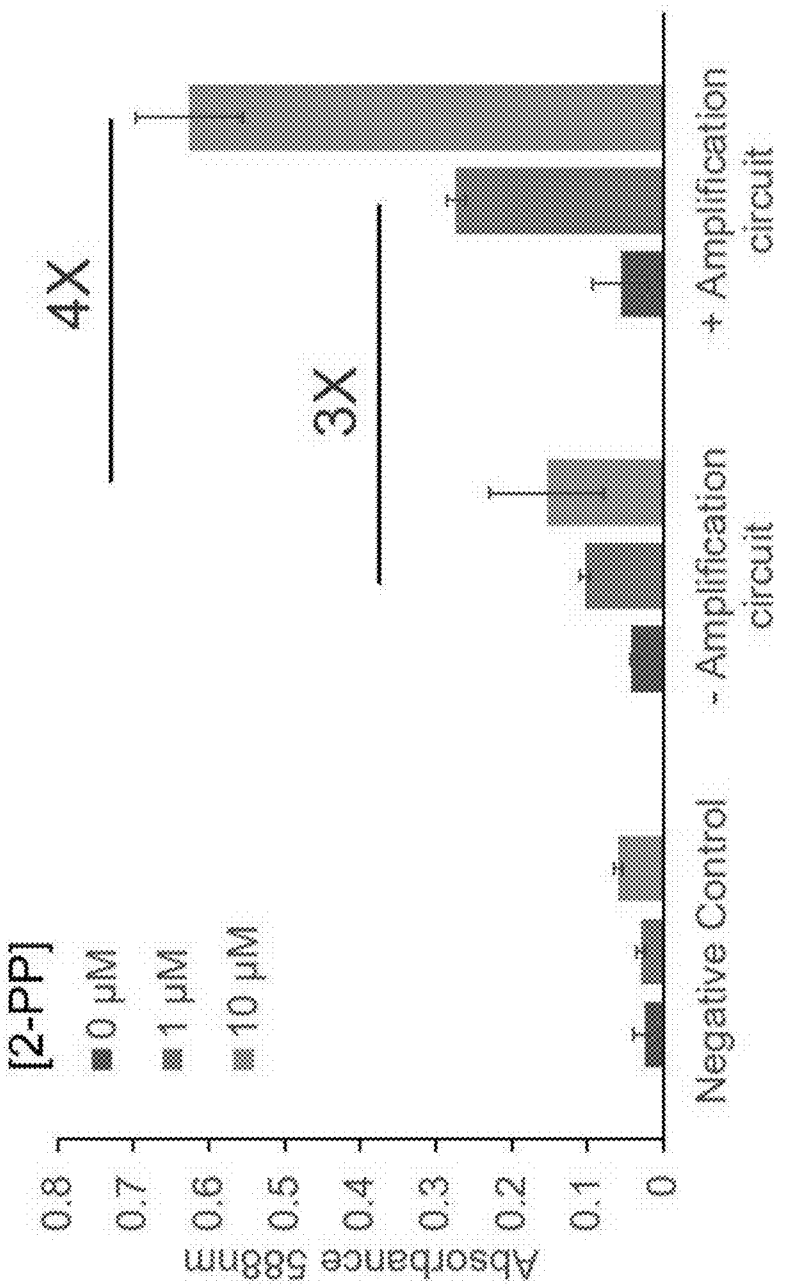
FIG. 4B shows amilC reporter expression in bacterial sensor cells with or without amplification circuit after 24 hours in the presence of 0, 1 μM, or 10 μM 2-phenylphenol (2-PP).
Figure 9:
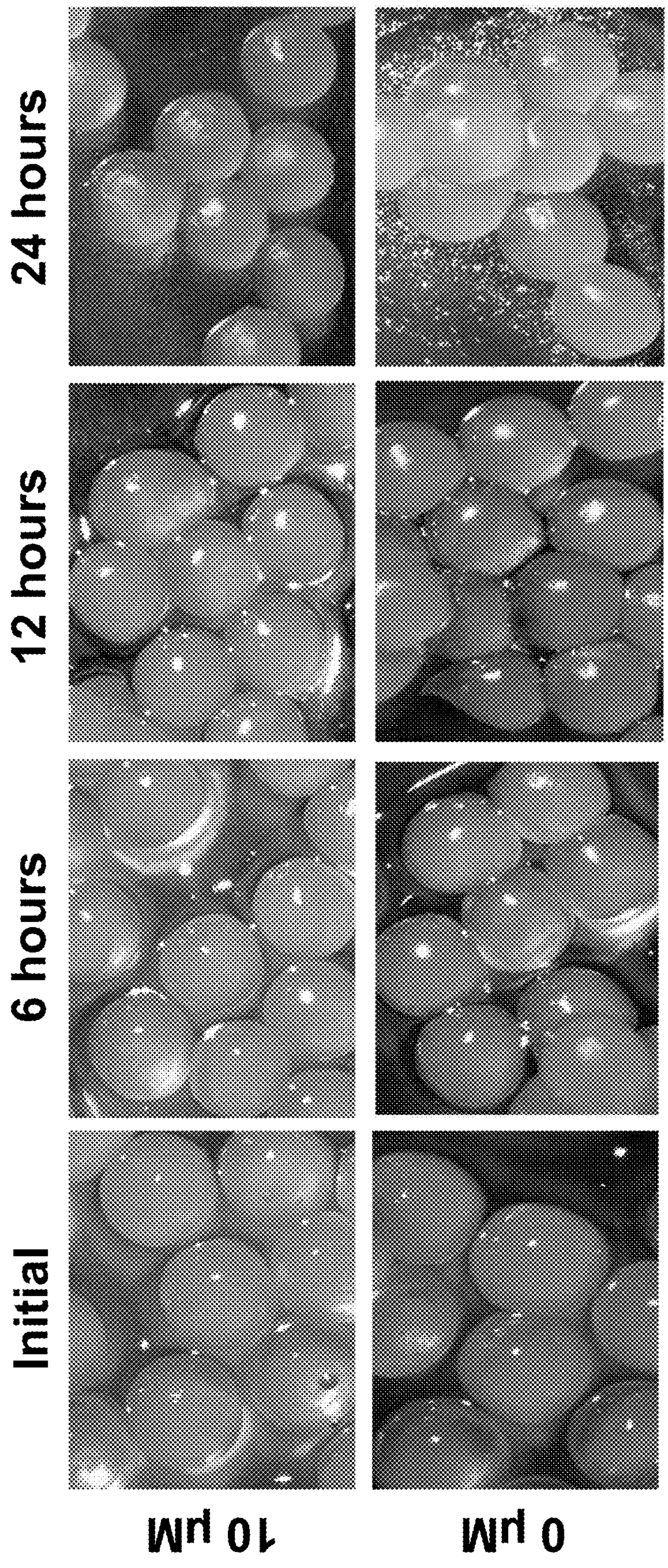
FIG. 9 shows photographs of microbeads containing bacterial sensor cells that express amilCP in the absence and presence of 10 μM 2-phenylphenol over a period of 24 hours.

Addition of the amplification circuit allowed for earlier detection of 2-PP by eye and produced a more vibrant color than strains without the amplification circuit as seen on agar plates as well as in liquid culture (FIG. 9). While the response time for the AmilCP reporter was slower than the 2 hour response time observed with the β-galactosidase reporter, use of the AmilCP reporter allowed for reporter visualization without additional equipment. When absorbance at 588 nm was used, addition of the amplification circuit in the AmilCP system allowed for detection of 2-PP at concentrations as low as 1 μM (FIG. 4B). The increase in reporter production through genetic amplification made it feasible for the living sensor to maintain a robust, visual reporter output when encapsulated.

Example 3—Signal Persistence

Figure 5A:
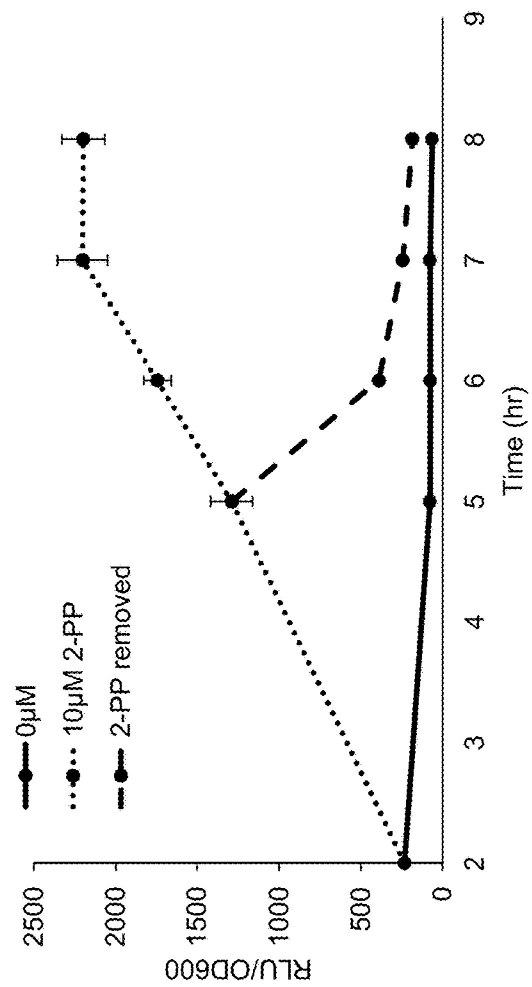
FIG. 5A shows lacZ reporter levels over time in bacterial sensor cells cultured in the presence of 0 and 10 μM 2-PP and upon removal of 2-PP after 5 hours of culture.
Figure 5B:
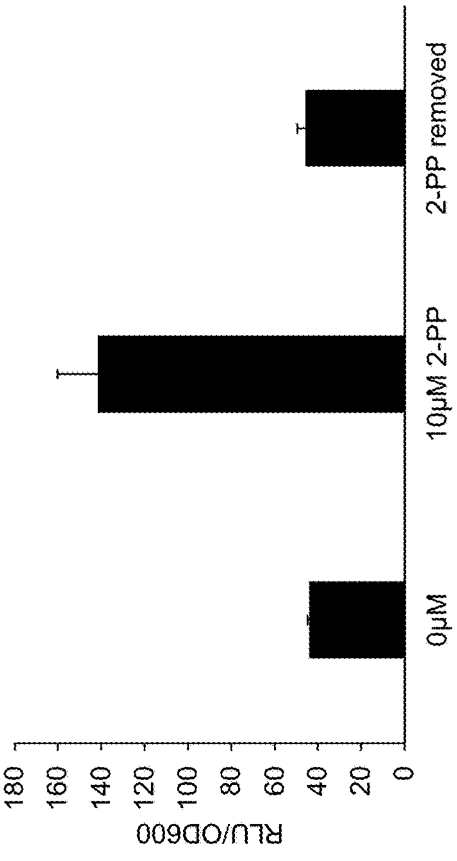
FIG. 5B shows lacZ reporter expression in bacterial sensor cells 24 hours after 2-PP removal.
Figure 5C:
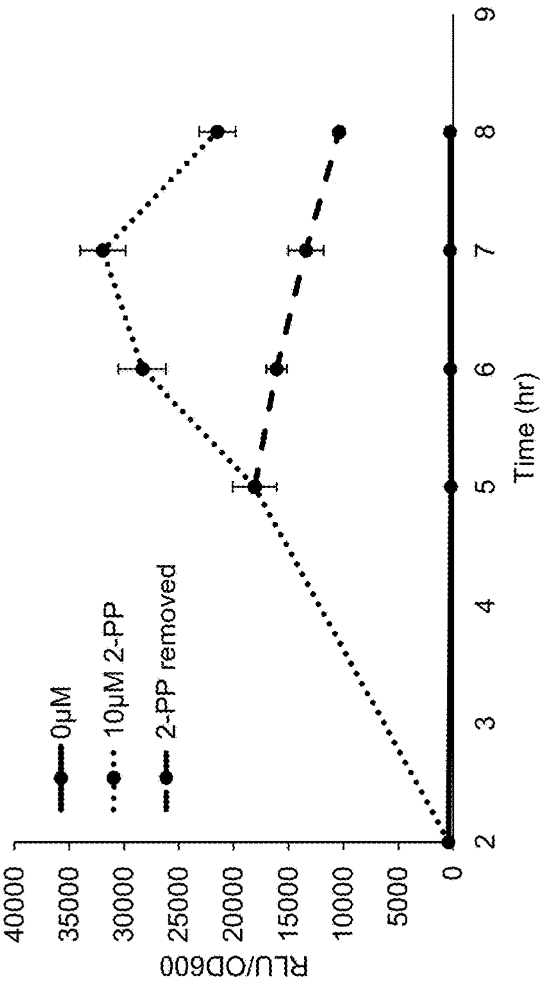
FIG. 5C shows lacZ reporter expression over time in bacterial sensor cells with amplification circuit cultured in the presence of 0 and 10 μM 2-PP and upon removal of 2-PP after 5 hours of culture.
Figure 5D:
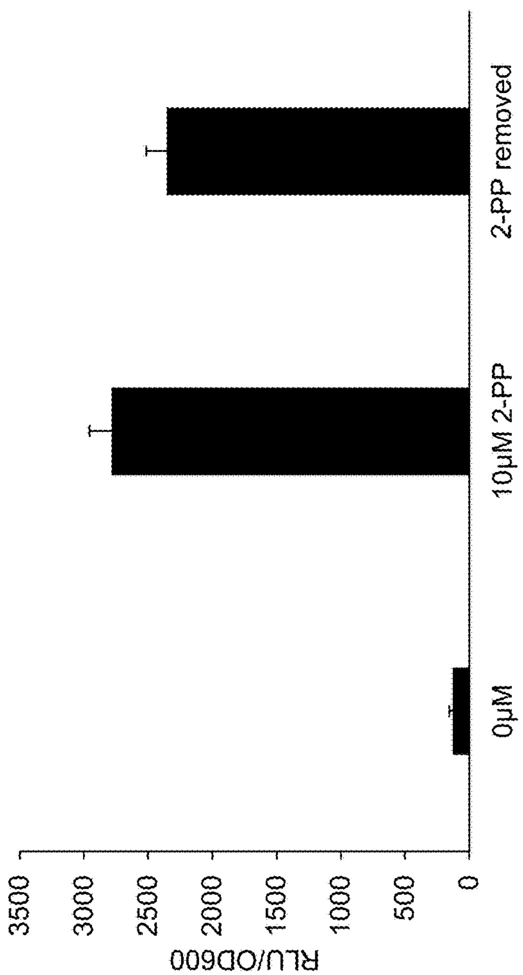
FIG. 5D shows lacZ reporter expression in bacterial sensor cells with amplification circuit 24 hours after 2-PP removal.

An important consideration when designing a living sensor is the persistence of the reporter output. In some use cases, it is desirable to have a living sensor that does not need to be exposed to the analyte of interest for an extended period for production of a detectable signal output. To determine the continuous production of the reporter with the addition of the amplification circuit, the sensor strain was exposed to the analyte for a limited period of time and then removed as described in the methods. For the strain without amplification circuit, (3-galactosidase reporter activity continued to increase for the samples that still contained 2-PP, whereas the strains where 2-PP was removed, the signal immediately began to decrease (FIG. 5A). After 24 hours, these samples had similar activity to the 0 μM control (FIG. 5B). For the strain with the amplification circuit, β-galactosidase reporter activity continued to increase for the samples that still contained 2-PP and then decreases at around t=7 hours (FIG. 5C). After 2-PP was removed from the cultures, the signal began to slowly decrease over time. After 24 hours, β-galactosidase activity was similar between the samples that had 2-PP and samples that removed the 2-PP (FIG. 5D.

These results are consistent with what was expected based on the reporter design. For the non-amplification strain, once the analyte is removed, there is nothing to drive expression from the hbpC promoter, so the signal will no longer increase and will eventually decrease depending on the stability of the reporter protein. For the amplification strain, after removing the analyte, the HrpR and HrpS proteins are still present to induce expression from the hrpL promoter and continue to produce more HrpR and HrpS proteins. This cycle should continue to produce reporter protein as long as the degradation of HrpR and HrpS is not faster than the production of the proteins in the amplification circuit. Addition of the amplification circuit to this living sensor adds stability and does not require constant analyte input to sustain activation of the amplification circuit.

Example 4—Validation of Hydrogel Formulation for Leakage Free Matrix

Figures 7A, 7B:
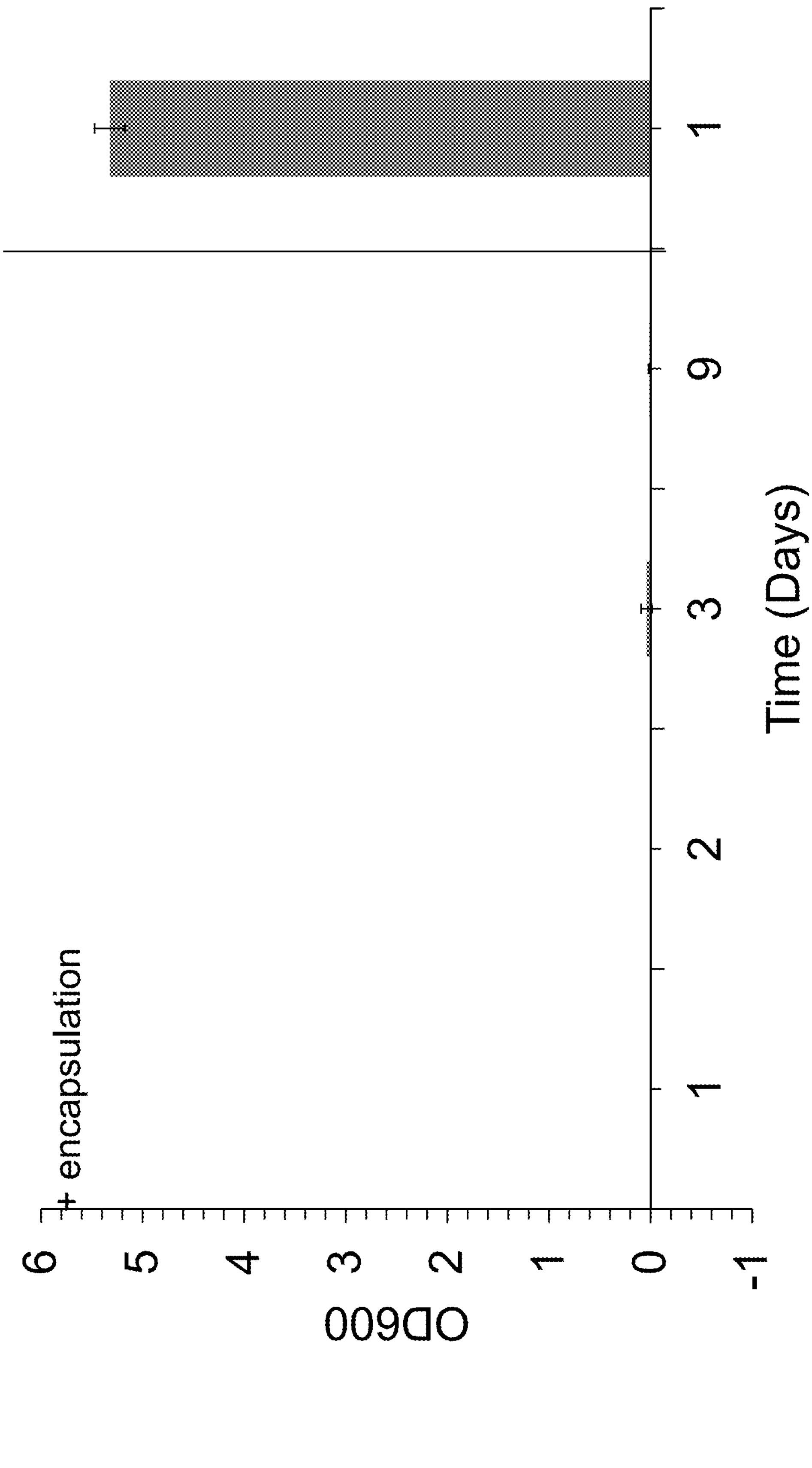
FIG. 7A shows the optical density of culture media surrounding bacterial sensor cells encapsulated in microbeads over a 9 day incubation period (+encapsulation).
FIG. 7B shows the optical density of culture media of bacterial sensor cells without microbead encapsulation.

With a robust, visual reporting sensing strain developed, a containment system for environmental delivery was necessary. A polyacrylamide-alginate (PAA) hydrogel was selected for cell compatibility. To validate that entrapment of the sensing strain cells in the semi-interpreting hydrogel network, microbeads containing sensing strain cells were incubated in salt free, Lysogeny Broth media at 30° C. The OD600 of the surrounding media was observed every 24 hours for a nine day incubation period. The OD600 remained zero for the duration of nine days indicating no cell leakage (FIG. 7A). If any cells were to have escaped the OD600 would have reached 3+ within 24 hours as observed with not encapsulated, cultured cells (FIG. 7B). These results suggest the PAA hydrogel has a pore size that remains small enough to entrap the sensing strain cells even when the hydrogel is in its swollen state.

Figure 8B:
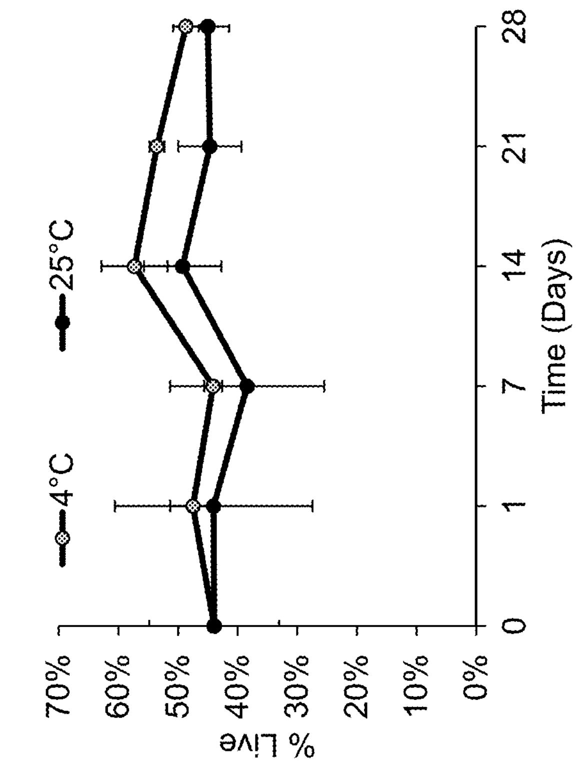
FIG. 8B shows a line graph of the percentage of live cells over a period of 28 day.
Figure 8A:
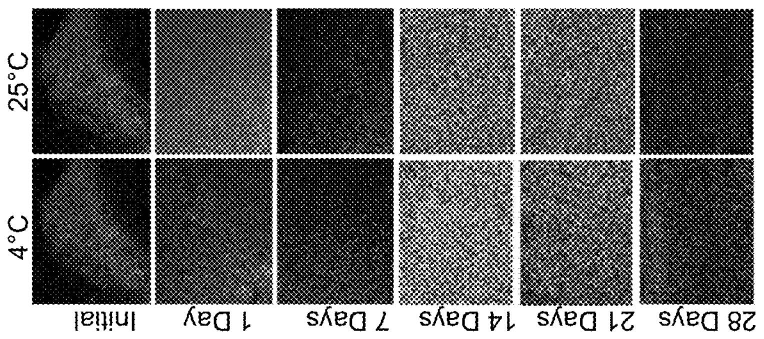
FIG. 8A shows confocal images of microbeads containing live, green fluorescent protein-expressing bacterial sensor cells after storage at 25° C. or 4° C. for up to 28 days.

Example 5—Characterization of Long-Term Microbial Cell Viability within Microbeads Long term viability of cells encapsulated in the PAA beads was evaluated in a series of live/dead assays on beads stored without additional nutrients at 25° C. and 4° C. over the course of one month. Confocal imaging of the beads showed the majority of cells are alive (green) after one month of storage at both temperatures (FIG. 8A). Quantitative analysis of the images illustrates that the relative percentage of live cells did not significantly change between storage conditions throughout the month ($p>0.05$) and remained stable over the month in both conditions (FIG. 8B). The initial viability of encapsulated cells starting at 43.9±0.1% could be attributed to cell death caused by the shear stress of extrusion and high density of cells in precursor solution during synthesis. However, the stability of relative % viability reflects that cells remain compatible with encapsulation material over the month storage time. While there was no significant change in viability over the month storage, the % live does slightly decrease at day 7 and then increase afterwards. The slight changes in viability can be attributed to the variability of cell dispersion between bead to bead in a batch. Overall, the quantitative and qualitative analysis of the live/dead confocal images confirm that the cells can survive up to a month in microbeads without additional nutrients.

Example 6—Characterization of Biosensors with Mutant HbpR Proteins

Figure 6A:
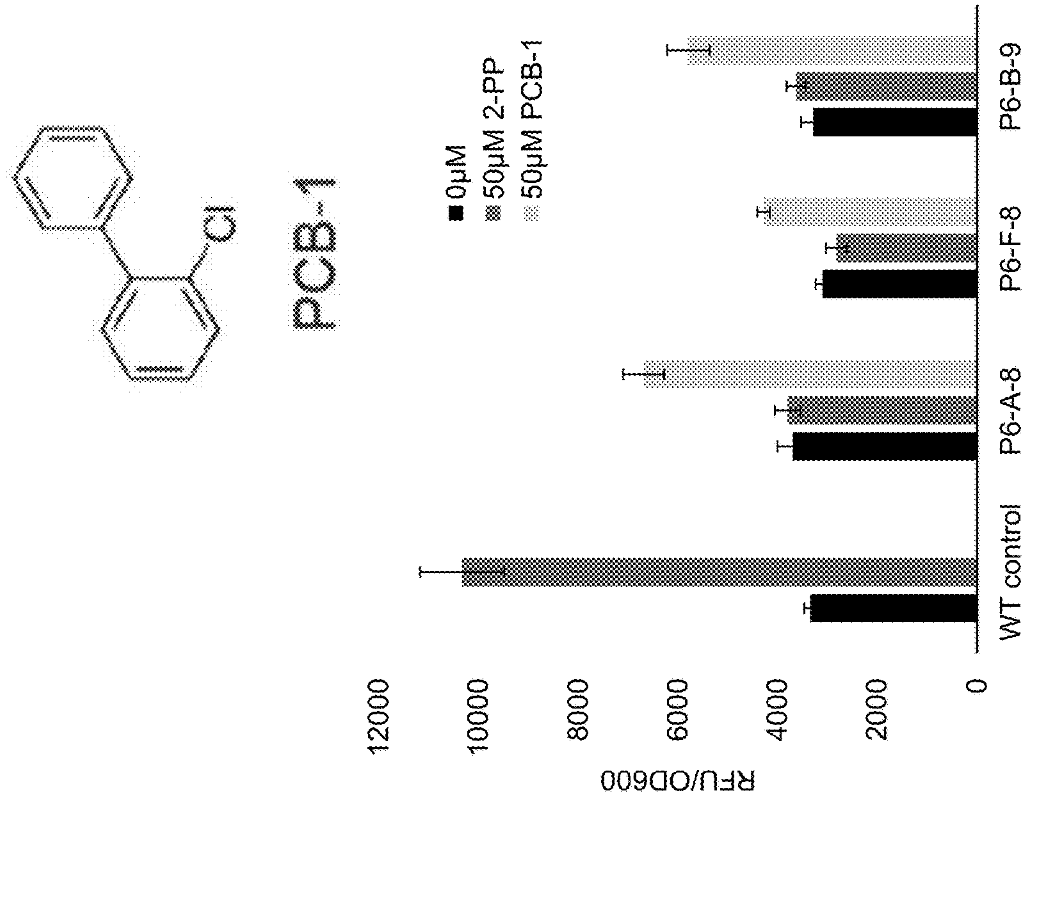
FIG. 6A shows lacZ reporter expression in bacterial sensor cells expressing different mutant HbpR proteins (P6-A-8, P6-F-8, P6-B9) cultured in the presence of 50 μM 2-PP or 50 μM PCB-1.
Figure 6B:
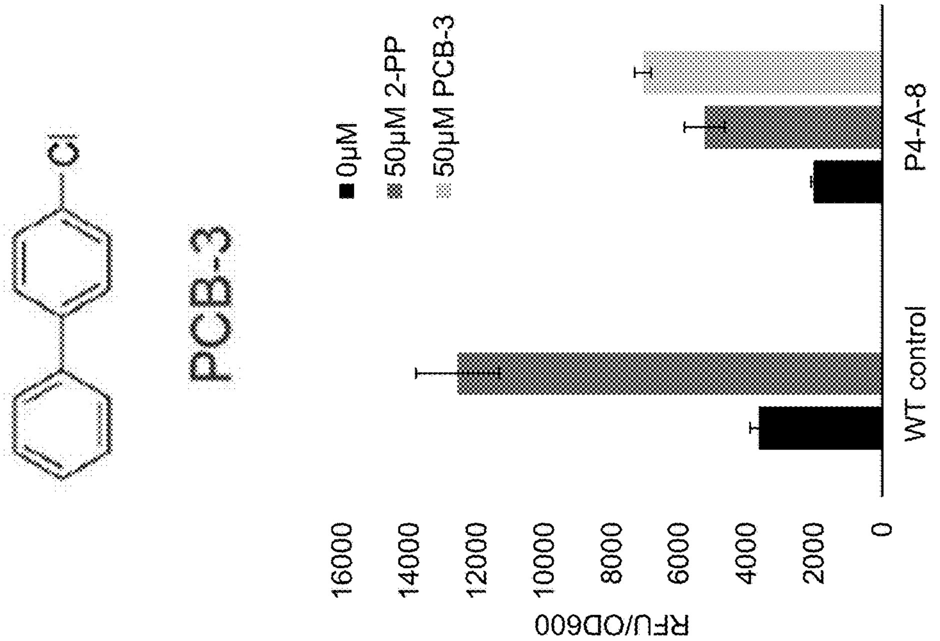
FIG. 6B shows lacZ reporter expression in bacterial sensor cells expressing a mutant HbpR proteins (P4-A-8) cultured in the presence of 50 μM 2-HBP or 50 μM PCB-3.

To generate biosensor systems that detect additional analytes, HbpR mutants were generated using a HbpR codon optimized library sequence (SEQ ID NO: 4) and a plasmid containing the same (SEQ ID NO: 8) and selection against different analytes. Mutant HbpR proteins that selectively bind analytes other than 2-PP were obtained through this process. For example, mutant HbpR proteins P6-A-8 (SEQ ID NO: 5), P6-F-8 (SEQ ID NO: 6), and P6-B-9 (SEQ ID NO: 7) showed selective lacZ reporter expression in the presence of polychlorinated biphenyl-1 (PCB-1) (FIG. 6A). And mutant HbpR protein P4-A-8 showed selective lacZ reporter expression in the presence of polychlorinated biphenyl-3 (PCB-3) (FIG. 6B). These data indicate the feasibility of preparing biosensor systems as described comprising polynucleotides encoding mutant HbpR proteins for the detection of various analytes.

Example 7—Induction of Encapsulated 2-Phenylphenol Whole Cell Biosensor

To demonstrate eBEADS can detect 2-phenylphenol at low concentrations, the sensor strain with amplification circuit was encapsulated and exposed to 0 to 10 μM 2-PP for 48 hours at 30° C. The encapsulated strain showed a purple color response within 24 hours of exposure to 10 μM 2-PP (FIG. 9, upper panels) compared to no color in the absence of 2-PP (FIG. 9, lower panels). After 48 hours, no response was observed in eBEADS that were exposed to less than 10 μM concentrations of 2PP. These results demonstrate that eBEADS can detect as little as 10 μM 2-PP and produce a robust visual response.

Example 8—Biosensor Systems with Hybrid Materials

To enhance mechanical stability of the biosensor systems described herein, polymer inorganic material hybrid nanoparticles were generated.

Figure 10A:
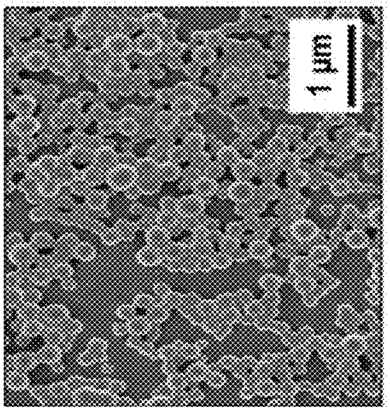
FIG. 10A shows electron microscopy images of polymeric nanoparticles.
Figure 10B:
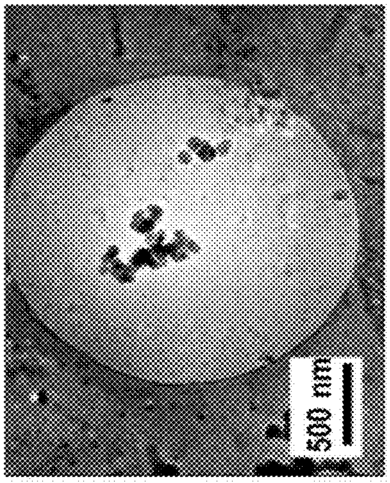
FIG. 10B shows electron microscopy images of lipid nanoparticles.
Figure 10C:
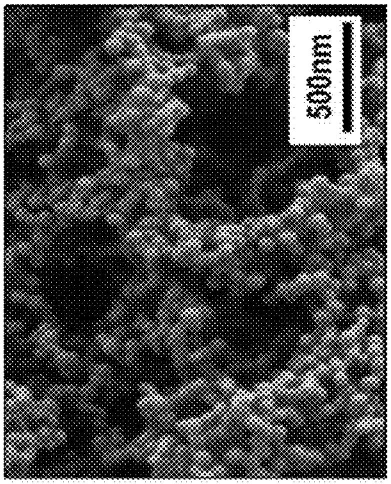
FIG. 10C shows electron microscopy images of mesoporous silica nanoparticles.
Figure 11A:
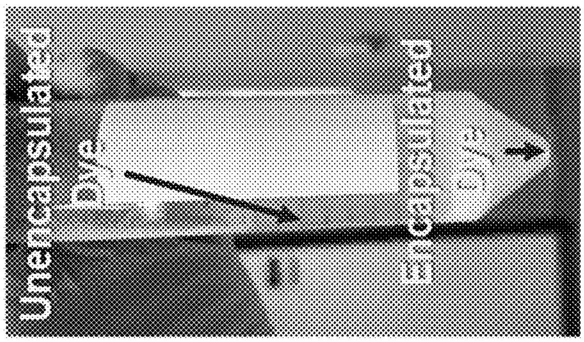
FIG. 11A shows a photograph of a tube containing inorganic nanoparticles encapsulating photochromic dye and unencapsulated dye present in the medium.
Figure 11B:
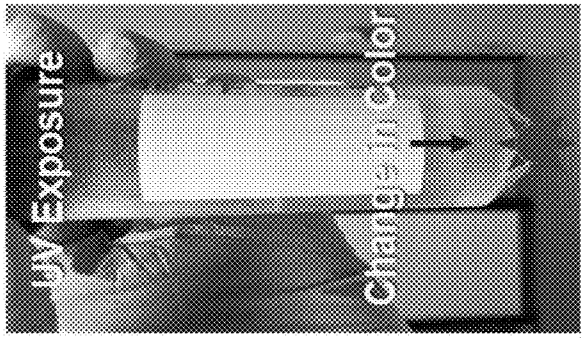
FIG. 11B shows a photograph of a tube containing inorganic nanoparticles following UV exposure of the bottom of the tube (star).
Figure 11C:
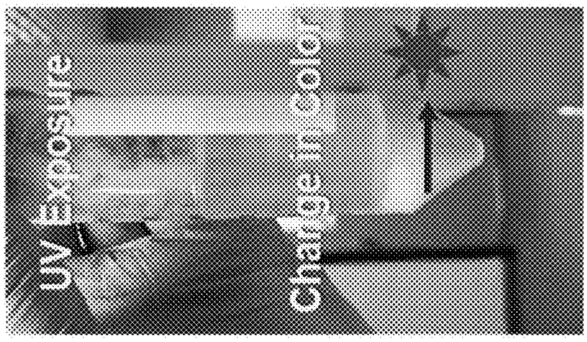
FIG. 11C shows a photograph of a tube containing inorganic nanoparticles following UV exposure of the right side of the tube (star).
Figure 12:
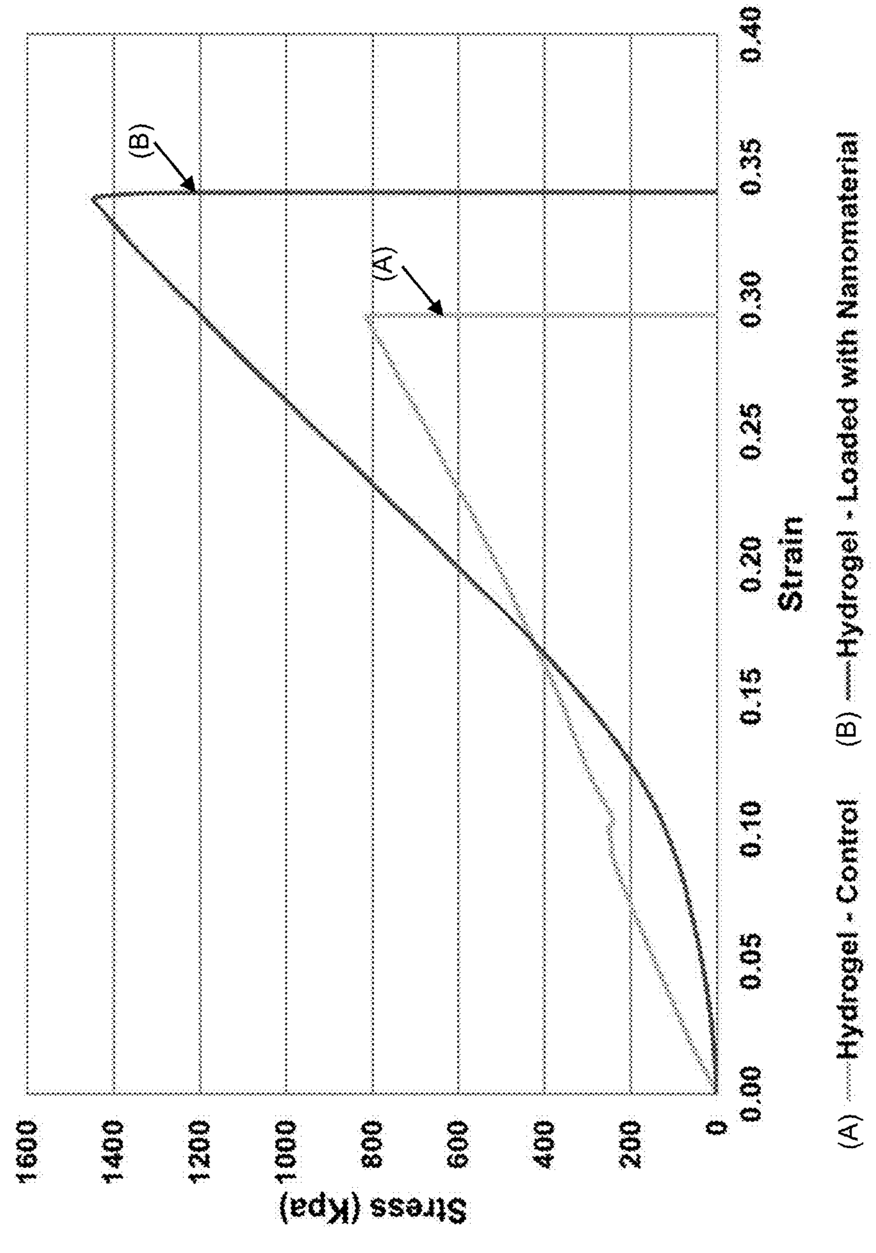
FIG. 12 shows a stress-strain curve of an inorganic nanomaterial reinforced hybrid hydrogel system.

To this end, hydrogels were loaded with an inorganic reinforcement material. Electron microscopy images of polymeric, lipid, and mesoporous silica nanoparticles are shown in FIG. 10. Encapsulation of a photochromic dye into hybrid nanoparticles reinforced with inorganic reinforcement material showed effective dye encapsulation (FIG. 11A) and a color change upon exposure of the nanoparticles to UV light (FIGS. 11B and 11C). The reinforced hybrid nanoparticles showed some difference on the stress-strain curves (particularly at lower strain) when a small concentration of an inorganic reinforcement material (i.e., 1 mg/mL) was added (FIG. 12). The use of inorganic reinforcement materials in eBEADS results in robust sensing systems that support cell viability. Such hybrid material systems possess the desirable features of both inorganic and organic systems.

CONCLUSION eBEADS is an extensible system for deploying whole-cell living sensors with no need for equipment. The engineered living sensor utilizes the HbpR transcriptional activator and an amplification circuit to detect as little as 1 μM 2-PP. This whole-cell living sensor produces a long-lasting amplified signal up to 66 times with minimal background. The signal amplification allows a timely and clear visual response, which is vital for in field readouts. Physical biocontainment and long-term viability of whole-cell living sensors in PAA microbeads was demonstrated. eBEADS is an end-to-end living sensor for the zero-power detection of 2-PP in the environment. This system serves as a tailorable platform to detect additional environmental pollutants and enables new sensor form factors to support applications like remote deployment or wearables.

What is claimed is:

1. A polynucleotide comprising a *Pseudomonas azelaica* hbpR (hbpR) promoter operably linked to a polynucleotide encoding a HbpR protein, a *Psuedomonas azelaica* hbpC promoter operably linked to a polynucleotide encoding a marker protein, wherein the marker protein creates a visible output signal, and an amplification cassette comprising: a polynucleotide encoding a *Pseudomonas syringae* hrpR (HrpR) protein that is operably linked to the hbpC promoter and a polynucleotide encoding a *Pseudomonas syringae* hrpS (HrpS) protein downstream of the polynucleotide encoding the HrpR protein, wherein the amplification cassette does not comprise a *P. syringae* hrpL promoter.

2. The polynucleotide of claim 1, wherein the hbpR promoter and the *Pseudomonas azelaica* hbpC promoter promote transcription in opposite directions.

3. The polynucleotide of claim 1, further comprising:

a. a promoter operably linked to a polynucleotide encoding a HrpR protein, a polynucleotide encoding a HrpS protein, and a polynucleotide encoding the marker protein; or b. a promoter operably linked to a polynucleotide encoding a HrpS protein, a polynucleotide encoding a HrpR protein, and a polynucleotide encoding the marker protein.

4. The polynucleotide of claim 1, wherein the HbpR protein encoded by the polynucleotide binds an analyte of interest.

5. The polynucleotide of claim 4, wherein the analyte of interest is a polyphenyl selected from the group consisting of 2-hydroxybiphenyl, 2,2'-dihydroxybiphenyl, 2-aminobiphenyl, and 2-hydroxybiphenylmethane.

6. The polynucleotide of claim 1, wherein the polynucleotide encoding the HbpR protein comprises at least one mutation compared to a polynucleotide encoding a wild-type HbpR protein.

7. The polynucleotide of claim 6, wherein the HbpR protein that comprises the at least one mutation binds a different analyte of interest than a wild-type HbpR protein.

8. The polynucleotide of claim 7, wherein the different analyte of interest is a polychlorinated polyphenyl.

9. The polynucleotide of claim 1, wherein the marker protein is an amilCP protein.

10. A biocontainment material for containment and maintenance of a microbe comprising a polynucleotide according to claim 1, the biocontainment material comprising a polymer-based hydrogel, a multi-layer hydrogel comprising a hydrogel and an elastomer outer layer, or a polymer-inorganic material hybrid hydrogel.

11. The biocontainment material of claim 10, wherein the polymer-based hydrogel comprises polyacrylamide alginate, chitosan, agarose, agar, gelatin, or pullulan.

12. The biocontainment material of claim 11, wherein the polyacrylamide alginate comprises alginate and polyacrylamide at a ratio of alginate to polyacrylamide of about 1:50.

13. The biocontainment material of claim 10, wherein the elastomer outer layer of the multi-layer hydrogel comprises a polyurethane skin.

14. The biocontainment material of claim 10, wherein the polymer-inorganic material hybrid hydrogel comprises alginate polyacrylamide and polycaprolactone.

15. A whole cell biosensor comprising the polynucleotide of claim 1.

16. The whole cell biosensor of claim 15, further comprising a second polynucleotide comprising:

a. a promoter operably linked to a polynucleotide encoding a HrpR protein, a polynucleotide encoding a HrpS protein, and a polynucleotide encoding the marker protein; or b. a promoter operably linked to a polynucleotide encoding a HrpS protein, a polynucleotide encoding a HrpR protein, and a polynucleotide encoding the marker protein.

* * * * *

SEQUENCE LISTING

```
Sequence total quantity: 15
SEQ ID NO: 1            moltype = DNA  length = 654
FEATURE                 Location/Qualifiers
source                  1..654
                        mol_type = other DNA
                        note = HbpR promoter
                        organism = Pseudomonas azelaica
SEQUENCE: 1
tgttatcacg tctccgcgtt catattgttt taataggcag cagtacagtc gaactcacgg  60
ctgccttgcg ggactcgtag ccagtaccgt gccaggttga ctaagcagcc tcagacataa  120
aagctaggat actgttttat aaggattttt attttaatga gcgccagaaa gcctagctcc  180
agacggctgt aaaccccttc cgcggtcgcc aacagctgcc gaaatgcact tgccatggcg  240
ggcaagcttc accatattat gaaaactcac aaccacgatt tcataaattt attaaatcta  300
cgagaaccct atctactcct acctggcatg agctatcacc atgaaatcta acaaaaataa  360
gaaccatgaa aaccgcacca tcgttgccga tctatcgcgc cctgaaatcc atgtttcggc  420
gttcggtctg cattccctcc ccacaacgaa ggacgcatct ggctaggcga cagcccgatc  480
catgcaccta cacacagtaa gactgaaggg aatatggatc cgtcggcaga tgccagaatg  540
cgcctgctcg gacgagctgg tttcaccata ttctgaatcc caccaccaca atttaataaa  600
attattaaac ccaacgagac cctcatctat tcctaccgga cctgaaccat cgcc        654

SEQ ID NO: 2            moltype = DNA  length = 654
FEATURE                 Location/Qualifiers
source                  1..654
                        mol_type = other DNA
                        note = HbpC promoter
                        organism = Pseudomonas azelaica
SEQUENCE: 2
ggcgatggtt caggtccggt aggaatagat gagggtctcg ttgggtttaa taattttatt  60
aaattgtggt ggtgggattc agaatatggt gaaaccagct cgtccgagca ggcgcattct  120
ggcatctgcc gacggatcca tattcccttc agtcttactg tgtgtaggtg catggatcgg  180
gctgtcgcct agccagatgc gtccttcgtt gtggggaggg aatgcagacc gaacgccgaa  240
acatggattt cagggcgcga tagatcggca acgatggtgc ggttttcatg gttcttattt  300
ttgttagatt tcatggtgat agctcatgcc aggtaggagt agatagggtt ctcgtagatt  360
taataaattt atgaaatcgt ggttgtgagt tttcataata tggtgaagct tgcccgccat  420
ggcaagtgca tttcggcagc tgttggcgac cgcggaaggg gtttacagcc gtctggagct  480
aggctttctg gcgctcatta aaataaaaat ccttataaaa cagtatccta gcttttatgt  540
ctgaggctgc ttagtcaacc tggcacggta ctggctacga gtcccgcaag gcagccgtga  600
gttcgactgt actgctgcct attaaaacaa tatgaacgcg gagacgtgat aaca        654

SEQ ID NO: 3            moltype = DNA  length = 237
FEATURE                 Location/Qualifiers
source                  1..237
                        mol_type = other DNA
                        note = HrpL promoter
                        organism = Pseudomonas syringae
SEQUENCE: 3
gccggattat gtccgctgag tgggtcacgg tcccggatca gttcccttgc gaagctgacc  60
gatgtttttg tgccaaaagc tgttgtggca aaaaacggtt tgcgcaaagt tttgtattac  120
aaagaatttc acattttaaa atatctttat aaatcaatca gttatttcta tttttaagct  180
ggcatggtta tcgctatagg gcttgtacta ctagagatta aagaggagaa atactag     237

SEQ ID NO: 4            moltype = DNA  length = 1746
FEATURE                 Location/Qualifiers
source                  1..1746
                        mol_type = other DNA
                        organism = Pseudomonas azelaica
variation               1..1746
                        note = where NNK indicates a site to be mutated
SEQUENCE: 4
atggaacaga agcttatatc ggaggaagat ctcatgaaat caaataaaaa taatagcgac  60
gatcgcagca ttgtggcgga tctggcgctg ccggaagtgc atgcgctggt gagtaaactg  120
cattttagcc cgaatgaagg ccgtatttgg ctggatgaaa gccgttgcct gctgctgcag  180
gtggaaaccc tgaaagatat ttataaagaa ctgcaggcgt atagcggccc agattatacc  240
cgtgagtttc tgacccgtat tggctttacc accggccagc gtgatgcgga aatgattatc  300
aaaaaacaag gcattagcag cattaaggaa cagnnktatg caggtggtgt gctgcatgcc  360
ctgcagggct ttctgaccag cattcaggcg ggcagcagcg cgctgaatgc ggtggatatg  420
aaaagcatgg atnnkcatnn kgaggcatac tggcagaata gcattgaagc ggaaattcat  480
ctggcgatgc atggcgtgag cagccatgcg gtgtgctggt ttagcgtggc gtatnnktca  540
gggtacnnka gcgcgtgcgc gggcaaaccg attgtggtgg aagaaattga atgccaggcg  600
atgggccata cccattgccg tnnkcaannk aaaccggcgg aaatgtgggc gctgagccag  660
agcgaacaga gccagattac cacccatcct attcccgatg atgatcaggg cggcgagctc  720
gtcattggtt cgtcggcagt gttcaaggtg ctccgtcaca aaacagcctg tgtggcagag  780
actgatgcga ctgttctttt acttggagaa agtgggagcg gcaagagcct tattgcacgc  840
gagatccacc gtttgagcaa ccgcgccgac caagctttcg tcgaagtgaa ctgtgccgct  900
atacccgatc aattaatcga gtcggagctg ttcggcgtag agcgcggagc ctttacaggt  960
gcgaccgcta cgcgagaggg gcgtttcgag gcggctcatc aaggcactct cttccttgac  1020
gaaattgcca ccctcagtat gaccgctcaa agtaaacttc tccgtgtatt gcagaatggc  1080
gaattggaac gtctcggtag caaccggaca atccacacca gtgtccgact gattgccgcc  1140
```

```
acgaacgctg atctgaaaaa agctgtccaa gatggtcact tccgagagga tctttactat  1200
cgactgaacg tctttcccat ccagattccc cctctgcgag aacgccgcga tgatatttca  1260
ctcattacca gcgtactcat cgctcgattt tctaaacgcc acggacgtaa gttaaaaggc  1320
atatcgtctg ccgccatgca ggtacttatc taccatgact ggccaggcaa tattcgagaa  1380
ttggagaacg tgattgagag agccataatc atggctcaag acgtcgattt tttggacacc  1440
caccatttaa cgacaattga aggcaccctc actacacaag acttcctgag tcttaaccag  1500
aaaggtgatt tgaccttgag cagcgagcta atacggaacg cggctgagaa cgccaaccct  1560
aaagttctct cattagatga gtttgccgag cagatggtgc atcaagggtc tattaacctg  1620
gaccaggttc aagacgccat cacccgagca gctgtcaaac atagcggtgg caatatttcc  1680
cgggcggcct cccttcttgg gataactcga gcccggcttg attaccgcgt caaaaagatc  1740
acatag                                                             1746

SEQ ID NO: 5            moltype = DNA  length = 1746
FEATURE                 Location/Qualifiers
source                  1..1746
                        mol_type = other DNA
                        note = P6-A-8
                        organism = Pseudomonas azelaica
SEQUENCE: 5
atggaacaga agcttatatc ggaggaagat ctcatgaaat caaataaaaa taatagcgac  60
gatcgcagca ttgtggcgga tctggcgctg ccggaagtgc atgcgctggt gagtaaactg  120
cattttagcc cgaatgaagg ccgtatttgg ctggatgaaa gccgttgcct gctgctgcag  180
gtggaaaccc tgaaagatat ttataaagaa ctgcaggcgt atagcggccc agattatacc  240
cgtgagtttc tgacccgtat tggctttacc accggccagc gtgatgcgga aatgattatc  300
aaaaaacaag gcattagcag cattaaggaa cagtcgtatg caggtggtgt gctgcatgcc  360
ctgcagggct ttctgaccag cattcaggcg ggcagcagcg cgctgaatgc ggtggatatg  420
aaaagcatgg atttgcatgc tgaggcatac tggcagaata gcattgaagc ggaaattcat  480
ctggcgatgc atggcgtgag cagccatgcg gtgtgctggt ttagcgtggc gtataggtca  540
gggtacccga gcgcgtgcgc gggcaaaccg attgtggtgg aagaaattga atgccaggcg  600
atgggccata cccattgccg tacgcaatct aaaccggcgg aaatgtgggc gctgagccag  660
agcgaacaga gccagattac cacccatcct attcccgatg atgatcaggg cggcgagctc  720
gtcattggtt cgtcggcagt gttcaaggtg ctccgtcaca aaacagcctg tgtggcagag  780
actgatgcga ctgttctttt acttggagaa agtgggagcg gcaagagcct tattgcacgc  840
gagatccacc gtttgagcaa ccgcgccgac caagctttcg tcgaagtgaa ctgtgccgct  900
atacccgatc aattaatcga gtcggagctg ttcggcgtag agcgcggagc ctttacaggt  960
gcgaccgcta cgcgagaggg gcgtttcgag gcggctcatc aaggcactct cttccttgac  1020
gaaattgcca ccctcagtat gaccgctcaa agtaaacttc tccgtgtatt gcagaatggc  1080
gaattggaac gtctcggtag caaccggaca atccacacca gtgtccgact gattgccgcc  1140
acgaacgctg atctgaaaaa agctgtccaa gatggtcact tccgagagga tctttactat  1200
cgactgaacg tctttcccat ccagattccc cctctgcgag aacgccgcga tgatatttca  1260
ctcattacca gcgtactcat cgctcgattt tctaaacgcc acggacgtaa gttaaaaggc  1320
atatcgtctg ccgccatgca ggtacttatc taccatgact ggccaggcaa tattcgagaa  1380
ttggagaacg tgattgagag agccataatc atggctcaag acgtcgattt tttggacacc  1440
caccatttaa cgacaattga aggcaccctc actacacaag acttcctgag tcttaaccag  1500
aaaggtgatt tgaccttgag cagcgagcta atacggaacg cggctgagaa cgccaaccct  1560
aaagttctct cattagatga gtttgccgag cagatggtgc atcaagggtc tattaacctg  1620
gaccaggttc aagacgccat cacccgagca gctgtcaaac atagcggtgg caatatttcc  1680
cgggcggcct cccttcttgg gataactcga gcccggcttg attaccgcgt caaaaagatc  1740
acatag                                                             1746

SEQ ID NO: 6            moltype = DNA  length = 1746
FEATURE                 Location/Qualifiers
source                  1..1746
                        mol_type = other DNA
                        note = P6-F-8
                        organism = Pseudomonas azelaica
SEQUENCE: 6
atggaacaga agcttatatc ggaggaagat ctcatgaaat caaataaaaa taatagcgac  60
gatcgcagca ttgtggcgga tctggcgctg ccggaagtgc atgcgctggt gagtaaactg  120
cattttagcc cgaatgaagg ccgtatttgg ctggatgaaa gccgttgcct gctgctgcag  180
gtggaaaccc tgaaagatat ttataaagaa ctgcaggcgt atagcggccc agattatacc  240
cgtgagtttc tgacccgtat tggctttacc accggccagc gtgatgcgga aatgattatc  300
aaaaaacaag gcattagcag cattaaggaa cagtattatg caggtggtgt gctgcatgcc  360
ctgcagggct ttctgaccag cattcaggcg ggcagcagcg cgctgaatgc ggtggatatg  420
aaaagcatgg ataagcatac ggaggcatac tggcagaata gcattgaagc ggaaattcat  480
ctggcgatgc atggcgtgag cagccatgcg gtgtgctggt ttagcgtggc gtatgagtca  540
gggtacctta gcgcgtgcgc gggcaaaccg attgtggtgg aagaaattga atgccaggcg  600
atgggccata cccattgccg tatgcaacgg aaaccggcgg aaatgtgggc gctgagccag  660
agcgaacaga gccagattac cacccatcct attcccgatg atgatcaggg cggcgagctc  720
gtcattggtt cgtcggcagt gttcaaggtg ctccgtcaca aaacagcctg tgtggcagag  780
actgatgcga ctgttctttt acttggagaa agtgggagcg gcaagagcct tattgcacgc  840
gagatccacc gtttgagcaa ccgcgccgac caagctttcg tcgaagtgaa ctgtgccgct  900
atacccgatc aattaatcga gtcggagctg ttcggcgtag agcgcggagc ctttacaggt  960
gcgaccgcta cgcgagaggg gcgtttcgag gcggctcatc aaggcactct cttccttgac  1020
gaaattgcca ccctcagtat gaccgctcaa agtaaacttc tccgtgtatt gcagaatggc  1080
gaattggaac gtctcggtag caaccggaca atccacacca gtgtccgact gattgccgcc  1140
acgaacgctg atctgaaaaa agctgtccaa gatggtcact tccgagagga tctttactat  1200
cgactgaacg tctttcccat ccagattccc cctctgcgag aacgccgcga tgatatttca  1260
ctcattacca gcgtactcat cgctcgattt tctaaacgcc acggacgtaa gttaaaaggc  1320
```

```
atatcgtctg ccgccatgca ggtacttatc taccatgact ggccaggcaa tattcgagaa  1380
ttggagaacg tgattgagag agccataatc atggctcaag acgtcgattt tttggacacc  1440
caccatttaa cgacaattga aggcaccctc actacacaag acttcctgag tcttaaccag  1500
aaaggtgatt tgaccttgag cagcgagcta atacggaacg cggctgagaa cgccaaccct  1560
aaagttctct cattagatga gtttgccgag cagatggtgc atcaagggtc tattaacctg  1620
gaccaggttc aagacgccat cacccgagca gctgtcaaac atagcggtgg caatatttcc  1680
cgggcggcct cccttcttgg gataactcga gcccggcttg attaccgcgt caaaaagatc  1740
acatag                                                             1746

SEQ ID NO: 7           moltype = DNA  length = 1746
FEATURE                Location/Qualifiers
source                 1..1746
                       mol_type = other DNA
                       note = P6-B-9
                       organism = Pseudomonas azelaica
SEQUENCE: 7
atggaacaga agcttatatc ggaggaagat ctcatgaaat caaataaaaa taatagcgac  60
gatcgcagca ttgtggcgga tctggcgctg ccggaagtgc atgcgctggt gagtaaactg  120
cattttagcc cgaatgaagg ccgtatttgg ctggatgaaa gccgttgcct gctgctgcag  180
gtggaaaccc tgaaagatat ttataaagaa ctgcaggcgt atagcggccc agattatacc  240
cgtgagtttc tgacccgtat tggctttacc accggccagc gtgatgcgga aatgattatc  300
aaaaaacaag gcattagcag cattaaggaa cagggttatg caggtggtgt gctgcatgcc  360
ctgcagggct ttctgaccag cattcaggcg ggcagcagcg cgctgaatgc ggtggatatg  420
aaaagcatgg atactcattg tgaggcatac tggcagaata gcattgaagc ggaaattcat  480
ctggcgatgc atggcgtgag cagccatgcg gtgtgctggt ttagcgtggc gtatgtgtca  540
gggtacgcga gcgcgtgcgc gggcaaaccg attgtggtgg aagaaattga atgccaggcg  600
atgggccata cccattgccg tcctcaacgt aaaccggcgg aaatgtgggc gctgagccag  660
agcgaacaga gccagattac cacccatcct attcccgatg atgatcaggg cggcgagctc  720
gtcattggtt cgtcggcagt gttcaaggtg ctccgtcaca aaacagcctg tgtggcagag  780
actgatgcga ctgttctttt acttggagaa agtgggagcg gcaagagcct tattgcacgc  840
gagatccacc gtttgagcaa ccgcgccgac caagctttcg tcgaagtgaa ctgtgccgct  900
atacccgatc aattaatcga gtcggagctg ttcggcgtag agcgcggagc ctttacaggt  960
gcgaccgcta cgcgagaggg gcgtttcgag gcggctcatc aaggcactct cttccttgac  1020
gaaattgcca ccctcagtat gaccgctcaa agtaaacttc tccgtgtatt gcagaatggc  1080
gaattggaac gtctcggtag caaccggaca atccacacca gtgtccgact gattgccgcc  1140
acgaacgctg atctgaaaaa agctgtccaa gatggtcact tccgagagga tctttactat  1200
cgactgaacg tctttcccat ccagattccc cctctgcgag aacgccgcga tgatatttca  1260
ctcattacca gcgtactcat cgctcgattt tctaaacgcc acggacgtaa gttaaaaggc  1320
atatcgtctg ccgccatgca ggtacttatc taccatgact ggccaggcaa tattcgagaa  1380
ttggagaacg tgattgagag agccataatc atggctcaag acgtcgattt tttggacacc  1440
caccatttaa cgacaattga aggcaccctc actacacaag acttcctgag tcttaaccag  1500
aaaggtgatt tgaccttgag cagcgagcta atacggaacg cggctgagaa cgccaaccct  1560
aaagttctct cattagatga gtttgccgag cagatggtgc atcaagggtc tattaacctg  1620
gaccaggttc aagacgccat cacccgagca gctgtcaaac atagcggtgg caatatttcc  1680
cgggcggcct cccttcttgg gataactcga gcccggcttg attaccgcgt caaaaagatc  1740
acatag                                                             1746

SEQ ID NO: 8           moltype = DNA  length = 9020
FEATURE                Location/Qualifiers
source                 1..9020
                       mol_type = other DNA
                       note = pBL_EB_02 hbpR
                       organism = synthetic construct
SEQUENCE: 8
gcggccgctg tggccgatct agggctgcaa cggggcatcg agggcagcaa ggcacgtcac  60
acgcgcattc aggcgttcta cgaggccctg gagcggccac cagtgggcca cgtcaccatc  120
agcccgcaag cggtcgagcc acgcgcctat gcaccgcagg gattggccga aaagctggga  180
atctcaaagc gcgttgagac gccggaagcc gtggccgacc ggctgacaaa agcggttcgg  240
caggggtatg agcctgccct acaggcgccc gcaggagcgc gtgagatgcg caagaaggcc  300
gatcaagccc aagagacggc ccgagacctt cgggagcgcc tgaagcccgt tctggacgcc  360
ctggggccgt tgaatcggga tatgcaggcc aaggccgccg cgatcatcaa ggccgtgggc  420
gaaaagctgc tgacggaaca gcgggaagtc cagcgccaga aacaggccca gcgccagcag  480
gaacgcgggc gcgcacattt ccccgaaaag tgccacctgg attttggtca tgagattatc  540
aaaaaggatc ttcacctaga tccttttaaa ttaaaaatga agttttaaat caatctaaag  600
tatatatgag taaacttggt ctgacagtta ccaatgctta atcagtgagg cacctatctc  660
agcgatctgt ctatttcgtt catccatagt tgcctgactc cccgtcgtgt agataactac  720
gatacgggag ggcttaccat ctggccccag tgctgcaatg ataccgcgag acccacgctc  780
accggctcca gatttatcag caataaacca gccagccgga agggccgagc gcagaagtgg  840
tcctgcaact ttatccgcct ccatccagtc tattaattgt tgccgggaag ctagagtaag  900
tagttcgcca gttaatagtt tgcgcaacgt tgttgccatt gctacaggca tcgtggtgtc  960
acgctcgtcg tttggtatgg cttcattcag ctccggttcc caacgatcaa ggcgagttac  1020
atgatccccc atgttgtgca aaaaagcggt tagctccttc ggtcctccga tcgttgtcag  1080
aagtaagttg gccgcagtgt tatcactcat ggttatggca gcactgcata attctcttac  1140
tgtcatgcca tccgtaagat gcttttctgt gactggtgag tactcaacca agtcattctg  1200
agaatagtgt atgcggcgac cgagttgctc ttgcccggcg tcaatacggg ataataccgc  1260
gccacatagc agaactttaa aagtgctcat cattggaaaa cgttcttcgg ggcgaaaact  1320
ctcaaggatc ttaccgctgt tgagatccag ttcgatgtaa cccactcgtg cacccaactg  1380
atcttcagca tcttttactt tcaccagcgt ttctgggtga gcaaaaacag gaaggcaaaa  1440
tgccgcaaaa aagggaataa gggcgacacg gaaatgttga atactcatac tcttcctttt  1500
```

```
tcaatattat tgaagcattt atcagggtta ttgtctcatg agcggataca tatttgaatg  1560
ggcaaatatt atacgcaagg cgacaaggtg ctgatgccgc tggcgattca ggttcatcat  1620
gccgtttgtg atggcttcca tgtcggcaga atgcttaatg aattacaaca gtttttatgc  1680
atgcgcccaa tacgcaaacc gcctctcccc gcgcgttggc cgattcatta atgcagctgg  1740
cacgacaggt ttcccgactg gaaagcgggc agtgagcgca acgcagcaag acgtagccca  1800
gcgcgtcggc cagcttgcaa ttcgcgctaa cttacattaa ttgcgttgcg ctcactgccc  1860
gctttccagt cgggaaacct gtcgtgccag ctgcattaat gaatcggcca acgcgcgggg  1920
agaggcggtt tgcgtattgg gcgccagggt ggtttttctt ttcaccagtg agacgggcaa  1980
cagctgattg cccttcaccg cctggccctg agagagttgc agcaagcggt ccacgctggt  2040
ttgccccagc aggcgaaaat cctgtttgat ggtggttaac ggcgggatat aacatgagct  2100
gtcttcggta tcgtcgtatc ccactaccga gatatccgca ccaacgcgca gcccggactc  2160
ggtaatggcg cgcattgcgc ccagcgccat ctgatcgttg gcaaccagca tcgcagtggg  2220
aacgatgccc tcattcagca tttgcatggt ttgttgaaaa ccggacatgg cactccagtc  2280
gccttcccgt tccgctatcg gctgaatttg attgcgagtg agatatttat gccagccagc  2340
cagacgcaga cgcgccgaga cagaacttaa tgggcccgct aacagcgcga tttgctggtg  2400
acccaatgcg accagatgct ccacgcccag tcgcgtaccg tcttcatggg agaaaataat  2460
actgttgatg ggtgtctggt cagagacatc aagaaataac gccggaacat tagtgcaggc  2520
agcttccaca gcaatggcat cctggtcatc cagcggatag ttaatgatca gcccactgac  2580
gcgttgcgcg agaagattgt gcaccgccgc tttacaggct tcgacgccgc ttcgttctac  2640
catcgacacc accacgctgg cacccagttg atcggcgcga gatttaatcg ccgcgacaat  2700
ttgcgacggc gcgtgcaggg ccagactgga ggtggcaacg ccaatcagca acgactgttt  2760
gcccgccagt tgttgtgcca cgcggttggg aatgtaattc agctccgcca tcgccgcttc  2820
cactttttcc cgcgttttcg cagaaacgtg gctggcctgg ttcaccacgc gggaaacggt  2880
ctgataagag acaccggcat actctgcgac atcgtataac gttactggtt tcacattcac  2940
caccctgaat tgactctctt ccgggcgcta tcatgccata ccgcgaaagg ttttgcacca  3000
ttcgatggtg tcaacgtaaa tgccgcttcg ccttcgcgcg cgaattgcaa gctgatccgg  3060
gcttatcgac tgcgtcaatt attacctcca cggggagagc ctgagcaaac tggcctcagg  3120
catttgagaa gcacacggtc acactgcttc cggtagtcaa taaaccggta aaccagcaat  3180
agacataagc ggctatttaa cgaccctgcc ctgaaccgac gaccgggtcg aatttgcttt  3240
cgaatttctg ccattcatcc gcttattatc acttattcag gcgtagcacc aggcgtttaa  3300
gggcaccaat aactgcctta aaaaaattac gccccgccct gccactcatc gcagtcggcc  3360
tattggttaa aaaatgagct gatttaacaa aaatttaacg cgaattttaa caaaatatta  3420
acgcttacaa tttccattcg ccattcttaa tggtgatgat gatggtggct gcctttatac  3480
agttcatcca taccgtgggt aatgcccgcg gcggtaacaa attccagcag caccatatga  3540
tcacgttttt cattcggatc tttgctcaga acgctctggg tgctcagata atgattatcc  3600
ggcagcagca ccgggccatc accaatcggg gtattctgct gataatgatc cgccagctgc  3660
acgctaccat cttccacgtt gtgacggatt ttaaagttcg ctttgatgcc atttttctgt  3720
ttatcggcgg taatatacac attatggctg ttgaaattat attccagttt atgacccaga  3780
atgttgccat cttctttaaa atcaatacct ttcagttcaa tgcggttcac cagggtatcg  3840
ccttcaaatt taacttccgc acgggtttta taggtgccat catctttgaa gctaatggta  3900
cgttcctgca catagccttc cggcatcgcg cttttaaaga aatcatggcg tttcatatga  3960
tccggatagc ggctaaagca ctgaacgcca taggtcaggg tggtcaccag ggtcggccac  4020
ggaaccggca gtttaccggt ggtgcaaata aatttcaggg tcagtttacc gttggtcgca  4080
tcaccttcgc cttcgccacg aacgctaaat ttatggccat tcacatcacc atccagttcc  4140
accagaatcg gcacaacgcc ggtaaacagt tcttcacctt tgctaaccat tgttatcacg  4200
tctccgcgtt catattgttt taataggcag cagtacagtc gaactcacgg ctgccttgcg  4260
ggactcgtag ccagtaccgt gccaggttga ctaagcagcc tcagacataa aagctaggat  4320
actgttttat aaggattttt attttaatga gcgccagaaa gcctagctcc agacggctgt  4380
aaaccccttc cgcggtcgcc aacagctgcc gaaatgcact tgccatggcg ggcaagcttc  4440
accatattat gaaaactcac aaccacgatt tcataaattt attaaatcta cgagaaccct  4500
atctactcct acctggcatg agctatcacc atgaaatcta acaaaaataa gaaccatgaa  4560
aaccgcacca tcgttgccga tctatcgcgc cctgaaatcc atgtttcggc gttcggtctg  4620
cattccctcc ccacaacgaa ggacgcatct ggctaggcga cagcccgatc catgcaccta  4680
cacacagtaa gactgaaggg aatatggatc cgtcggcaga tgccagaatg cgcctgctcg  4740
gacgagctgg tttcaccata ttctgaatcc caccaccaca atttaataaa attattaaac  4800
ccaacgagac cctcatctat tcctaccgga cctgaaccat cgccatggaa cagaagctta  4860
tatcggagga agatctcatg aaatcaaata aaaataatag cgacgatcgc agcattgtgg  4920
cggatctggc gctgccggaa gtgcatgcgc tggtgagtaa actgcatttt agcccgaatg  4980
aaggccgtat ttggctggat gaaagccgtt gcctgctgct gcaggtggaa accctgaaag  5040
atatttataa agaactgcag gcgtatagcg gcccagatta tacccgtgag tttctgaccc  5100
gtattggctt taccaccggc cagcgtgatg cggaaatgat tatcaaaaaa caaggcatta  5160
gcagcattaa ggaacagnnk tatgcaggtg gtgtgctgca tgccctgcag ggctttctga  5220
ccagcattca ggcgggcagc agcgcgctga atgcggtgga tatgaaaagc atggatnnkc  5280
atnnkgaggc atactggcag aatagcattg aagcggaaat tcatctggcg atgcatggcg  5340
tgagcagcca tgcggtgtgc tggtttagcg tggcgtatnn ktcagggtac nnkagcgcgt  5400
gcgcgggcaa accgattgtg gtggaagaaa ttgaatgcca ggcgatgggc catacccatt  5460
gccgtnnkca annkaaaccg gcggaaatgt gggcgctgag ccagagcgaa cagagccaga  5520
ttaccaccca tcctattccc gatgatgatc agggcggcga gctcgtcatt ggttcgtcgg  5580
cagtgttcaa ggtgctccgt cacaaaacag cctgtgtggc agagactgat gcgactgttc  5640
ttttacttgg agaaagtggg agcggcaaga gccttattgc acgcgagatc caccgtttga  5700
gcaaccgcgc cgaccaagct ttcgtcgaag tgaactgtgc cgctataccc gatcaattaa  5760
tcgagtcgga gctgttcggc gtagagcgcg gagcctttac aggtgcgacc gctacgcgag  5820
aggggcgttt cgaggcggct catcaaggca ctctcttcct tgacgaaatt gccaccctca  5880
gtatgaccgc tcaaagtaaa cttctccgtg tattgcagaa tggcgaattg gaacgtctcg  5940
gtagcaaccg gacaatccac accagtgtcc gactgattgc cgccacgaac gctgatctga  6000
aaaaagctgt ccaagatggt cacttccgag aggatcttta ctatcgactg aacgtctttc  6060
ccatccagat tccccctctg cgagaacgcc gcgatgatat ttcactcatt accagcgtac  6120
tcatcgctcg attttctaaa cgccacggac gtaagttaaa aggcatatcg tctgccgcca  6180
tgcaggtact tatctaccat gactggccag gcaatattcg agaattggag aacgtgattg  6240
```

```
agagagccat aatcatggct caagacgtcg attttttgga cacccaccat ttaacgacaa  6300
ttgaaggcac cctcactaca caagacttcc tgagtcttaa ccagaaaggt gatttgacct  6360
tgagcagcga gctaatacgg aacgcggctg agaacgccaa ccctaaagtt ctctcattag  6420
atgagtttgc cgagcagatg gtgcatcaag ggtctattaa cctggaccag gttcaagacg  6480
ccatcacccg agcagctgtc aaacatagcg gtggcaatat ttcccgggcg gcctcccttc  6540
ttgggataac tcgagcccgg cttgattacc gcgtcaaaaa gatcacatag gaggaagagc  6600
gagagtagct cttcaaataa aacgaaaggc tcagtcgaaa gactgggcct ttcgttttat  6660
ctgttgtttg tcggtgaacg ctctcatatg atcatttatt ctgcctccca gagcctgata  6720
aaaacggtga atccgttagc gaggtgccgc cggcttccat tcaggtcgag gtggcccggc  6780
tccatgcacc gcgacgcaac gcggggaggc agacaaggta tagggcggcg aggcggctac  6840
agccgatagt ctggaacagc gcacttacgg gttgctgcgc aacccaagtg ctaccggcgc  6900
ggcagcgtga cccgtgtcgg cggctccaac ggctcgccat cgtccagaaa acacggctca  6960
tcgggcatcg gcaggcgctg ctgcccgcgc cgttcccatt cctccgtttc ggtcaaggct  7020
ggcaggtctg gttccatgcc cggaatgccg ggctggctgg gcggctcctc gccggggccg  7080
gtcggtagtt gctgctcgcc cggatacagg gtcgggatgc ggcgcaggtc gccatgcccc  7140
aacagcgatt cgtcctggtc gtcgtgatca accaccacgg cggcactgaa caccgacagg  7200
cgcaactggt cgcggggctg gccccacgcc acgcggtcat tgaccacgta ggccgacacg  7260
gtgccggggc cgttgagctt cacgacggag atccagcgct cggccaccaa gtccttgact  7320
gcgtattgga ccgtccgcaa agaacgtccg atgagcttgg aaagtgtctt ctggctgacc  7380
accacggcgt tctggtggcc catctgcgcc acgaggtgat gcagcagcat tgccgccgtg  7440
ggtttcctcg caataagccc ggcccacgcc tcatgcgctt tgcgttccgt ttgcacccag  7500
tgaccgggct tgttcttggc ttgaatgccg atttctctgg actgcgtggc catgcttatc  7560
tccatgcggt agggtgccgc acggttgcgg caccatgcgc aatcagctgc aacttttcgg  7620
cagcgcgaca acaattatgc gttgcgtaaa agtggcagtc aattacagat ttctttaac  7680
ctacgcaatg agctattgcg gggggtgccg caatgagctg ttgcgtaccc cccttttta  7740
agttgttgat ttttaagtct ttcgcatttc gccctatatc tagttctttg gtgcccaaag  7800
aagggcaccc ctgcggggtt cccccacgcc ttcggcgcgg ctccccctcc ggcaaaaagt  7860
ggcccctccg gggcttgttg atcgactgcg cggccttcgg ccttgcccaa ggtggcgctg  7920
ccccttgga accccgcac tcgccgccgt gaggctcggg gggcaggcgg gcgggcttcg  7980
ccttcgactg cccccactcg cataggcttg ggtcgttcca ggcgcgtcaa ggccaagccg  8040
ctgcgcggtc gctgcgcgag ccttgacccg ccttccactt ggtgtccaac cggcaagcga  8100
agcgcgcagg ccgcaggccg gaggcttttc cccagagaaa attaaaaaaa ttgatggggc  8160
aaggccgcag gccgcgcagt tggagccggt gggtatgtgg tcgaaggctg ggtagccggt  8220
gggcaatccc tgtggtcaag ctcgtgggca ggcgcagcct gtccatcagc ttgtccagca  8280
gggttgtcca cgggccgagc gaagcgagcc agccggtggc cgctcgcggc catcgtccac  8340
atatccacgg gctggcaagg gagcgcagcg accgcgcagg gcgaagcccg gagagcaagc  8400
ccgtagggcg ccgcagccgc cgtaggcggt cacgactttg cgaagcaaag tctagtgagt  8460
atactcaagc attgagtggc ccgccggagg caccgccttg cgctgccccc gtcgagccgg  8520
ttggacacca aaagggaggg gcaggcatgg cggcatacgc gatcatgcga tgcaagaagc  8580
tggcgaaaat gggcaacgtg gcggccagtc tcaagcacgc ctaccgcgag cgcgagacgc  8640
ccaacgctga cgccagcagg acgccagaga acgagcactg ggcggccagc agcaccgatg  8700
aagcgatggg ccgactgcgc gagttgctgc cagagaagcg gcgcaaggac gctgtgttgg  8760
cggtcgagta cgtcatgacg gccagcccgg aatggtggaa gtcggccagc caagaacagc  8820
aggcggcgtt cttcgagaag gcgcacaagt ggctggcgga caagtacggg gcggatcgca  8880
tcgtgacggc cagcatccac cgtgacgaaa ccagcccgca catgaccgcg ttcgtggtgc  8940
cgctgacgca ggacggcagg ctgtcggcca aggagttcat cggcaacaaa gcgcagatga  9000
cccgcgacca gaccacgttt                                               9020

SEQ ID NO: 9            moltype = DNA  length = 8567
FEATURE                 Location/Qualifiers
source                  1..8567
                        mol_type = other DNA
                        note = pBL_IMP_11 (biphenyl)
                        organism = synthetic construct
SEQUENCE: 9
ctcgggccgt ctcttgggct tgatcggcct tcttgcgcat ctcacgcgct cctgcggcgg  60
cctgtagggc aggctcatac ccctgccgaa ccgcttttgt cagccggtcg gccacggctt  120
ccggcgtctc aacgcgcttt gagattccca gcttttcggc caatccctgc ggtgcatagg  180
cgcgtggctc gaccgcttgc gggctgatgg tgacgtggcc cactggtggc cgctccaggg  240
cctcgtagaa cgcctgaatg cgcgtgtgac gtgccttgct gccctcgatg ccccgttgca  300
gccctagatc ggccacagcg gccgcaaacg tggtctggtc gcgggtcatc tgcgctttgt  360
tgccgatgaa ctccttggcc gacagcctgc cgtcctgcgt cagcggcacc acgaacgcgg  420
tcatgtgcgg gctggtttcg tcacggtgga tgctggccgt cacgatgcga tccgccccgt  480
acttgtccgc cagccacttg tgcgccttct cgaagaacgc cgcctgctgt tcttggctgg  540
ccgacttcca ccattccggg ctggccgtca tgacgtactc gaccgccaac acagcgtcct  600
tgcgccgctt ctctggcagc aactcgcgca gtcggcccat cgcttcatcg gtgctgctgg  660
ccgcccagtg ctcgttctct ggcgtcctgc tggcgtcagc gttgggcgtc tcgcgctcgc  720
ggtaggcgtg cttgagactg gccgccacgt tgcccatttt cgccagcttc ttgcatcgca  780
tgatcgcgta tgccgccatg cctgcccctc ccttttggtg tccaaccggc tcgacggggg  840
cagcgcaagg cggtgcctcc ggcgggccac tcaatgcttg agtatactca ctagactttg  900
cttcgcaaag tcgtgaccgc ctacggcggc tgcggcgccc tacgggcttg ctctccgggc  960
ttcgccctgc gcggtcgctg cgctcccttg ccagcccgtg gatatgtgga cgatggccgc  1020
gagcggccac cggctggctc gcttcgctcg gcccgtggac aaccctgctg gacaagctga  1080
tggacaggct gcgcctgccc acgagcttga ccacagggat tgcccaccgg ctacccagcc  1140
ttcgaccaca tacccaccgg ctccaactgc gcggcctgcg gccttgcccc atcaattttt  1200
ttaattttct ctggggaaaa gcctccggcc tgcggcctgc gcgcttcgct tgccggttgg  1260
acaccaagtg gaaggcgggt caaggctcgc gcagcgaccg cgcagcggct tggccttgac  1320
gcgcctggaa cgacccaagc ctatgcgagt gggggcagtc gaaggcgaag cccgcccgcc  1380
tgcccccga gcctcacggc ggcgagtgcg ggggttccaa gggggcagcg ccaccttggg  1440
```

-continued

```
caaggccgaa ggccgcgcag tcgatcaaca agccccggag gggccacttt ttgccggagg  1500
gggagccgcg ccgaaggcgt gggggaaccc cgcaggggtg cccttctttg ggcaccaaag  1560
aactagatat agggcgaaat gcgaaagact taaaaatcaa caacttaaaa aagggggggta  1620
cgcaacagct cattgcggca ccccccgcaa tagctcattg cgtaggttaa agaaaatctg  1680
taattgactg ccacttttac gcaacgcata attgttgtcg cgctgccgaa aagttgcagc  1740
tgattgcgca tggtgccgca accgtgcggc accctaccgc atggagataa gcatggccac  1800
gcagtccaga gaaatcggca ttcaagccaa gaacaagccc ggtcactggg tgcaaacgga  1860
acgcaaagcg catgaggcgt gggccgggct tattgcgagg aaacccacgg cggcaatgct  1920
gctgcatcac ctcgtggcgc agatgggcca ccagaacgcc gtggtggtca gccagaagac  1980
actttccaag ctcatcggac gttctttgcg gacggtccaa tacgcagtca aggacttggt  2040
ggccgagcgc tggatctccg tcgtgaagct caacggcccc ggcaccgtgt cggcctacgt  2100
ggtcaatgac cgcgtggcgt ggggccagcc ccgcgaccag ttgcgcctgt cggtgttcag  2160
tgccgccgtg gtggttgatc acgacgacca ggacgaatcg ctgttggggc atggcgacct  2220
gcgccgcatc ccgaccctgt atccgggcga gcagcaacta ccgaccggcc ccggcgagga  2280
gccgcccagc cagcccggca ttccgggcat ggaaccagac ctgccagcct tgaccgaaac  2340
ggaggaatgg gaacggcgcg ggcagcagcg cctgccgatg cccgatgagc cgtgttttct  2400
ggacgatggc gagccgttgg agccgccgac acgggtcacg ctgccgcgcc ggtagcactt  2460
gggttgcgca gcaacccgta agtgcgctgt tccagactat cggctgtagc cgcctcgccg  2520
ccctatacct tgtctgcctc cccgcgttgc gtcgcggtgc atggagccgg gccacctcga  2580
cctgaatgga agccggcggc acctcgctaa cggattcacc gtttttatca ggctctggga  2640
ggcagaataa atgatcatat gagagcgttc accgacaaac aacagataaa acgaaaggcc  2700
cagtctttcg actgagcctt tcgttttatt tgaagagcta ctctcgctct tcctcctatg  2760
tgatcttttt gacgcggtaa tcaagccggg ctcgagttat cccaagaagg gaggccgccc  2820
gggaaatatt gccaccgcta tgtttgacag ctgctcgggt gatggcgtct tgaacctggt  2880
ccaggttaat agaccccttga tgcaccatct gctcggcaaa ctcatctaat gagagaactt  2940
tagggttggc gttctcagcc gcgttccgta ttagctcgct gctcaaggtc aaatcacctt  3000
tctggttaag actcaggaag tcttgtgtag tgagggtgcc ttcaattgtc gttaaatggt  3060
gggtgtccaa aaaatcgacg tcttgagcca tgattatggc tctctcaatc acgttctcca  3120
attctcgaat attgcctggc cagtcatggt agataagtac ctgcatggcg gcagacgata  3180
tgccttttaa cttacgtccg tggcgtttag aaaatcgagc gatgagtacg ctggtaatga  3240
gtgaaatatc atcgcggcgt tctcgcagag gggaatctg gatgggaaag acgttcagtc  3300
gatagtaaag atcctctcgg aagtgaccat cttggacagc ttttttcaga tcagcgttcg  3360
tggcggcaat cagtcggaca ctggtgtgga ttgtccggtt gctaccgaga cgttccaatt  3420
cgccattctg caatacacgg agaagtttac tttgagcggt catactgagg gtggcaattt  3480
cgtcaaggaa gagagtgcct tgatgagccg cctcgaaacg cccctctcgc gtagcggtcg  3540
cacctgtaaa ggctccgcgc tctacgccga acagctccga ctcgattaat tgatcgggta  3600
tagcggcaca gttcacttcg acgaaagctt ggtcggcgcg gttgctcaaa cggtggatct  3660
cgcgtgcaat aaggctcttg ccgctcccac tttctccaag taaaagaaca gtcgcatcag  3720
tctctgccac acaggctgtt ttgtgacgga gcaccttgaa cactgccgac gaaccaatga  3780
cgagctcgcc gccctgatca tcatcgggaa tagggtgcgt ggtgatctgg gattgctccg  3840
actgactgag cgcccacatt tcggcgggct tcgcttgaat acggcaatga gtgtgtccca  3900
tcgcttggca ttcgatctct tccacgacaa tgggttttcc agcgcatgcg ctcaggtacc  3960
ctgagcaata cgcaacggaa aaccaacata ccgcatgtga actgacacca tgcatcgcta  4020
agtgaatttc agcttcgatg ctgttctgcc agtatgcctc cgcatgataa tccatgctct  4080
tcatatcgac cgcatttagc gccgatgatc cagcttgtat agatgttaga aaccccttgca  4140
aggcgtgcaa gacaccacct gcataaatct gttctttgat agaggatata ccttgttttt  4200
ttataatcat ttctgcatcg cgttggccgg tggtgaagcc gatacgagtc aaaaactccc  4260
gcgtgtagtc tgggccagaa taggcctgca attccttgta tatatccttc agtgtctcca  4320
cttgtaggag caggcatcgg ctttcgtcca gccagatacg tccttcgttg ggagaaaagt  4380
gcagcttgga aactaaagca tggacttcgg ggagcgcaag gtcggcaacg atggagcgat  4440
cgtcgctatt atttttattt gatttcatgg cgatggttca ggtccggtag gaatagatga  4500
gggtctcgtt gggtttaata attttattaa attgtggtgg tgggattcag aatatggtga  4560
aaccagctcg tccgagcagg cgcattctgg catctgccga cggatccata ttcccttcag  4620
tcttactgtg tgtaggtgca tggatcgggc tgtcgcctag ccagatgcgt ccttcgttgt  4680
ggggagggaa tgcagaccga acgccgaaac atggatttca gggcgcgata gatcggcaac  4740
gatggtgcgg ttttcatggt tcttattttt gttagatttc atggtgatag ctcatgccag  4800
gtaggagtag atagggttct cgtagattta ataaatttat gaaatcgtgg ttgtgagttt  4860
tcataatatg gtgaagcttg cccgccatgg caagtgcatt tcggcagctg ttggcgaccg  4920
cggaaggggt ttacagccgt ctggagctag gctttctggc gctcattaaa ataaaaatcc  4980
ttataaaaca gtatcctagc ttttatgtct gaggctgctt agtcaacctg gcacggtact  5040
ggctacgagt cccgcaaggc agccgtgagt tcgactgtac tgctgcctat taaaacaata  5100
tgaacgcgga gacgtgataa caatgaccat gattacgcca agcttgcatg cctgcaggtc  5160
gactctagag gatccccggg taccgagctc gaattcactg gccgtcgttt tacaacgtcg  5220
tgactgggaa aaccctggcg ttacccaact taatcgcctt gcagcacatc cccctttcgc  5280
cagctggcgt aatagcgaag aggcccgcac cgatcgccct tcccaacagt tgcgcagcct  5340
gaatggcgaa tggcgcctga tgcggtattt tctccttacg catctgtgcg gtatttcaca  5400
ccgcatatgg tgcactctca gtacaatctg ctctgatgcc gcataagaat ggcgaatgga  5460
aattgtaagc gttaatattt tgttaaaatt cgcgttaaat ttttgttaaa tcagctcatt  5520
ttttaaccaa taggccgact gcgatgagtg gcagggcggg gcgtaatttt tttaaggcag  5580
ttattggtgc ccttaaacgc ctggtgctac gcctgaataa gtgataataa gcggatgaat  5640
ggcagaaatt cgaaagcaaa ttcgacccgg tcgtcggttc agggcagggt cgttaaatag  5700
ccgcttatgt ctattgctgg tttaccggtt tattgactac cggaagcagt gtgaccgtgt  5760
gcttctcaaa tgcctgaggc cagtttgctc aggctctccc cgtggaggta ataattgacg  5820
cagtcgataa gcccggatca gcttgcaatt cgcgcgcgaa ggcgaagcgg catttacgtt  5880
gacaccatcg aatggtgcaa aacctttcgc ggtatggcat gatagcgccc ggaagagagt  5940
caattcaggg tggtgaatgt gaaaccagta acgttatacg atgtcgcaga gtatgccggt  6000
gtctcttatc agaccgtttc ccgcgtggtg aaccaggcca gccacgtttc tgcgaaaacg  6060
cgggaaaaag tggaagcggc gatggcggag ctgaattaca ttcccaaccg cgtggcacaa  6120
caactggcgg gcaaacagtc gttgctgatt ggcgttgcca cctccagtct ggccctgcac  6180
```

```
gcgccgtcgc aaattgtcgc ggcgattaaa tctcgcgccg atcaactggg tgccagcgtg  6240
gtggtgtcga tggtagaacg aagcggcgtc gaagcctgta aagcggcggt gcacaatctt  6300
ctcgcgcaac gcgtcagtgg gctgatcatt aactatccgc tggatgacca ggatgccatt  6360
gctgtggaag ctgcctgcac taatgttccg gcgttatttc ttgatgtctc tgaccagaca  6420
cccatcaaca gtattatttt ctcccatgaa gacggtacgc gactgggcgt ggagcatctg  6480
gtcgcattgg gtcaccagca aatcgcgctg ttagcgggcc cattaagttc tgtctcggcg  6540
cgtctgcgtc tggctggctg gcataaatat ctcactcgca atcaaattca gccgatagcg  6600
gaacgggaag gcgactggag tgccatgtcc ggttttcaac aaaccatgca aatgctgaat  6660
gagggcatcg ttcccactgc gatgctggtt gccaacgatc agatggcgct gggcgcaatg  6720
cgcgccatta ccgagtccgg gctgcgcgtt ggtgcggata tctcggtagt gggatacgac  6780
gataccgaag acagctcatg ttatatcccg ccgttaacca ccatcaaaca ggattttcgc  6840
ctgctggggc aaaccagcgt ggaccgcttg ctgcaactct ctcagggcca ggcggtgaag  6900
ggcaatcagc tgttgcccgt ctcactggtg aaaagaaaaa ccaccctggc gcccaatacg  6960
caaaccgcct ctccccgcgc gttggccgat tcattaatgc agctggcacg acaggtttcc  7020
cgactggaaa gcgggcagtg agcgcaacgc aattaatgta agttagcgcg aattgcaagc  7080
tggccgacgc gctgggctac gtcttgctgc gttgcgctca ctgcccgctt tccagtcggg  7140
aaacctgtcg tgccagctgc attaatgaat cggccaacgc gcggggagag gcggtttgcg  7200
tattgggcgc atgcataaaa actgttgtaa ttcattaagc attctgccga catggaagcc  7260
atcacaaacg gcatgatgaa cctgaatcgc cagcggcatc agcaccttgt cgccttgcgt  7320
ataatatttg cccattcaaa tatgtatccg ctcatgagac aataaccctg ataaatgctt  7380
caataatatt gaaaaaggaa gagtatgagt attcaacatt tccgtgtcgc ccttattccc  7440
ttttttgcgg cattttgcct tcctgttttt gctcacccag aaacgctggt gaaagtaaaa  7500
gatgctgaag atcagttggg tgcacgagtg ggttacatcg aactggatct caacagcggt  7560
aagatccttg agagttttcg ccccgaagaa cgttttccaa tgatgagcac ttttaaagtt  7620
ctgctatgtg gcgcggtatt atcccgtatt gacgccgggc aagagcaact cggtcgccgc  7680
atacactatt ctcagaatga cttggttgag tactcaccag tcacagaaaa gcatcttacg  7740
gatggcatga cagtaagaga attatgcagt gctgccataa ccatgagtga taacactgcg  7800
gccaacttac ttctgacaac gatcggagga ccgaaggagc taaccgcttt tttgcacaac  7860
atgggggatc atgtaactcg ccttgatcgt tgggaaccgg agctgaatga agccatacca  7920
aacgacgagc gtgacaccac gatgcctgta gcaatggcaa caacgttgcg caaactatta  7980
actggcgaac tacttactct agcttcccgg caacaattaa tagactggat ggaggcggat  8040
aaagttgcag gaccacttct gcgctcggcc cttccggctg gctggtttat tgctgataaa  8100
tctggagccg gtgagcgtgg gtctcgcggt atcattgcag cactggggcc agatggtaag  8160
ccctcccgta tcgtagttat ctacacgacg gggagtcagg caactatgga tgaacgaaat  8220
agacagatcg ctgagatagg tgcctcactg attaagcatt ggtaactgtc agaccaagtt  8280
tactcatata tactttagat tgatttaaaa cttcattttt aatttaaaag gatctaggtg  8340
aagatccttt ttgataatct catgaccaaa atccaggtgg cacttttcgg ggaaatgtgc  8400
gcgcccgcgt tcctgctggc gctgggcctg tttctggcgc tggacttccc gctgttccgt  8460
cagcagcttt tcgcccacgg ccttgatgat cgcggcggcc ttggcctgca tatcccgatt  8520
caacggcccc agggcgtcca gaacgggctt caggcgctcc cgaaggt                8567
```

```
SEQ ID NO: 10           moltype = DNA  length = 10837
FEATURE                 Location/Qualifiers
source                  1..10837
                        mol_type = other DNA
                        note = pBL_IMP_25 (ampl end amilCP)
                        organism = synthetic construct
SEQUENCE: 10
caaaagcaac agcgaggcag catggcgatt tatcacctta cggcgaaaac cggcagcagg  60
tcgggcggcc aatcggccag ggccaaggcc gactacatcc agcgcgaagg caagtatgcc  120
cgcgacatgg atgaagtctt gcacgccgaa tccgggcaca tgccggagtt cgtcgagcgg  180
cccgccgact actgggatgc tgccgacctg tatgaacgcg ccaatgggcg gctgttcaag  240
gaggtcgaat ttgccctgcc ggtcgagctg accctcgacc agcagaaggc gctggcgtcc  300
gagttcgccc agcacctgac cggtgccgag cgcctgccgt atacgctggc catccatgcc  360
ggtggcggcg agaacccgca ctgccacctg atgatctccg agcggatcaa tgacggcatc  420
gagcggcccg ccgctcagtg gttcaagcgg tacaacggca agaccccgga gaagggcggg  480
gcacagaaga ccgaagcgct caagcccaag gcatggcttg agcagacccg cgaggcatgg  540
gccgaccatg ccaaccgggc attagagcgg gctggccacg acgcccgcat tgaccacaga  600
acacttgagg cgcagggcat cgagcgcctg cccggtgttc acctggggcc gaacgtggtg  660
gagatggaag gccggggcat ccgcaccgac cgggcagacg tggccctgaa catcgacacc  720
gccaacgccc agatcatcga cttacaggaa taccgggagg caatagacca tgaacgcaat  780
cgacagagtg aagaaatcca gaggcatcaa cgagttagcg gagcagatcg aaccgctggc  840
ccagagcatg gcgacactgg ccgacgaagc ccggcaggtc atgagccaga ccaagcaggc  900
cagcgaggcg caggcggcgg agtggctgaa agcccagcgc cagacagggg cggcatgggt  960
ggagctggcc aaagagttgc gggaggtagc cgccgaggtg agcagcgccg cgcagagcgc  1020
ccggagcgcg tcgcgggggt ggcactggaa gctatggcta accgtgatgc tggcttccat  1080
gatgcctacg gtggtgctgc tgatcgcatc gttgctcttg ctcgacctga cgccactgac  1140
aaccgaggac ggctcgatct ggctgcgctt ggtggcccga tgaagaacga caggactttg  1200
caggccatag gccgacagct caaggccatg ggctgtgagc gcttcgatat cggcgtcagg  1260
gacgcaccca ccggccagat gatgaaccgg gaatggtcag ccgccgaagt gctccagaac  1320
acgccatggc tcaagcggat gaatgcccag ggcaatgacg tgtatatcag gcccgccgag  1380
caggagcggc atggtctggt gctggtggac gacctcagcg agtttgacct ggatgacatg  1440
aaagccgagg gccgggagcc tgccctggta gtggaaacca gcccgaagaa ctatcaggca  1500
tgggtcaagg tggccgacgc cgcaggcggt gaacttcggg ggcagattgc ccggacgctg  1560
gccagcgagt acgacgccga cccggccagc gccgacagcc gccactatgg ccgcttggcg  1620
ggcttcacca accgcaagga caagcacacc acccgcgccg gttatcagcc gtgggtgctg  1680
ctgcgtgaat ccaagggcaa gaccgccacc gctggcccgg cgctggtgca gcaggctggc  1740
cagcagatcg agcaggccca gcggcagcag gagaaggccc gcaggctggc cagcctcgaa  1800
ctgcccgagc ggcagcttag ccgccaccgg cgcacggcgc tggacgagta ccgcagcgag  1860
```

```
atggccgggc tggtcaagcg cttcggtcat gacctcagca agtgcgactt tatcgccgcg  1920
cagaagctgg ccagccgggg ccgcagtgcc gaggaaatcg gcaaggccat ggccgaggcc  1980
agcccagcgc tggcagagcg caagcccggc cacgaagcgg attacatcga gcgcaccgtc  2040
agcaaggtca tgggtctgcc cagcgtccag cttgcgcggg ccgagctggc acgggcaccg  2100
gcaccccgcc agcgaggcat ggacaggggc gggccagatt tcagcatgta gtgcttgcgt  2160
tggtactcac gcctgttata ctatgagtac tcacgcacag aagggggttt tatggaatac  2220
gaaaaaagcg cttcagggtc ggtctacctg atcaaaagtg acaagggcta ttggttgccc  2280
ggtggctttg gttatacgtc aaacaaggcc gaggctggcc gcttttcagt cgctgatatg  2340
gccagcctta accttgacgg ctgcaccttg tccttgttcc gcgaagacaa gcctttcggc  2400
cccggcaagt ttctcggtga ctgatatgaa agaccaaaag gacaagcaga ccggcgacct  2460
gctggccagc cctgacgctg tacgccaagc gcgatatgcc gagcgcatga aggccaaagg  2520
gatgcgtcag cgcaagttct ggctgaccga cgacgaatac gaggcgctgc gcgagtgcct  2580
ggaagaactc agagcggcgc agggcggggg tagtgacccc gccagcgcct aaccaccaac  2640
tgcctgcaaa ggaggcaatc aatggctacc cataagccta tcaatattct ggaggcgttc  2700
gcagcagcgc cgccaccgct ggactacgtt ttgcccaaca tggtggccgg tacggtcggg  2760
gcgctggtgt cgcccggtgg tgccggtaaa tccatgctgg ccctgcaact ggccgcacag  2820
attgcaggcg ggccggatct gctggaggtg ggcgaactgc ccaccggccc ggtgatctac  2880
ctgcccgccg aagacccgcc caccgccatt catcaccgcc tgcacgccct tggggcgcac  2940
ctcagcgccg aggaacggca agccgtggct gacggcctgc tgatccagcc gctgatcggc  3000
agcctgccca acatcatggc cccggagtgg ttcgacggcc tcaagcgcgc cgccgagggc  3060
cgccgcctga tggtgctgga cacgctgcgc cggttccaca tcgaggaaga aaacgccagc  3120
ggccccatgg cccaggtcat cggtcgcatg gaggccatcg ccgccgatac cgggtgctct  3180
atcgtgttcc tgcaccatgc cagcaagggc gcggccatga tgggcgcagg cgaccagcag  3240
caggccagcc ggggcagctc ggtactggtc gataacatcc gctggcagtc ctacctgtcg  3300
agcatgacca gcgccgaggc cgaggaatgg ggtgtggacg acgaccagcg ccggttcttc  3360
gtccgcttcg gtgtgagcaa ggccaactat ggcgcaccgt tcgctgatcg gtggttcagg  3420
cggcatgacg gcggggtgct caagcccgcc gtgctggaga ggcagcgcaa gagcaagggg  3480
gtgccccgtg gtgaagccta agaacaagca cagcctcagc cacgtccggc acgacccggc  3540
gcactgtctg gcccccggcc tgttccgtgc cctcaagcgg ggcgagcgca agcgcagcaa  3600
gctggacgtg acgtatgact acggcgacgg caagcggatc gagttcagcg gcccggagcc  3660
gctgggcgct gatgatctgc gcatcctgca agggctggtg gccatggctg ggcctaatgg  3720
cctagtgctt ggcccggaac ccaagaccga aggcggacgg cagctccggc tgttcctgga  3780
acccaagtgg gaggccgtca ccgctgaatg ccatgtggtc aaaggtagct atcgggcgct  3840
ggcaaaggaa atcggggcag aggtcgatag tggtggggcg ctcaagcaca tacaggactg  3900
catcgagcgc ctttggaagg tatccatcat cgcccagaat ggccgcaagc ggcaggggtt  3960
tcggctgctg tcggagtacg ccagcgacga ggcggacggg cgcctgtacg tggccctgaa  4020
ccccttgatc gcgcaggccg tcatgggtgg cggccagcat gtgcgcatca gcatggacga  4080
ggtgcgggcg ctggacagcg aaaccgcccg cctgctgcac cagcggctgt gtggctggat  4140
cgaccccggc aaaaccggca aggcttccat agataccttg tgcggctatg tctggccgtc  4200
agaggccagt ggttcgacca tgcgcaagcg ccgcaagcgg gtgcgcgagg cgttgccgga  4260
gctggtcgcg ctgggctgga cggtaaccga gttcgcggcg ggcaagtacg acatcacccg  4320
gcccaaggcg gcaggctgac cccccccact ctattgtaaa caagacattt ttatctttta  4380
tattcaatgg cttattttcc tgctaattgg taataccatg aaaaatacca tgctcagaaa  4440
aggcttaaca atattttgaa aaattgccta ctgagcgctg ccgcacagct ccataggccg  4500
ctttcctggc tttgcttcca gatgtatgct cttctgctcc cgaacgccag caagacgtag  4560
cccagcgcgt cggccagctt gcaattcgcg ctaacttaca ttaattgcgt tgcgcgccgg  4620
attatgtccg ctgagtgggt cacggtcccg gatcagttcc cttgcgaagc tgaccgatgt  4680
ttttgtgcca aaagctgttg tggcaaaaaa cggtttgcgc aaagttttgt attacaaaga  4740
atttcacatt ttaaaatatc tttataaatc aatcagttat ttctattttt aagctggcat  4800
ggttatcgct atagggcttg tactactaga gattaaagag gagaaatact agatgagtac  4860
aggcatcgat aaggacgtcc gagagtgttg gggcgtaact gcattatcag cgggtcatca  4920
aattgcaatg aatagcgcgt ttctggatat ggacttgctg ttgtgcgggg aaaccggcac  4980
cggcaaggac acactggcca accgcattca cgagttgtcc agcaggtcgg gaccctttgt  5040
gggcatgaac tgcgccgcca ttcccgagtc gctggcagag agccagttat tcggtgtggt  5100
caacggtgca ttcaccggcg tatgccgggc tcgcgagggc tacatagagg cctccagtgg  5160
tggcaccttg tacctggatg aaatcgacag catgccgttg agcctgcaag ccaaactgct  5220
gcgtgtgttg gagagtcgag gtatcgagcg tctgggctcg accgaattta tcccggtgga  5280
tctgcggatc attgcctcgg cccagcggcc actggatgaa ctggtggaac aaggactttt  5340
ccgtcgcgac ctgttttttc ggctcaacgt gctgacgctt cacttgccag ccttgcgcaa  5400
acgtcgtgaa cagatcctgc cattgttcga ccagttcacc cagggtatcg ctgccgagtt  5460
cggacgtccc gctcctgcgc tggacagcgg gcgtgtgcag ctgctgctca gccacgactg  5520
gccgggcaac atccgcgaat tgaagtctgc ggccaagcgc ttcgtactcg gcttcccctt  5580
gctgggcgcc gaccctgtgg aagcgcttga ccctgccacg gggctgcgca cgcaaatgcg  5640
catcatcgag aaaatgctca tccaggatgc cttgaagcgg cacaggcaca atttcgacgc  5700
ggtgcttcag gagttggagt tgccaagacg caccctgtat caccgcatga aggaactggg  5760
agttgcagcg ccgatcgctg cgacggccgg ggtctaataa ccaggcatca aagaggagaa  5820
aatgagtctt gatgaaaggt ttgaggatga tctggacgag gagcgggttc cgaatctggg  5880
gatagttgcc gaaagtattt cgcaactggg tatcgacgtg ctgctatcgg gtgagaccgg  5940
cacgggcaaa gacacgattg cccgacggat tcatgagatg tcaggccgca aagggcgcct  6000
ggtggcgatg aattgcgcgg ccattccgga gtccctcgcc gagagcgagt tattcggcgt  6060
ggtcagcggt gcctacaccg gcgctgatcg ctccagagtc ggttatgtcg aagcggcgca  6120
gggcggcacg ctgtacctgg atgagatcga tagcatgccg ctgagcctgc aagccaaatt  6180
gctgagggtg ctggaaaccc gagcgcttga acggctgggt tcgacgtcga cgatcaagct  6240
ggatatctgc gtgatcgcct ccgcccaatg ctcgctggac gacgccgtcg agcgggggca  6300
gtttcgtcgc gatctgtatt ttcgcctgaa cgtcctgaca ctcaagcttc ctccgctacg  6360
taaccagtct gatcgcatag ttccccctgtt cacacgtttt acggccgccg ccgcgaggga  6420
gctcggtgtt cccgttcccg atgtttgccc actgctgcac aaagtgctgc tgggccacga  6480
ctggcccggc aatatccgtg agctcaaggc ggcagccaaa cgccatgtgc tgggtttccc  6540
cttgctgggc gccgagccgc agggcgaaga gcacttggcc tgtgggctca aatcgcaatt  6600
```

```
gcgagtgatc gaaaaagccc tgattcagga gtcgctcaag cgccacgaca attgtgtgga  6660
ttcggtaagc ctggaactgg acgtgccacg ccgtacgctc tatcgacgca tcaaagaatt  6720
gcagatctaa tgctgccacc gcaaagagga gaaatactag atgagtgtga tcgctaaaca  6780
aatgacctac aaggtttata tgtcaggcac ggtcaatgga cactactttg aggtcgaagg  6840
cgatggaaaa ggtaagccct acgaggggga gcagacggta aagctcactg tcaccaaggg  6900
cggacctctg ccatttgctt gggatatttt atcaccacag tgtcagtacg gaagcatacc  6960
attcaccaag taccctgaag acatccctga ctatgtaaag cagtcattcc cggagggcta  7020
tacatgggag aggatcatga actttgaaga tggtgcagtg tgtactgtca gcaatgattc  7080
cagcatccaa ggcaactgtt tcatctacca tgtcaagttc tctggtttga actttcctcc  7140
caatggacct gtcatgcaga agaagacaca gggctgggaa cccaacactg agcgtctctt  7200
tgcacgagat ggaatgctgc taggaaacaa ctttatggct ctgaagttag aaggaggcgg  7260
tcactatttg tgtgaattta aaactactta caaggcaaag aagcctgtga agatgccagg  7320
gtatcactat gttgaccgca aactggatgt aaccaatcac aacaaggatt acacttcggt  7380
tgagcagtgt gaaatttcca ttgcacgcaa acctgtggtc gcctaataat actagagcca  7440
ggcatcaaat aaaacgaaag gctcagtcga aagactgggc ctttcgtttt atctgttgtt  7500
tgtcggtgaa cgctctctac tagagtcaca ctggctcacc ttcgggtggg cctttctgcg  7560
tttatatact agtagcggcc gctgcagtcc ggcaaaaaag ggcaaggtgt caccaccctg  7620
cccttttct ttaaaaccga aaagaatgtg gacaaattct tccaactgat ccgcgagctt  7680
cacgctgccg caagcactca gggcgcaagg gctgctaaag gaagcggaac acgtagaaag  7740
ccagtccgca gaaacggtgc tgaccccgga tgaatgtcag ctactgggct atctggacaa  7800
gggaaaacgc aagcgcaaag agaaagcagg tagcttgcag tgggcttaca tggcgatagc  7860
tagactgggc ggttttatgg acagcaagcg aaccggaatt gccagctggg gcgccctctg  7920
gtaaggttgg gaagccctgc aaagtaaact ggatggcttt cttgccgcca aggatctgat  7980
ggcgcagggg atcaagatct gatcaagaga caggatgagg atcgtttcgc atgattgaac  8040
aagatggatt gcacgcaggt tctccggccg cttgggtgga gaggctattc ggctatgact  8100
gggcacaaca gacaatcggc tgctctgatg ccgccgtgtt ccggctgtca gcgcaggggc  8160
gcccggttct ttttgtcaag accgacctgt ccggtgccct gaatgaactg caggacgagg  8220
cagcgcggct atcgtggctg gccacgacgg gcgttccttg cgcagctgtg ctcgacgttg  8280
tcactgaagc gggaagggac tggctgctat tgggcgaagt gccggggcag gatctcctgt  8340
catctcacct tgctcctgcc gagaaagtat ccatcatggc tgatgcaatg cggcggctgc  8400
atacgcttga tccggctacc tgcccattcg accaccaagc gaaacatcgc atcgagcgag  8460
cacgtactcg gatggaagcc ggtcttgtcg atcaggatga tctggacgaa gagcatcagg  8520
ggctcgcgcc agccgaactg ttcgccaggc tcaaggcgcg catgcccgac ggcgaggatc  8580
tcgtcgtgac ccatggcgat gcctgcttgc cgaatatcat ggtggaaaat ggccgctttt  8640
ctggattcat cgactgtggc cggctgggtg tggcggaccg ctatcaggac atagcgttgg  8700
ctacccgtga tattgctgaa gagcttggcg gcgaatgggc tgaccgcttc ctcgtgcttt  8760
acggtatcgc cgctcccgat tcgcagcgca tcgccttcta tcgccttctt gacgagttct  8820
tctgagcggg actctggggt tcgaaatgac cgaccaagcg acgcccaacc tgccatcacg  8880
agatttcgat tccaccgccg ccttctatga aaggttgggc ttcggaatcg ttttccggga  8940
cgccggctgg atgatcctcc agcgcgggga tctcatgctg gagttcttcg cccaccccgg  9000
gctcgatccc ctcgcgagtt ggttcagctg ctgcctgagg ctggacgacc tcgcggagtt  9060
ctaccggcag tgcaaatccg tcggcatcca ggaaaccagc agcggctatc cgcgcatcca  9120
tgccccgaa ctgcaggagt ggggaggcac gatggccgct ttggtcgacg gatcagtgag  9180
ggtttgcaac tgcgggtcaa ggatctggat ttcgatcacg gcacgatcat cgtgcgggag  9240
ggcaagggct ccaaggatcg ggccttgatg ttacccgaga gcttggcacc cagcctgcgc  9300
gagcagggga attgatccgg tggatgacct tttgaatgac ctttaataga ttatattact  9360
aattaattgg ggaccctaga ggtccccttt tttattttaa aaatttttc acaaaacggt  9420
ttacaagcat aaagctaaac gtggccaata tggacaactt cttcgccccc gttttcacca  9480
tgggcaaata ttatacgcaa ggcgacaagg tgctgatgcc gctggcgatt caggttcatc  9540
atgccgtttg tgatggcttc catgtcggca gaatgcttaa tgaattacaa cagtactgcg  9600
atgagtggca gggcggggcg taattttttt aaggcagtta ttgtcttcaa attcccgttg  9660
cacatagccc ggcaattcct ttccctgctc tgccataagc gcagcgaatg ccgggtaata  9720
ctcgtcaacg atctgataga gaagggtttg ctcgggtcgg tggctctggt aacgaccagt  9780
atcccgatcc cggctggccg tcctggccgc cacatgaggc atgttccgcg tccttgcaat  9840
actgtgttta catacagtct atcgcttagc ggaaagttct tttaccctca gccgaaatgc  9900
ctgccgttgc tagacattgc cagccagtgc ccgtcactcc cgtactaact gtcacgaacc  9960
cctgcaataa ctgtcacgcc cccctgcaat aactgtcacg aacccctgca ataactgtca  10020
cgcccccaaa cctgcaaacc cagcaggggc gggggctggc ggggtgttgg aaaaatccat  10080
ccatgattat ctaagaataa tccactaggc gcggttatca gcgcccttgt ggggcgctgc  10140
tgcccttgcc caatatgccc ggccagaggc cggatagctg gtctattcgc tgcgctaggc  10200
tacacaccgc cccaccgctg cgcggcaggg ggaaaggcgg gcaaagcccg ctaaacccca  10260
caccaaaccc cgcagaaata cgctggagcg cttttagccg ctttagcggc ctttccccct  10320
acccgaaggg tgggggcgcg tgtgcagccc cgcagggcct gtctcggtcg atcattcagc  10380
ccggctcatc cttctggcgt ggcggcagac cgaacaaggc gcggtcgtgg tcgcgttcaa  10440
ggtacgcatc cattgccgcc atgagccgat cctccggcca ctcgctgctg ttcaccttgg  10500
ccaaaatcat ggcccccacc agcaccttgc gccttgtttc gttcttgcgc tcttgctgct  10560
gttcccttgc ccgctcccgc tgaatttcgg cattgattcg cgctcgttgt tcttcgagct  10620
tggccagccg atccgccgcc ttgttgctcc ccttaaccat cttgacaccc cattgttaat  10680
gtgctgtctc gtaggctatc atggaggcac agcggcggca atcccgaccc tactttgtag  10740
gggagggcgc acttaccggt ttctcttcga gaaactggcc taacggccac ccttcgggcg  10800
gtgcgctctc cgagggccat tgcatggagc cgaaaag                          10837
```

```
SEQ ID NO: 11          moltype = DNA  length = 8537
FEATURE                Location/Qualifiers
source                 1..8537
                       mol_type = other DNA
                       note = pBL_IMP_26 (tac ampl amilCP)
                       organism = synthetic construct
SEQUENCE: 11
```

-continued

```
cagttacttc gagcgtaatg tctcaaatgg cgtagaacgg caatgactgt ttgacgacag 60
gtttcccgac tggaaagcgg gcagtgagcg caacgcaatt cagcaagacg tagcccagcg 120
cgtcggccag cttgcaattc gcgctaactt acattaattg cgttgcgctc actgcccgct 180
ttccagtcgg gaaacctgtc gtgccagctg cattaatgaa tcggccaacg cgcgggggaga 240
ggcggtttgc gtattgggcg ccagggtggt ttttcttttc accagtgaga cgggcaacag 300
ctgattgccc ttcaccgcct ggccctgaga gagttgcagc aagcggtcca cgctggtttg 360
ccccagcagg cgaaaatcct gtttgatggt ggttaacggc gggatataac atgagctgtc 420
ttcggtatcg tcgtatccca ctaccgagat atccgcacca acgcgcagcc cggactcggt 480
aatggcgcgc attgcgccca gcgccatctg atcgttggca accagcatcg cagtgggaac 540
gatgccctca ttcagcattt gcatggtttg ttgaaaaccg gacatggcac tccagtcgcc 600
ttcccgttcc gctatcggct gaatttgatt gcgagtgaga tatttatgcc agccagccag 660
acgcagacgc gccgagacag aacttaatgg gcccgctaac agcgcgattt gctggtgacc 720
caatgcgacc agatgctcca cgcccagtcg cgtaccgtct tcatgggaga aaataatact 780
gttgatgggt gtctggtcag agacatcaag aaataacgcc ggaacattag tgcaggcagc 840
ttccacagca atggcatcct ggtcatccag cggatagtta atgatcagcc cactgacgcg 900
ttgcgcgaga agattgtgca ccgccgcttt acaggcttcg acgccgcttc gttctaccat 960
cgacaccacc acgctggcac ccagttgatc ggcgcgagat ttaatcgccg cgacaatttg 1020
cgacggcgcg tgcagggcca gactggaggt ggcaacgcca atcagcaacg actgtttgcc 1080
cgccagttgt tgtgccacgc ggttgggaat gtaattcagc tccgccatcg ccgcttccac 1140
tttttcccgc gttttcgcag aaacgtggct ggcctggttc accacgcggg aaacggtctg 1200
ataagagaca ccggcatact ctgcgacatc gtataacgtt actggtttca cattcaccac 1260
cctgaattga ctctcttccg ggcgctatca tgccataccg cgaaaggttt tgcaccattc 1320
gatggtgtca acgtaaatgc cgcttcgcct tcgcccgggg atctcgagga aagcgggcag 1380
tgagcgcaac gcaattaatg taagttagct cactcattag gcaccccagg ctttacactt 1440
tatgcttccg gctcgtatgt tgtgtggaat tgtgagcgga taacaatttc acacaggtct 1500
agaaggagat ataccatgag tacaggcatc gataaggacg tccgagagtg ttggggcgta 1560
actgcattat cagcgggtca tcaaattgca atgaatagcg cgtttctgga tatggacttg 1620
ctgttgtgcg gggaaaccgg caccggcaag gacacactgg ccaaccgcat tcacgagttg 1680
tccagcaggt cgggaccctt tgtgggcatg aactgcgccg ccattcccga gtcgctggca 1740
gagagccagt tattcggtgt ggtcaacggt gcattcaccg gcgtatgccg ggctcgcgag 1800
ggctacatag aggcctccag tggtggcacc ttgtacctgg atgaaatcga cagcatgccg 1860
ttgagcctgc aagccaaact gctgcgtgtg ttggagagtc gaggtatcga gcgtctgggc 1920
tcgaccgaat ttatcccggt ggatctgcgg atcattgcct cggcccagcg gccactggat 1980
gaactggtgg aacaaggact tttccgtcgc gacctgtttt ttcggctcaa cgtgctgacg 2040
cttcacttgc cagccttgcg caaacgtcgt gaacagatcc tgccattgtt cgaccagttc 2100
acccagggta tcgctgccga gttcggacgt cccgctcctg cgctggacag cgggcgtgtg 2160
cagctgctgc tcagccacga ctggccgggc aacatccgcg aattgaagtc tgcggccaag 2220
cgcttcgtac tcggcttccc cttgctgggc gccgaccctg tggaagcgct tgaccctgcc 2280
acggggctgc gcacgcaaat gcgcatcatc gagaaaatgc tcatccagga tgccttgaag 2340
cggcacaggc acaatttcga cgcggtgctt caggagttgg agttgccaag acgcaccctg 2400
tatcaccgca tgaaggaact gggagttgca gcgccgatcg ctgcgacggc cggggtctaa 2460
taaccaggca tcaaagagga gaaaatgagt cttgatgaaa ggtttgagga tgatctggac 2520
gaggagcggg ttccgaatct ggggatagtt gccgaaagta tttcgcaact gggtatcgac 2580
gtgctgctat cgggtgagac cggcacgggc aaagacacga ttgcccgacg gattcatgag 2640
atgtcaggcc gcaaagggcg cctggtggcg atgaattgcg cggccattcc ggagtccctc 2700
gccgagagcg agttattcgg cgtggtcagc ggtgcctaca ccggcgctga tcgctccaga 2760
gtcggttatg tcgaagcggc gcagggcggc acgctgtacc tggatgagat cgatagcatg 2820
ccgctgagcc tgcaagccaa attgctgagg gtgctggaaa cccgagcgct tgaacggctg 2880
ggttcgacgt cgacgatcaa gctggatatc tgcgtgatcg cctccgccca atgctcgctg 2940
gacgacgccg tcgagcgggg gcagtttcgt cgcgatctgt attttcgcct gaacgtcctg 3000
acactcaagc ttcctccgct acgtaaccag tctgatcgca tagttcccct gttcacacgt 3060
tttacggccg ccgccgcgag ggagctcggt gttcccgttc ccgatgtttg cccactgctg 3120
cacaaagtgc tgctgggcca cgactggccc ggcaatatcc gtgagctcaa ggcggcagcc 3180
aaacgccatg tgctgggttt ccccttgctg ggcgccgagc cgcagggcga agagcacttg 3240
gcctgtgggc tcaaatcgca attgcgagtg atcgaaaaag ccctgattca ggagtcgctc 3300
aagcgccacg acaattgtgt ggattcggta agcctggaac tggacgtgcc acgccgtacg 3360
ctctatcgac gcatcaaaga attgcagatc taatgctgcc accgcaaaga ggagaaatac 3420
tagatgagtg tgatcgctaa acaaatgacc tacaaggttt atatgtcagg cacggtcaat 3480
ggacactact ttgaggtcga aggcgatgga aaaggtaagc cctacgaggg ggagcagacg 3540
gtaaagctca ctgtcaccaa gggcggacct ctgccatttg cttgggatat tttatcacca 3600
cagtgtcagt acggaagcat accattcacc aagtaccctg aagacatccc tgactatgta 3660
aagcagtcat tcccggaggg ctatacatgg gagaggatca tgaactttga agatggtgca 3720
gtgtgtactg tcagcaatga ttccagcatc caaggcaact gtttcatcta ccatgtcaag 3780
ttctctggtt tgaactttcc tcccaatgga cctgtcatgc agaagaagac acagggctgg 3840
gaacccaaca ctgagcgtct ctttgcacga gatggaatgc tgctaggaaa caactttatg 3900
gctctgaagt tagaaggagg cggtcactat ttgtgtgaat ttaaaactac ttacaaggca 3960
aagaagcctg tgaagatgcc agggtatcac tatgttgacc gcaaactgga tgtaaccaat 4020
cacaacaagg attacacttc ggttgagcag tgtgaaattt ccattgcacg caaacctgtg 4080
gtcgcctaat aatactagag ccaggcatca aataaaacga aaggctcagt cgaaagactg 4140
ggcctttcgt tttatctgtt gtttgtcggt gaacgctctc tactagagtc acactggctc 4200
accttcgggt gggcctttct gcgtttatat actagtagcg gccgctgcag tccggcaaaa 4260
aagggcaagg tgtcaccacc ctgccctttt tctttaaaac cgaaaagatt cgaaagcaaa 4320
ttcgacccgg tcgtcggttc agggcagggt cgttaaatag ccgcttatgt ctattgctgg 4380
tttaccggtt tattgactac cggaagcagt gtgaccgtgt gcttctcaaa tgcctgaggc 4440
cagtttgctc aggctctccc cgtggaggta ataattgacg atatgatcat ttattctgcc 4500
tcccagagcc tgataaaaac ggtgaatccg ttagcgaggt gccgccggct tccattcagg 4560
tcgaggtggc ccggctccat gcaccgcgac gcaacgcggg gaggcagaca aggtataggg 4620
cggcgaggcg gctacagccg atagtctgga acagcgcact tacgggttgc tgcgcaaccc 4680
aagtgctacc ggcgcggcag cgtgacccgt gtcggcggct ccaacggctc gccatcgtcc 4740
```

```
agaaaacacg gctcatcggg catcggcagg cgctgctgcc cgcgccgttc ccattcctcc  4800
gtttcggtca aggctggcag gtctggttcc atgcccggaa tgccgggctg gctgggcggc  4860
tcctcgccgg ggccggtcgg tagttgctgc tcgcccggat acagggtcgg gatgcggcgc  4920
aggtcgccat gccccaacag cgattcgtcc tggtcgtcgt gatcaaccac cacggcggca  4980
ctgaacaccg acaggcgcaa ctggtcgcgg ggctggcccc acgccacgcg gtcattgacc  5040
acgtaggccg acacggtgcc ggggccgttg agcttcacga cggagatcca gcgctcggcc  5100
accaagtcct tgactgcgta ttggaccgtc cgcaaagaac gtccgatgag cttggaaagt  5160
gtcttctggc tgaccaccac ggcgttctgg tggcccatct gcgccacgag gtgatgcagc  5220
agcattgccg ccgtgggttt cctcgcaata agcccggccc acgcctcatg cgctttgcgt  5280
tccgtttgca cccagtgacc gggcttgttc ttggcttgaa tgccgatttc tctggactgc  5340
gtggccatgc ttatctccat gcggtagggt gccgcacggt tgcggcacca tgcgcaatca  5400
gctgcaactt ttcggcagcg cgacaacaat tatgcgttgc gtaaaagtgg cagtcaatta  5460
cagattttct ttaacctacg caatgagcta ttgcgggggg tgccgcaatg agctgttgcg  5520
taccccccctt ttttaagttg ttgattttta agtctttcgc atttcgccct atatctagtt  5580
ctttggtgcc caaagaaggg cacccctgcg gggttccccc acgccttcgg cgcggctccc  5640
cctccggcaa aaagtggccc ctccggggct tgttgatcga ctgcgcggcc ttcggccttg  5700
cccaaggtgg cgctgccccc ttggaacccc cgcactcgcc gccgtgaggc tcggggggca  5760
ggcgggcggg cttcgccttc gactgccccc actcgcatag gcttgggtcg ttccaggcgc  5820
gtcaaggcca agccgctgcg cggtcgctgc gcgagccttg acccgccttc cacttggtgt  5880
ccaaccggca agcgaagcgc gcaggccgca ggccggaggc ttttccccag agaaaattaa  5940
aaaaattgat ggggcaaggc cgcaggccgc gcagttggag ccggtgggta tgtggtcgaa  6000
ggctgggtag ccggtgggca atccctgtgg tcaagctcgt gggcaggcgc agcctgtcca  6060
tcagcttgtc cagcagggtt gtccacgggc cgagcgaagc gagccagccg gtggccgctc  6120
gcggccatcg tccacatatc cacgggctgg caagggagcg cagcgaccgc gcagggcgaa  6180
gcccggagag caagcccgta gggcgccgca gccgccgtag gcggtcacga ctttgcgaag  6240
caaagtctag tgagtatact caagcattga gtggcccgcc ggaggcaccg ccttgcgctg  6300
cccccgtcga gccggttgga caccaaaagg gaggggcagg catggcggca tacgcgatca  6360
tgcgatgcaa gaagctggcg aaaatgggca acgtggcggc cagtctcaag cacgcctacc  6420
gcgagcgcga gacgcccaac gctgacgcca gcaggacgcc agagaacgag cactgggcgg  6480
ccagcagcac cgatgaagcg atgggccgac tgcgcgagtt gctgccagag aagcggcgca  6540
aggacgctgt gttggcggtc gagtacgtca tgacggccag cccggaatgg tggaagtcgg  6600
ccagccaaga acagcaggcg gcgttcttcg agaaggcgca caagtggctg gcggacaagt  6660
acggggcgga tcgcatcgtg acggccagca tccaccgtga cgaaaccagc ccgcacatga  6720
ccgcgttcgt ggtgccgctg acgcaggacg gcaggctgtc ggccaaggag ttcatcggca  6780
acaaagcgca gatgacccgc gaccagacca cgtttgcggc cgctgtggcc gatctagggc  6840
tgcaacgggg catcgagggc agcaaggcac gtcacacgcg cattcaggcg ttctacgagg  6900
ccctggagcg gccaccagtg ggccacgtca ccatcagccc gcaagcggtc gagccacgcg  6960
cctatgcacc gcagggattg gccgaaaagc tgggaatctc aaagcgcgtt gagacgccgg  7020
aagccgtggc cgaccggctg acaaaagcgg ttcggcaggg gtatgagcct gccctacagg  7080
ccgccgcagg agcgcgtgag atgcgcaaga aggccgatca agcccaagag acggcccgag  7140
accttcggga gcgcctgaag cccgttctgg acgccctggg gccgttgaat cgggatatgc  7200
aggccaaggc cgccgcgatc atcaaggccg tgggcgaaaa gctgctgacg gaacagcggg  7260
aagtccagcg ccagaaacag gcccagcgcc agcaggaacg cgggcgcgca catttccccg  7320
aaaagtgcca cctggatttt ggtcatgaga ttatcaaaaa ggatcttcac ctagatcctt  7380
ttaaattaaa aatgaagttt taaatcaatc taaagtatat atgagtaaac ttggtctgac  7440
agttaccaat gcttaatcag tgaggcacct atctcagcga tctgtctatt tcgttcatcc  7500
atagttgcct gactccccgt cgtgtagata actacgatac gggagggctt accatctggc  7560
cccagtgctg caatgatacc gcgagaccca cgctcaccgg ctccagattt atcagcaata  7620
aaccagccag ccggaagggc cgagcgcaga agtggtcctg caactttatc cgcctccatc  7680
cagtctatta attgttgccg ggaagctaga gtaagtagtt cgccagttaa tagtttgcgc  7740
aacgttgttg ccattgctac aggcatcgtg gtgtcacgct cgtcgtttgg tatggcttca  7800
ttcagctccg gttcccaacg atcaaggcga gttacatgat cccccatgtt gtgcaaaaaa  7860
gcggttagct ccttcggtcc tccgatcgtt gtcagaagta agttggccgc agtgttatca  7920
ctcatggtta tggcagcact gcataattct cttactgtca tgccatccgt aagatgcttt  7980
tctgtgactg gtgagtactc aaccaagtca ttctgagaat agtgtatgcg gcgaccgagt  8040
tgctcttgcc cggcgtcaat acgggataat accgcgccac atagcagaac tttaaaagtg  8100
ctcatcattg gaaaacgttc ttcggggcga aaactctcaa ggatcttacc gctgttgaga  8160
tccagttcga tgtaacccac tcgtgcaccc aactgatctt cagcatcttt tactttcacc  8220
agcgtttctg ggtgagcaaa aacaggaagg caaaatgccg caaaaaaggg aataagggcg  8280
acacggaaat gttgaatact catactcttc ctttttcaat attattgaag catttatcag  8340
ggttattgtc tcatgagcgg atacatattt gaatgggcaa atattatacg caaggcgaca  8400
aggtgctgat gccgctggcg attcaggttc atcatgccgt ttgtgatggc ttccatgtcg  8460
gcagaatgct taatgaatta caacagtttt tatgcatgcg cccaatacgc aaaccgcctc  8520
tgagagcgtt caccgac                                                 8537
```

SEQ ID NO: 12 moltype = DNA length = 11002
FEATURE Location/Qualifiers
source 1..11002
mol_type = other DNA
note = pBL_IMP_28 (hbpR ampl amilCP)
organism = synthetic construct

SEQUENCE: 12

```
aaacgtggtc tggtcgcggg tcatctgcgc tttgttgccg atgaactcct tggccgacag  60
cctgccgtcc tgcgtcagcg gcaccacgaa cgcggtcatg tgcgggctgg tttcgtcacg  120
gtggatgctg gccgtcacga tgcgatccgc cccgtacttg tccgccagcc acttgtgcgc  180
cttctcgaag aacgccgcct gctgttcttg gctggccgac ttccaccatt ccgggctggc  240
cgtcatgacg tactcgaccg ccaacacagc gtccttgcgc cgcttctctg gcagcaactc  300
gcgcagtcgg cccatcgctt catcggtgct gctggccgcc cagtgctcgt tctctggcgt  360
cctgctggcg tcagcgttgg gcgtctcgcg ctcgcggtag gcgtgcttga gactggccgc  420
```

-continued

```
cacgttgccc attttcgcca gcttcttgca tcgcatgatc gcgtatgccg ccatgcctgc  480
ccctcccttt tggtgtccaa ccggctcgac gggggcagcg caaggcggtg cctccggcgg  540
gccactcaat gcttgagtat actcactaga ctttgcttcg caaagtcgtg accgcctacg  600
gcggctgcgg cgccctacgg gcttgctctc cgggcttcgc cctgcgcggt cgctgcgctc  660
ccttgccagc ccgtggatat gtggacgatg gccgcgagcg gccaccggct ggctcgcttc  720
gctcggcccg tggacaaccc tgctggacaa gctgatggac aggctgcgcc tgcccacgag  780
cttgaccaca gggattgccc accggctacc cagccttcga ccacataccc accggctcca  840
actgcgcggc ctgcggcctt gccccatcaa ttttttaat tttctctggg gaaaagcctc  900
cggcctgcgg cctgcgcgct tcgcttgccg gttggacacc aagtggaagg cgggtcaagg  960
ctcgcgcagc gaccgcgcag cggcttggcc ttgacgcgcc tggaacgacc caagcctatg  1020
cgagtggggg cagtcgaagg cgaagcccgc ccgcctgccc cccgagcctc acggcggcga  1080
gtgcgggggt tccaaggggg cagcgccacc ttgggcaagg ccgaaggccg cgcagtcgat  1140
caacaagccc cggaggggcc actttttgcc ggagggggag ccgcgccgaa ggcgtggggg  1200
aaccccgcag gggtgccctt ctttgggcac caaagaacta gatatagggc gaaatgcgaa  1260
agacttaaaa atcaacaact taaaaaaggg gggtacgcaa cagctcattg cggcaccccc  1320
cgcaatagct cattgcgtag gttaaagaaa atctgtaatt gactgccact tttacgcaac  1380
gcataattgt tgtcgcgctg ccgaaaagtt gcagctgatt gcgcatggtg ccgcaaccgt  1440
gcggcaccct accgcatgga gataagcatg gccacgcagt ccagagaaat cggcattcaa  1500
gccaagaaca agcccggtca ctgggtgcaa acggaacgca aagcgcatga ggcgtgggcc  1560
gggcttattg cgaggaaacc cacggcggca atgctgctgc atcacctcgt ggcgcagatg  1620
ggccaccaga acgccgtggt ggtcagccag aagacacttt ccaagctcat cggacgttct  1680
ttgcggacgg tccaatacgc agtcaaggac ttggtggccg agcgctggat ctccgtcgtg  1740
aagctcaacg gccccggcac cgtgtcggcc tacgtggtca atgaccgcgt ggcgtggggc  1800
cagccccgcg accagttgcg cctgtcggtg ttcagtgccg ccgtggtggt tgatcacgac  1860
gaccaggacg aatcgctgtt ggggcatggc gacctgcgcc gcatcccgac cctgtatccg  1920
ggcgagcagc aactaccgac cggccccggc gaggagccgc ccagccagcc cggcattccg  1980
ggcatggaac cagacctgcc agccttgacc gaaacggagg aatgggaacg gcgcgggcag  2040
cagcgcctgc cgatgcccga tgagccgtgt tttctggacg atggcgagcc gttggagccg  2100
ccgacacggg tcacgctgcc gcgccggtag cacttgggtt gcgcagcaac ccgtaagtgc  2160
gctgttccag actatcggct gtagccgcct cgccgcccta taccttgtct gcctccccgc  2220
gttgcgtcgc ggtgcatgga gccgggccac ctcgacctga atggaagccg gcggcacctc  2280
gctaacggat tcaccgtttt tatcaggctc tgggaggcag aataaatgat catatgagag  2340
cgttcaccga caaacaacag ataaaacgaa aggcccagtc tttcgactga gcctttcgtt  2400
ttatttgaag agctactctc gctcttcctc ctatgtgatc tttttgacgc ggtaatcaag  2460
ccgggctcga gttatcccaa gaagggaggc cgcccgggaa atattgccac cgctatgttt  2520
gacagctgct cgggtgatgg cgtcttgaac ctggtccagg ttaatagacc cttgatgcac  2580
catctgctcg gcaaactcat ctaatgagag aactttaggg ttggcgttct cagccgcgtt  2640
ccgtattagc tcgctgctca aggtcaaatc acctttctgg ttaagactca ggaagtcttg  2700
tgtagtgagg gtgccttcaa ttgtcgttaa atggtgggtg tccaaaaaat cgacgtcttg  2760
agccatgatt atggctctct caatcacgtt ctccaattct cgaatattgc ctggccagtc  2820
atggtagata agtacctgca tggcggcaga cgatatgcct tttaacttac gtccgtggcg  2880
tttagaaaat cgagcgatga gtacgctggt aatgagtgaa atatcatcgc ggcgttctcg  2940
cagaggggga atctggatgg gaaagacgtt cagtcgatag taaagatcct ctcggaagtg  3000
accatcttgg acagcttttt tcagatcagc gttcgtggcg gcaatcagtc ggacactggt  3060
gtggattgtc cggttgctac cgagacgttc caattcgcca ttctgcaata cacggagaag  3120
tttactttga gcggtcatac tgagggtggc aatttcgtca aggaagagag tgccttgatg  3180
agccgcctcg aaacgcccct ctcgcgtagc ggtcgcacct gtaaaggctc cgcgctctac  3240
gccgaacagc tccgactcga ttaattgatc gggtatagcg gcacagttca cttcgacgaa  3300
agcttggtcg gcgcggttgc tcaaacggtg gatctcgcgt gcaataaggc tcttgccgct  3360
cccactttct ccaagtaaaa gaacagtcgc atcagtctct gccacacagg ctgttttgtg  3420
acggagcacc ttgaacactg ccgacgaacc aatgacgagc tcgccgccct gatcatcatc  3480
gggaataggg tgcgtggtga tctgggattg ctccgactga ctgagcgccc acatttcggc  3540
gggcttcgct tgaatacggc aatgagtgtg tcccatcgct tggcattcga tctcttccac  3600
gacaatgggt tttccagcgc atgcgctcag gtaccctgag caatacgcaa cggaaaacca  3660
acataccgca tgtgaactga caccatgcat cgctaagtga atttcagctt cgatgctgtt  3720
ctgccagtat gcctccgcat gataatccat gctcttcata tcgaccgcat ttagcgccga  3780
tgatccagct tgtatagatg ttagaaaccc ttgcaaggcg tgcaagacac cacctgcata  3840
aatctgttct ttgatagagg atataccttg ttttttttata atcatttctg catcgcgttg  3900
gccggtggtg aagccgatac gagtcaaaaa ctcccgcgtg tagtctgggc cagaataggc  3960
ctgcaattcc ttgtatatat ccttcagtgt ctccacttgt aggagcaggc atcggctttc  4020
gtccagccag atacgtcctt cgttgggaga aaagtgcagc ttggaaacta aagcatggac  4080
ttcggggagc gcaaggtcgg caacgatgga gcgatcgtcg ctattatttt tatttgattt  4140
catggcgatg gttcaggtcc ggtaggaata gatgagggtc tcgttgggtt taataatttt  4200
attaaattgt ggtggtggga ttcagaatat ggtgaaacca gctcgtccga gcaggcgcat  4260
tctggcatct gccgacggat ccatattccc ttcagtctta ctgtgtgtag gtgcatggat  4320
cgggctgtcg cctagccaga tgcgtccttc gttgtgggga gggaatgcag accgaacgcc  4380
gaaacatgga tttcagggcg cgatagatcg gcaacgatgg tgcggttttc atggttctta  4440
tttttgttag atttcatggt gatagctcat gccaggtagg agtagatagg gttctcgtag  4500
atttaataaa tttatgaaat cgtggttgtg agttttcata atatggtgaa gcttgcccgc  4560
catggcaagt gcatttcggc agctgttggc gaccgcggaa ggggtttaca gccgtctgga  4620
gctaggcttt ctggcgctca ttaaaataaa aatccttata aaacagtatc ctagctttta  4680
tgtctgaggc tgcttagtca acctggcacg gtactggcta cgagtcccgc aaggcagccg  4740
tgagttcgac tgtactgctg cctattaaaa caatatgaac gcggagacgt gataacaatg  4800
agtacaggca tcgataagga cgtccgagag tgttggggcg taactgcatt atcagcgggt  4860
catcaaattg caatgaatag cgcgtttctg gatatggact tgctgttgtg cggggaaacc  4920
ggcaccggca aggacacact ggccaaccgc attcacgagt tgtccagcag gtcgggaccc  4980
tttgtgggca tgaactgcgc cgccattccc gagtcgctgg cagagagcca gttattcggt  5040
gtggtcaacg gtgcattcac cggcgtatgc cgggctcgcg agggctacat agaggcctcc  5100
agtggtggca ccttgtacct ggatgaaatc gacagcatgc cgttgagcct gcaagccaaa  5160
```

```
ctgctgcgtg tgttggagag tcgaggtatc gagcgtctgg gctcgaccga atttatcccg  5220
gtggatctgc ggatcattgc ctcggcccag cggccactgg atgaactggt ggaacaagga  5280
cttttccgtc gcgacctgtt ttttcggctc aacgtgctga cgcttcactt gccagccttg  5340
cgcaaacgtc gtgaacagat cctgccattg ttcgaccagt tcacccaggg tatcgctgcc  5400
gagttcggac gtcccgctcc tgcgctggac agcgggcgtg tgcagctgct gctcagccac  5460
gactggccgg gcaacatccg cgaattgaag tctgcggcca agcgcttcgt actcggcttc  5520
cccttgctgg gcgccgaccc tgtggaagcg cttgaccctg ccacggggct gcgcacgcaa  5580
atgcgcatca tcgagaaaat gctcatccag gatgccttga agcggcacag gcacaatttc  5640
gacgcggtgc ttcaggagtt ggagttgcca agacgcaccc tgtatcaccg catgaaggaa  5700
ctgggagttg cagcgccgat cgctgcgacg gccggggtct aataaccagg catcaaagag  5760
gagaaaatga gtcttgatga aaggtttgag gatgatctgg acgaggagcg ggttccgaat  5820
ctggggatag ttgccgaaag tatttcgcaa ctgggtatcg acgtgctgct atcgggtgag  5880
accggcacgg gcaaagacac gattgcccga cggattcatg agatgtcagg ccgcaaaggg  5940
cgcctggtgg cgatgaattg cgcggccatt ccggagtccc tcgccgagag cgagttattc  6000
ggcgtggtca gcggtgccta caccggcgct gatcgctcca gagtcggtta tgtcgaagcg  6060
gcgcagggcg gcacgctgta cctggatgag atcgatagca tgccgctgag cctgcaagcc  6120
aaattgctga gggtgctgga aacccgagcg cttgaacggc tgggttcgac gtcgacgatc  6180
aagctggata tctgcgtgat cgcctccgcc caatgctcgc tggacgacgc cgtcgagcgg  6240
gggcagtttc gtcgcgatct gtattttcgc ctgaacgtcc tgacactcaa gcttcctccg  6300
ctacgtaacc agtctgatcg catagttccc ctgttcacac gttttacggc cgccgccgcg  6360
agggagctcg gtgttcccgt tcccgatgtt tgcccactgc tgcacaaagt gctgctgggc  6420
cacgactggc ccggcaatat ccgtgagctc aaggcggcag ccaaacgcca tgtgctgggt  6480
ttccccttgc tgggcgccga gccgcagggc gaagagcact tggcctgtgg gctcaaatcg  6540
caattgcgag tgatcgaaaa agccctgatt caggagtcgc tcaagcgcca cgacaattgt  6600
gtggattcgg taagcctgga actggacgtg ccacgccgta cgctctatcg acgcatcaaa  6660
gaattgcaga tctaatgctg ccaccgcaaa gaggagaaat actagatgag tgtgatcgct  6720
aaacaaatga cctacaaggt ttatatgtca ggcacggtca atggacacta ctttgaggtc  6780
gaaggcgatg gaaaaggtaa gccctacgag gggggagcaga cggtaaagct cactgtcacc  6840
aagggcggac ctctgccatt tgcttgggat attttatcac cacagtgtca gtacggaagc  6900
ataccattca ccaagtaccc tgaagacatc cctgactatg taaagcagtc attcccggag  6960
ggctatacat gggagaggat catgaacttt gaagatggtg cagtgtgtac tgtcagcaat  7020
gattccagca tccaaggcaa ctgtttcatc taccatgtca agttctctgg tttgaacttt  7080
cctcccaatg gacctgtcat gcagaagaag acacagggct gggaacccaa cactgagcgt  7140
ctctttgcac gagatggaat gctgctagga aacaacttta tggctctgaa gttagaagga  7200
ggcggtcact atttgtgtga atttaaaact acttacaagg caaagaagcc tgtgaagatg  7260
ccagggtatc actatgttga ccgcaaactg gatgtaacca atcacaacaa ggattacact  7320
tcggttgagc agtgtgaaat ttccattgca cgcaaacctg tggtcgccta ataatactag  7380
agccaggcat caaataaaac gaaaggctca gtcgaaagac tgggcctttc gttttatctg  7440
ttgtttgtcg gtgaacgctc tctactagag tcacactggc tcaccttcgg gtgggccttt  7500
ctgcgtttat atactagtag cggccgctgc agtccggcaa aaaagggcaa ggtgtcacca  7560
ccctgccctt tttctttaaa accgaaaaga tgttaaaatt cgcgttaaat ttttgttaaa  7620
tcagctcatt ttttaaccaa taggccgact gcgatgagtg gcagggcggg gcgtaatttt  7680
tttaaggcag ttattggtgc ccttaaacgc ctggtgctac gcctgaataa gtgataataa  7740
gcggatgaat ggcagaaatt cgaaagcaaa ttcgacccgg tcgtcggttc agggcagggt  7800
cgttaaatag ccgcttatgt ctattgctgg tttaccggtt tattgactac cggaagcagt  7860
gtgaccgtgt gcttctcaaa tgcctgaggc cagtttgctc aggctctccc cgtggaggta  7920
ataattgacg cagtcgataa gcccggatca gcttgcaatt cgcgcgcgaa ggcgaagcgg  7980
catttacgtt gacaccatcg aatggtgcaa aacctttcgc ggtatggcat gatagcgccc  8040
ggaagagagt caattcaggg tggtgaatgt gaaaccagta acgttatacg atgtcgcaga  8100
gtatgccggt gtctcttatc agaccgtttc ccgcgtggtg aaccaggcca gccacgtttc  8160
tgcgaaaacg cgggaaaaag tggaagcggc gatggcggag ctgaattaca ttcccaaccg  8220
cgtggcacaa caactggcgg gcaaacagtc gttgctgatt ggcgttgcca cctccagtct  8280
ggccctgcac gcgccgtcgc aaattgtcgc ggcgattaaa tctcgcgccg atcaactggg  8340
tgccagcgtg gtggtgtcga tggtagaacg aagcggcgtc gaagcctgta aagcggcggt  8400
gcacaatctt ctcgcgcaac gcgtcagtgg gctgatcatt aactatccgc tggatgacca  8460
ggatgccatt gctgtggaag ctgcctgcac taatgttccg gcgttatttc ttgatgtctc  8520
tgaccagaca cccatcaaca gtattatttt ctcccatgaa gacggtacgc gactgggcgt  8580
ggagcatctg gtcgcattgg gtcaccagca aatcgcgctg ttagcgggcc cattaagttc  8640
tgtctcggcg cgtctgcgtc tggctggctg gcataaatat ctcactcgca atcaaattca  8700
gccgatagcg gaacgggaag gcgactggag tgccatgtcc ggttttcaac aaaccatgca  8760
aatgctgaat gagggcatcg ttcccactgc gatgctggtt gccaacgatc agatggcgct  8820
gggcgcaatg cgcgccatta ccgagtccgg gctgcgcgtt ggtgcggata tctcggtagt  8880
gggatacgac gataccgaag acagctcatg ttatatcccg ccgttaacca ccatcaaaca  8940
ggattttcgc ctgctggggc aaaccagcgt ggaccgcttg ctgcaactct ctcagggcca  9000
ggcggtgaag ggcaatcagc tgttgcccgt ctcactggtg aaaagaaaaa ccaccctggc  9060
gcccaatacg caaaccgcct ctccccgcgc gttggccgat tcattaatgc agctggcacg  9120
acaggtttcc cgactggaaa gcgggcagtg agcgcaacgc aattaatgta agttagcgcg  9180
aattgcaagc tggccgacgc gctgggctac gtcttgctgc gttgcgctca ctgcccgctt  9240
tccagtcggg aaacctgtcg tgccagctgc attaatgaat cggccaacgc gcggggagag  9300
gcggtttgcg tattgggcgc atgcataaaa actgttgtaa ttcattaagc attctgccga  9360
catggaagcc atcacaaacg gcatgatgaa cctgaatcgc cagcggcatc agcaccttgt  9420
cgccttgcgt ataatatttg cccattcaaa tatgtatccg ctcatgagac aataaccctg  9480
ataaatgctt caataatatt gaaaaaggaa gagtatgagt attcaacatt tccgtgtcgc  9540
ccttattccc ttttttgcgg cattttgcct tcctgttttt gctcacccag aaacgctggt  9600
gaaagtaaaa gatgctgaag atcagttggg tgcacgagtg ggttacatcg aactggatct  9660
caacagcggt aagatccttg agagttttcg ccccgaagaa cgttttccaa tgatgagcac  9720
ttttaaagtt ctgctatgtg gcgcggtatt atcccgtatt gacgccgggc aagagcaact  9780
cggtcgccgc atacactatt ctcagaatga cttggttgag tactcaccag tcacagaaaa  9840
gcatcttacg gatggcatga cagtaagaga attatgcagt gctgccataa ccatgagtga  9900
```

```
taacactgcg gccaacttac ttctgacaac gatcggagga ccgaaggagc taaccgcttt  9960
tttgcacaac atgggggatc atgtaactcg ccttgatcgt tgggaaccgg agctgaatga  10020
agccatacca aacgacgagc gtgacaccac gatgcctgta gcaatggcaa caacgttgcg  10080
caaactatta actggcgaac tacttactct agcttcccgg caacaattaa tagactggat  10140
ggaggcggat aaagttgcag gaccacttct gcgctcggcc cttccggctg gctggtttat  10200
tgctgataaa tctggagccg gtgagcgtgg gtctcgcggt atcattgcag cactggggcc  10260
agatggtaag ccctcccgta tcgtagttat ctacacgacg gggagtcagg caactatgga  10320
tgaacgaaat agacagatcg ctgagatagg tgcctcactg attaagcatt ggtaactgtc  10380
agaccaagtt tactcatata tactttagat tgatttaaaa cttcattttt aatttaaaag  10440
gatctaggtg aagatccttt ttgataatct catgaccaaa atccaggtgg cacttttcgg  10500
ggaaatgtgc gcgcccgcgt tcctgctggc gctgggcctg tttctggcgc tggacttccc  10560
gctgttccgt cagcagcttt tcgcccacgg ccttgatgat cgcggcggcc ttggcctgca  10620
tatcccgatt caacggcccc agggcgtcca gaacgggctt caggcgctcc cgaaggtctc  10680
gggccgtctc ttgggcttga tcggccttct tgcgcatctc acgcgctcct gcggcggcct  10740
gtagggcagg ctcatacccc tgccgaaccg cttttgtcag ccggtcggcc acggcttccg  10800
gcgtctcaac gcgctttgag attcccagct tttcggccaa tccctgcggt gcataggcgc  10860
gtggctcgac cgcttgcggg ctgatggtga cgtggcccac tggtggccgc tccagggcct  10920
cgtagaacgc ctgaatgcgc gtgtgacgtg ccttgctgcc ctcgatgccc cgttgcagcc  10980
ctagatcggc cacagcggcc gc                                            11002

SEQ ID NO: 13           moltype = DNA  length = 8912
FEATURE                 Location/Qualifiers
source                  1..8912
                        mol_type = other DNA
                        note = pBL_IMP_31 (hbpR amilCP)
                        organism = synthetic construct
SEQUENCE: 13
aaacgtggtc tggtcgcggg tcatctgcgc tttgttgccg atgaactcct tggccgacag  60
cctgccgtcc tgcgtcagcg gcaccacgaa cgcggtcatg tgcgggctgg tttcgtcacg  120
gtggatgctg gccgtcacga tgcgatccgc cccgtacttg tccgccagcc acttgtgcgc  180
cttctcgaag aacgccgcct gctgttcttg gctggccgac ttccaccatt ccgggctggc  240
cgtcatgacg tactcgaccg ccaacacagc gtccttgcgc cgcttctctg gcagcaactc  300
gcgcagtcgg cccatcgctt catcggtgct gctggccgcc cagtgctcgt tctctggcgt  360
cctgctggcg tcagcgttgg gcgtctcgcg ctcgcggtag gcgtgcttga gactggccgc  420
cacgttgccc attttcgcca gcttcttgca tcgcatgatc gcgtatgccg ccatgcctgc  480
ccctcccttt tggtgtccaa ccggctcgac gggggcagcg caaggcggtg cctccggcgg  540
gccactcaat gcttgagtat actcactaga ctttgcttcg caaagtcgtg accgcctacg  600
gcggctgcgg cgccctacgg gcttgctctc cgggcttcgc cctgcgcggt cgctgcgctc  660
ccttgccagc ccgtggatat gtggacgatg gccgcgagcg gccaccggct ggctcgcttc  720
gctcggcccg tggacaaccc tgctggacaa gctgatggac aggctgcgcc tgcccacgag  780
cttgaccaca gggattgccc accggctacc cagccttcga ccacataccc accggctcca  840
actgcgcggc ctgcggcctt gccccatcaa ttttttttaat tttctctggg gaaaagcctc  900
cggcctgcgg cctgcgcgct tcgcttgccg gttggacacc aagtggaagg cgggtcaagg  960
ctcgcgcagc gaccgcgcag cggcttggcc ttgacgcgcc tggaacgacc caagcctatg  1020
cgagtggggg cagtcgaagg cgaagcccgc ccgcctgccc cccgagcctc acggcggcga  1080
gtgcgggggt tccaaggggg cagcgccacc ttgggcaagg ccgaaggccg cgcagtcgat  1140
caacaagccc cggaggggcc acttttttgcc ggagggggag ccgcgccgaa ggcgtggggg  1200
aaccccgcag gggtgccctt ctttgggcac caaagaacta gatataggc gaaatgcgaa  1260
agacttaaaa atcaacaact taaaaaaggg gggtacgcaa cagctcattg cggcaccccc  1320
cgcaatagct cattgcgtag gttaaagaaa atctgtaatt gactgccact tttacgcaac  1380
gcataattgt tgtcgcgctg ccgaaaagtt gcagctgatt gcgcatggtg ccgcaaccgt  1440
gcggcaccct accgcatgga gataagcatg gccacgcagt ccagagaaat cggcattcaa  1500
gccaagaaca agcccggtca ctgggtgcaa acggaacgca aagcgcatga ggcgtgggcc  1560
gggcttattg cgaggaaacc cacggcggca atgctgctgc atcacctcgt ggcgcagatg  1620
ggccaccaga acgccgtggt ggtcagccag aagacacttt ccaagctcat cggacgttct  1680
ttgcggacgg tccaatacgc agtcaaggac ttggtggccg agcgctggat ctccgtcgtg  1740
aagctcaacg gccccggcac cgtgtcggcc tacgtggtca atgaccgcgt ggcgtggggc  1800
cagccccgcg accagttgcg cctgtcggtg ttcagtgccg ccgtggtggt tgatcacgac  1860
gaccaggacg aatcgctgtt ggggcatggc gacctgcgcc gcatcccgac cctgtatccg  1920
ggcgagcagc aactaccgac cggcccccggc gaggagccgc ccagccagcc cggcattccg  1980
ggcatggaac cagacctgcc agccttgacc gaaacggagg aatgggaacg gcgcgggcag  2040
cagcgcctgc cgatgcccga tgagccgtgt tttctggacg atggcgagcc gttggagccg  2100
ccgacacggg tcacgctgcc gcgccggtag cacttgggtt gcgcagcaac ccgtaagtgc  2160
gctgttccag actatcggct gtagccgcct cgccgcccta taccttgtct gcctccccgc  2220
gttgcgtcgc ggtgcatgga gccgggccac ctcgacctga atggaagccg gcggcacctc  2280
gctaacggat tcaccgtttt tatcaggctc tgggaggcag aataaatgat catatgagag  2340
cgttcaccga caaacaacag ataaaacgaa aggcccagtc tttcgactga gcctttcgtt  2400
ttatttgaag agctactctc gctcttcctc ctatgtgatc tttttgacgc ggtaatcaag  2460
ccgggctcga gttatcccaa gaagggaggc cgcccgggaa atattgccac cgctatgttt  2520
gacagctgct cgggtgatgg cgtcttgaac ctggtccagg ttaatagacc cttgatgcac  2580
catctgctcg gcaaactcat ctaatgagag aactttaggg ttggcgttct cagccgcgtt  2640
ccgtattagc tcgctgctca aggtcaaatc acctttctgg ttaagactca ggaagtcttg  2700
tgtagtgagg gtgccttcaa ttgtcgttaa atggtgggtg tccaaaaaat cgacgtcttg  2760
agccatgatt atggctctct caatcacgtt ctccaattct cgaatattgc ctggccagtc  2820
atggtagata agtacctgca tggcggcaga cgatatgcct tttaacttac gtccgtggcg  2880
tttagaaaat cgagcgatga gtacgctggt aatgagtgaa atatcatcgc ggcgttctcg  2940
cagaggggga atctggatgg gaaagacgtt cagtcgatag taaagatcct ctcggaagtg  3000
accatcttgg acagcttttt tcagatcagc gttcgtggcg gcaatcagtc ggacactggt  3060
gtggattgtc cggttgctac cgagacgttc caattcgcca ttctgcaata cacggagaag  3120
```

```
tttactttga gcggtcatac tgagggtggc aatttcgtca aggaagagag tgccttgatg  3180
agccgcctcg aaacgcccct ctcgcgtagc ggtcgcacct gtaaaggctc cgcgctctac  3240
gccgaacagc tccgactcga ttaattgatc gggtatagcg gcacagttca cttcgacgaa  3300
agcttggtcg gcgcggttgc tcaaacggtg gatctcgcgt gcaataaggc tcttgccgct  3360
cccactttct ccaagtaaaa gaacagtcgc atcagtctct gccacacagg ctgttttgtg  3420
acggagcacc ttgaacactg ccgacgaacc aatgacgagc tcgccgccct gatcatcatc  3480
gggaataggg tgcgtggtga tctgggattg ctccgactga ctgagcgccc acatttcggc  3540
gggcttcgct tgaatacggc aatgagtgtg tcccatcgct tggcattcga tctcttccac  3600
gacaatgggt tttccagcgc atgcgctcag gtaccctgag caatacgcaa cggaaaacca  3660
acataccgca tgtgaactga caccatgcat cgctaagtga atttcagctt cgatgctgtt  3720
ctgccagtat gcctccgcat gataatccat gctcttcata tcgaccgcat ttagcgccga  3780
tgatccagct tgtatagatg ttagaaaccc ttgcaaggcg tgcaagacac cacctgcata  3840
aatctgttct ttgatagagg atataccttg tttttttata atcatttctg catcgcgttg  3900
gccggtggtg aagccgatac gagtcaaaaa ctcccgcgtg tagtctgggc cagaataggc  3960
ctgcaattcc ttgtatatat ccttcagtgt ctccacttgt aggagcaggc atcggctttc  4020
gtccagccag atacgtcctt cgttgggaga aaagtgcagc ttggaaacta aagcatggac  4080
ttcggggagc gcaaggtcgg caacgatgga gcgatcgtcg ctattatttt tatttgattt  4140
catggcgatg gttcaggtcc ggtaggaata gatgagggtc tcgttgggtt taataatttt  4200
attaaattgt ggtggtggga ttcagaatat ggtgaaacca gctcgtccga gcaggcgcat  4260
tctggcatct gccgacggat ccatattccc ttcagtctta ctgtgtgtag gtgcatggat  4320
cgggctgtcg cctagccaga tgcgtccttc gttgtgggga gggaatgcag accgaacgcc  4380
gaaacatgga tttcagggcg cgatagatcg gcaacgatgg tgcggttttc atggttctta  4440
tttttgttag atttcatggt gatagctcat gccaggtagg agtagatagg gttctcgtag  4500
atttaataaa tttatgaaat cgtggttgtg agttttcata atatggtgaa gcttgcccgc  4560
catggcaagt gcatttcggc agctgttggc gaccgcggaa ggggtttaca gccgtctgga  4620
gctaggcttt ctggcgctca ttaaaataaa aatccttata aaacagtatc ctagctttta  4680
tgtctgaggc tgcttagtca acctggcacg gtactggcta cgagtcccgc aaggcagccg  4740
tgagttcgac tgtactgctg cctattaaaa caatatgaac gcggagacgt gataacaatg  4800
agtgtgatcg ctaaacaaat gacctacaag gtttatatgt caggcacggt caatggacac  4860
tactttgagg tcgaaggcga tggaaaaggt aagccctacg agggggagca gacggtaaag  4920
ctcactgtca ccaagggcgg acctctgcca tttgcttggg atattttatc accacagtgt  4980
cagtacggaa gcataccatt caccaagtac cctgaagaca tccctgacta tgtaaagcag  5040
tcattcccgg agggctatac atgggagagg atcatgaact ttgaagatgg tgcagtgtgt  5100
actgtcagca atgattccag catccaaggc aactgtttca tctaccatgt caagttctct  5160
ggtttgaact ttcctcccaa tggacctgtc atgcagaaga agacacaggg ctgggaaccc  5220
aacactgagc gtctctttgc acgagatgga atgctgctag gaaacaactt tatggctctg  5280
aagttagaag gaggcggtca ctatttgtgt gaatttaaaa ctacttacaa ggcaaagaag  5340
cctgtgaaga tgccagggta tcactatgtt gaccgcaaac tggatgtaac caatcacaac  5400
aaggattaca cttcggttga gcagtgtgaa atttccattg cacgcaaacc tgtggtcgcc  5460
taataagaat ggcgaatgga aattgtaagc gttaatattt tgttaaaatt cgcgttaaat  5520
ttttgttaaa tcagctcatt ttttaaccaa taggccgact gcgatgagtg gcagggcggg  5580
gcgtaatttt tttaaggcag ttattggtgc ccttaaacgc ctggtgctac gcctgaataa  5640
gtgataataa gcggatgaat ggcagaaatt cgaaagcaaa ttcgacccgg tcgtcggttc  5700
agggcagggt cgttaaatag ccgcttatgt ctattgctgg tttaccggtt tattgactac  5760
cggaagcagt gtgaccgtgt gcttctcaaa tgcctgaggc cagtttgctc aggctctccc  5820
cgtggaggta ataattgacg cagtcgataa gcccggatca gcttgcaatt cgcgcgcgaa  5880
ggcgaagcgg catttacgtt gacaccatcg aatggtgcaa aacctttcgc ggtatggcat  5940
gatagcgccc ggaagagagt caattcaggg tggtgaatgt gaaaccagta acgttatacg  6000
atgtcgcaga gtatgccggt gtctcttatc agaccgtttc ccgcgtggtg aaccaggcca  6060
gccacgtttc tgcgaaaacg cgggaaaaag tggaagcggc gatggcggag ctgaattaca  6120
ttcccaaccg cgtggcacaa caactggcgg gcaaacagtc gttgctgatt ggcgttgcca  6180
cctccagtct ggccctgcac gcgccgtcgc aaattgtcgc ggcgattaaa tctcgcgccg  6240
atcaactggg tgccagcgtg gtggtgtcga tggtagaacg aagcggcgtc gaagcctgta  6300
aagcggcggt gcacaatctt ctcgcgcaac gcgtcagtgg gctgatcatt aactatccgc  6360
tggatgacca ggatgccatt gctgtggaag ctgcctgcac taatgttccg gcgttatttc  6420
ttgatgtctc tgaccagaca cccatcaaca gtattatttt ctcccatgaa gacggtacgc  6480
gactgggcgt ggagcatctg gtcgcattgg gtcaccagca aatcgcgctg ttagcgggcc  6540
cattaagttc tgtctcggcg cgtctgcgtc tggctggctg gcataaatat ctcactcgca  6600
atcaaattca gccgatagcg gaacgggaag gcgactggag tgccatgtcc ggttttcaac  6660
aaaccatgca aatgctgaat gagggcatcg ttcccactgc gatgctggtt gccaacgatc  6720
agatggcgct gggcgcaatg cgcgccatta ccgagtccgg gctgcgcgtt ggtgcggata  6780
tctcggtagt gggatacgac gataccgaag acagctcatg ttatatcccg ccgttaacca  6840
ccatcaaaca ggattttcgc ctgctggggc aaaccagcgt ggaccgcttg ctgcaactct  6900
ctcagggcca ggcggtgaag ggcaatcagc tgttgcccgt ctcactggtg aaaagaaaaa  6960
ccaccctggc gcccaatacg caaaccgcct ctccccgcgc gttggccgat tcattaatgc  7020
agctggcacg acaggtttcc cgactggaaa gcgggcagtg agcgcaacgc aattaatgta  7080
agttagcgcg aattgcaagc tggccgacgc gctgggctac gtcttgctgc gttgcgctca  7140
ctgcccgctt tccagtcggg aaacctgtcg tgccagctgc attaatgaat cggccaacgc  7200
gcggggagag gcggtttgcg tattgggcgc atgcataaaa actgttgtaa ttcattaagc  7260
attctgccga catggaagcc atcacaaacg gcatgatgaa cctgaatcgc cagcggcatc  7320
agcaccttgt cgccttgcgt ataatatttg cccattcaaa tatgtatccg ctcatgagac  7380
aataaccctg ataaatgctt caataatatt gaaaaaggaa gagtatgagt attcaacatt  7440
tccgtgtcgc ccttattccc ttttttgcgg cattttgcct tcctgttttt gctcacccag  7500
aaacgctggt gaaagtaaaa gatgctgaag atcagttggg tgcacgagtg ggttacatcg  7560
aactggatct caacagcggt aagatccttg agagttttcg ccccgaagaa cgttttccaa  7620
tgatgagcac ttttaaagtt ctgctatgtg gcgcggtatt atcccgtatt gacgccgggc  7680
aagagcaact cggtcgccgc atacactatt ctcagaatga cttggttgag tactcaccag  7740
tcacagaaaa gcatcttacg gatggcatga cagtaagaga attatgcagt gctgccataa  7800
ccatgagtga taacactgcg gccaacttac ttctgacaac gatcggagga ccgaaggagc  7860
```

```
taaccgcttt tttgcacaac atgggggatc atgtaactcg ccttgatcgt tgggaaccgg  7920
agctgaatga agccatacca aacgacgagc gtgacaccac gatgcctgta gcaatggcaa  7980
caacgttgcg caaactatta actggcgaac tacttactct agcttcccgg caacaattaa  8040
tagactggat ggaggcggat aaagttgcag gaccacttct gcgctcggcc cttccggctg  8100
gctggtttat tgctgataaa tctggagccg gtgagcgtgg gtctcgcggt atcattgcag  8160
cactggggcc agatggtaag ccctcccgta tcgtagttat ctacacgacg gggagtcagg  8220
caactatgga tgaacgaaat agacagatcg ctgagatagg tgcctcactg attaagcatt  8280
ggtaactgtc agaccaagtt tactcatata tactttagat tgatttaaaa cttcattttt  8340
aatttaaaag gatctaggtg aagatccttt ttgataatct catgaccaaa atccaggtgg  8400
cacttttcgg ggaaatgtgc gcgcccgcgt tcctgctggc gctgggcctg tttctggcgc  8460
tggacttccc gctgttccgt cagcagcttt tcgcccacgg ccttgatgat cgcggcggcc  8520
ttggcctgca tatcccgatt caacggcccc agggcgtcca gaacgggctt caggcgctcc  8580
cgaaggtctc gggccgtctc ttgggcttga tcggccttct tgcgcatctc acgcgctcct  8640
gcggcggcct gtagggcagg ctcatacccc tgccgaaccg cttttgtcag ccggtcggcc  8700
acggcttccg gcgtctcaac gcgctttgag attcccagct tttcggccaa tccctgcggt  8760
gcataggcgc gtggctcgac cgcttgcggg ctgatggtga cgtggcccac tggtggccgc  8820
tccagggcct cgtagaacgc ctgaatgcgc gtgtgacgtg ccttgctgcc ctcgatgccc  8880
cgttgcagcc ctagatcggc cacagcggcc gc                               8912

SEQ ID NO: 14          moltype = DNA  length = 10660
FEATURE                Location/Qualifiers
source                 1..10660
                       mol_type = other DNA
                       note = pBL_IMP_32 (hbpR ampl lacZ)
                       organism = synthetic construct
SEQUENCE: 14
aaacgtggtc tggtcgcggg tcatctgcgc tttgttgccg atgaactcct tggccgacag  60
cctgccgtcc tgcgtcagcg gcaccacgaa cgcggtcatg tgcgggctgg tttcgtcacg  120
gtggatgctg gccgtcacga tgcgatccgc cccgtacttg tccgccagcc acttgtgcgc  180
cttctcgaag aacgccgcct gctgttcttg gctggccgac ttccaccatt ccgggctggc  240
cgtcatgacg tactcgaccg ccaacacagc gtccttgcgc cgcttctctg gcagcaactc  300
gcgcagtcgg cccatcgctt catcggtgct gctggccgcc cagtgctcgt tctctggcgt  360
cctgctggcg tcagcgttgg gcgtctcgcg ctcgcggtag gcgtgcttga gactggccgc  420
cacgttgccc attttcgcca gcttcttgca tcgcatgatc gcgtatgccg ccatgcctgc  480
ccctcccttt tggtgtccaa ccggctcgac gggggcagcg caaggcggtg cctccggcgg  540
gccactcaat gcttgagtat actcactaga ctttgcttcg caaagtcgtg accgcctacg  600
gcggctgcgg cgccctacgg gcttgctctc cgggcttcgc cctgcgcggt cgctgcgctc  660
ccttgccagc ccgtggatat gtggacgatg gccgcgagcg gccaccggct ggctcgcttc  720
gctcggcccg tggacaaccc tgctggacaa gctgatggac aggctgcgcc tgcccacgag  780
cttgaccaca gggattgccc accggctacc cagccttcga ccacataccc accggctcca  840
actgcgcggc ctgcggcctt gccccatcaa ttttttttaat tttctctggg gaaaagcctc  900
cggcctgcgg cctgcgcgct tcgcttgccg gttggacacc aagtggaagg cgggtcaagg  960
ctcgcgcagc gaccgcgcag cggcttggcc ttgacgcgcc tggaacgacc caagcctatg  1020
cgagtggggg cagtcgaagg cgaagcccgc ccgcctgccc cccgagcctc acggcggcga  1080
gtgcgggggt tccaaggggg cagcgccacc ttgggcaagg ccgaaggccg cgcagtcgat  1140
caacaagccc cggaggggcc actttttgcc ggagggggag ccgcgccgaa ggcgtggggg  1200
aaccccgcag ggtgccctt ctttgggcac caaagaacta gatatagggc gaaatgcgaa  1260
agacttaaaa atcaacaact taaaaaaggg gggtacgcaa cagctcattg cggcaccccc  1320
cgcaatagct cattgcgtag gttaaagaaa atctgtaatt gactgccact tttacgcaac  1380
gcataattgt tgtcgcgctg ccgaaaagtt gcagctgatt gcgcatggtg ccgcaaccgt  1440
gcggcaccct accgcatgga gataagcatg gccacgcagt ccagagaaat cggcattcaa  1500
gccaagaaca agcccggtca ctgggtgcaa acggaacgca aagcgcatga ggcgtgggcc  1560
gggcttattg cgaggaaacc cacggcggca atgctgctgc atcacctcgt ggcgcagatg  1620
ggccaccaga acgccgtggt ggtcagccag aagacacttt ccaagctcat cggacgttct  1680
ttgcggacgg tccaatacgc agtcaaggac ttggtggccg agcgctggat ctccgtcgtg  1740
aagctcaacg gccccggcac cgtgtcggcc tacgtggtca atgaccgcgt ggcgtggggc  1800
cagccccgcg accagttgcg cctgtcggtg ttcagtgccg ccgtggtggt tgatcacgac  1860
gaccaggacg aatcgctgtt ggggcatggc gacctgcgcc gcatcccgac cctgtatccg  1920
ggcgagcagc aactaccgac cggccccggc gaggagccgc ccagccagcc cggcattccg  1980
ggcatggaac cagacctgcc agccttgacc gaaacggagg aatgggaacg gcgcgggcag  2040
cagcgcctgc cgatgcccga tgagccgtgt tttctggacg atggcgagcc gttggagccg  2100
ccgacacggg tcacgctgcc gcgccggtag cacttgggtt gcgcagcaac ccgtaagtgc  2160
gctgttccag actatcggct gtagccgcct cgccgcccta taccttgtct gcctccccgc  2220
gttgcgtcgc ggtgcatgga gccgggccac ctcgacctga atggaagccg gcggcacctc  2280
gctaacggat tcaccgtttt tatcaggctc tgggaggcag aataaatgat catatgagag  2340
cgttcaccga caaacaacag ataaaacgaa aggcccagtc tttcgactga gcctttcgtt  2400
ttatttgaag agctactctc gctcttcctc ctatgtgatc tttttgacgc ggtaatcaag  2460
ccgggctcga gttatcccaa gaagggaggc cgcccgggaa atattgccac cgctatgttt  2520
gacagctgct cgggtgatgg cgtcttgaac ctggtccagg ttaatagacc cttgatgcac  2580
catctgctcg gcaaactcat ctaatgagag aactttaggg ttggcgttct cagccgcgtt  2640
ccgtattagc tcgctgctca aggtcaaatc acctttctgg ttaagactca ggaagtcttg  2700
tgtagtgagg gtgccttcaa ttgtcgttaa atggtgggtg tccaaaaaat cgacgtcttg  2760
agccatgatt atggctctct caatcacgtt ctccaattct cgaatattgc ctggccagtc  2820
atggtagata agtacctgca tggcggcaga cgatatgcct tttaacttac gtccgtggcg  2880
tttagaaaat cgagcgatga gtacgctggt aatgagtgaa atatcatcgc ggcgttctcg  2940
cagaggggga atctggatgg gaaagacgtt cagtcgatag taaagatcct ctcggaagtg  3000
accatcttgg acagcttttt tcagatcagc gttcgtggcg gcaatcagtc ggacactggt  3060
gtggattgtc cggttgctac cgagacgttc caattcgcca ttctgcaata cacggagaag  3120
tttactttga gcggtcatac tgagggtggc aatttcgtca aggaagagag tgccttgatg  3180
```

```
agccgcctcg aaacgcccct ctcgcgtagc ggtcgcacct gtaaaggctc cgcgctctac  3240
gccgaacagc tccgactcga ttaattgatc gggtatagcg gcacagttca cttcgacgaa  3300
agcttggtcg gcgcggttgc tcaaacggtg gatctcgcgt gcaataaggc tcttgccgct  3360
cccactttct ccaagtaaaa gaacagtcgc atcagtctct gccacacagg ctgttttgtg  3420
acggagcacc ttgaacactg ccgacgaacc aatgacgagc tcgccgccct gatcatcatc  3480
gggaataggg tgcgtggtga tctgggattg ctccgactga ctgagcgccc acatttcggc  3540
gggcttcgct tgaatacggc aatgagtgtg tcccatcgct tggcattcga tctcttccac  3600
gacaatgggt tttccagcgc atgcgctcag gtaccctgag caatacgcaa cggaaaacca  3660
acataccgca tgtgaactga caccatgcat cgctaagtga atttcagctt cgatgctgtt  3720
ctgccagtat gcctccgcat gataatccat gctcttcata tcgaccgcat ttagcgccga  3780
tgatccagct tgtatagatg ttagaaaccc ttgcaaggcg tgcaagacac cacctgcata  3840
aatctgttct ttgatagagg atataccttg ttttttttata atcatttctg catcgcgttg  3900
gccggtggtg aagccgatac gagtcaaaaa ctcccgcgtg tagtctgggc cagaataggc  3960
ctgcaattcc ttgtatatat ccttcagtgt ctccacttgt aggagcaggc atcggctttc  4020
gtccagccag atacgtcctt cgttgggaga aaagtgcagc ttggaaacta aagcatggac  4080
ttcgggggagc gcaaggtcgg caacgatgga gcgatcgtcg ctattatttt tatttgattt  4140
catggcgatg gttcaggtcc ggtaggaata gatgagggtc tcgttgggtt taataatttt  4200
attaaattgt ggtggtggga ttcagaatat ggtgaaacca gctcgtccga gcaggcgcat  4260
tctggcatct gccgacggat ccatattccc ttcagtctta ctgtgtgtag gtgcatggat  4320
cgggctgtcg cctagccaga tgcgtccttc gttgtgggga gggaatgcag accgaacgcc  4380
gaaacatgga tttcagggcg cgatagatcg gcaacgatgg tgcggttttc atggttctta  4440
tttttgttag atttcatggt gatagctcat gccaggtagg agtagatagg gttctcgtag  4500
atttaataaa tttatgaaat cgtggttgtg agttttcata atatggtgaa gcttgcccgc  4560
catggcaagt gcatttcggc agctgttggc gaccgcggaa ggggtttaca gccgtctgga  4620
gctaggcttt ctggcgctca ttaaaataaa aatccttata aaacagtatc ctagctttta  4680
tgtctgaggc tgcttagtca acctggcacg gtactggcta cgagtcccgc aaggcagccg  4740
tgagttcgac tgtactgctg cctattaaaa caatatgaac gcggagacgt gataacaatg  4800
agtacaggca tcgataagga cgtccgagag tgttggggcg taactgcatt atcagcgggt  4860
catcaaattg caatgaatag cgcgtttctg gatatggact tgctgttgtg cggggaaacc  4920
ggcaccggca aggacacact ggccaaccgc attcacgagt tgtccagcag gtcgggaccc  4980
tttgtgggca tgaactgcgc cgccattccc gagtcgctgg cagagagcca gttattcggt  5040
gtggtcaacg gtgcattcac cggcgtatgc cgggctcgcg agggctacat agaggcctcc  5100
agtggtggca ccttgtacct ggatgaaatc gacagcatgc cgttgagcct gcaagccaaa  5160
ctgctgcgtg tgttggagag tcgaggtatc gagcgtctgg gctcgaccga atttatcccg  5220
gtggatctgc ggatcattgc ctcggcccag cggccactgg atgaactggt ggaacaagga  5280
cttttccgtc gcgacctgtt ttttcggctc aacgtgctga cgcttcactt gccagccttg  5340
cgcaaacgtc gtgaacagat cctgccattg ttcgaccagt tcacccaggg tatcgctgcc  5400
gagttcggac gtcccgctcc tgcgctggac agcgggcgtg tgcagctgct gctcagccac  5460
gactggccgg gcaacatccg cgaattgaag tctgcggcca agcgcttcgt actcggcttc  5520
cccttgctgg gcgccgaccc tgtggaagcg cttgaccctg ccacggggct gcgcacgcaa  5580
atgcgcatca tcgagaaaat gctcatccag gatgccttga agcggcacag gcacaatttc  5640
gacgcggtgc ttcaggagtt ggagttgcca agacgcaccc tgtatcaccg catgaaggaa  5700
ctgggagttg cagcgccgat cgctgcgacg gccggggtct aataaccagg catcaaagag  5760
gagaaaatga gtcttgatga aaggtttgag gatgatctgg acgaggagcg ggttccgaat  5820
ctggggatag ttgccgaaag tatttcgcaa ctgggtatcg acgtgctgct atcgggtgag  5880
accggcacgg gcaaagacac gattgcccga cggattcatg agatgtcagg ccgcaaaggg  5940
cgcctggtgg cgatgaattg cgcggccatt ccggagtccc tcgccgagag cgagttattc  6000
ggcgtggtca gcggtgccta caccggcgct gatcgctcca gagtcggtta tgtcgaagcg  6060
gcgcagggcg gcacgctgta cctggatgag atcgatagca tgccgctgag cctgcaagcc  6120
aaattgctga gggtgctgga aacccgagcg cttgaacggc tgggttcgac gtcgacgatc  6180
aagctggata tctgcgtgat cgcctccgcc caatgctcgc tggacgacgc cgtcgagcgg  6240
gggcagtttc gtcgcgatct gtattttcgc ctgaacgtcc tgacactcaa gcttcctccg  6300
ctacgtaacc agtctgatcg catagttccc ctgttcacac gttttacggc cgccgccgcg  6360
agggagctcg gtgttcccgt tcccgatgtt tgcccactgc tgcacaaagt gctgctgggc  6420
cacgactggc ccggcaatat ccgtgagctc aaggcggcag ccaaacgcca tgtgctgggt  6480
ttccccttgc tgggcgccga gccgcagggc gaagagcact tggcctgtgg gctcaaatcg  6540
caattgcgag tgatcgaaaa agccctgatt caggagtcgc tcaagcgcca cgacaattgt  6600
gtggattcgg taagcctgga actggacgtg ccacgccgta cgctctatcg acgcatcaaa  6660
gaattgcaga tctaatgctg ccaccgcaaa gaggagaaat actagatgac catgattacg  6720
ccaagcttgc atgcctgcag gtcgactcta gaggatcccc gggtaccgag ctcgaattca  6780
ctggccgtcg ttttacaacg tcgtgactgg gaaaaccctg gcgttaccca acttaatcgc  6840
cttgcagcac atcccccttt cgccagctgg cgtaatagcg aagaggcccg caccgatcgc  6900
ccttcccaac agttgcgcag cctgaatggc gaatggcgcc tgatgcggta ttttctcctt  6960
acgcatctgt gcggtatttc acaccgcata tggtgcactc tcagtacaat ctgctctgat  7020
gccgcataat aatactagag ccaggcatca aataaaacga aaggctcagt cgaaagactg  7080
ggcctttcgt tttatctgtt gtttgtcggt gaacgctctc tactagagtc acactggctc  7140
accttcgggt gggcctttct gcgtttatat actagtagcg gccgctgcag tccggcaaaa  7200
aagggcaagg tgtcaccacc ctgccctttt tctttaaaac cgaaaagatg ttaaaattcg  7260
cgttaaattt ttgttaaatc agctcatttt ttaaccaata ggccgactgc gatgagtggc  7320
agggcggggc gtaatttttt taaggcagtt attggtgccc ttaaacgcct ggtgctacgc  7380
ctgaataagt gataataagc ggatgaatgg cagaaattcg aaagcaaatt cgacccggtc  7440
gtcggttcag ggcagggtcg ttaaatagcc gcttatgtct attgctggtt taccggttta  7500
ttgactaccg gaagcagtgt gaccgtgtgc ttctcaaatg cctgaggcca gtttgctcag  7560
gctctccccg tggaggtaat aattgacgca gtcgataagc ccggatcagc ttgcaattcg  7620
cgcgcgaagg cgaagcggca tttacgttga caccatcgaa tggtgcaaaa cctttcgcgg  7680
tatggcatga tagcgcccgg aagagagtca attcagggtg gtgaatgtga aaccagtaac  7740
gttatacgat gtcgcagagt atgccggtgt ctcttatcag accgtttccc gcgtggtgaa  7800
ccaggccagc cacgtttctg cgaaaacgcg ggaaaaagtg gaagcggcga tggcggagct  7860
gaattacatt cccaaccgcg tggcacaaca actggcgggc aaacagtcgt tgctgattgg  7920
```

```
cgttgccacc tccagtctgg ccctgcacgc gccgtcgcaa attgtcgcgg cgattaaatc  7980
tcgcgccgat caactgggtg ccagcgtggt ggtgtcgatg gtagaacgaa gcggcgtcga  8040
agcctgtaaa gcggcggtgc acaatcttct cgcgcaacgc gtcagtgggc tgatcattaa  8100
ctatccgctg gatgaccagg atgccattgc tgtggaagct gcctgcacta atgttccggc  8160
gttatttctt gatgtctctg accagacacc catcaacagt attattttct cccatgaaga  8220
cggtacgcga ctgggcgtgg agcatctggt cgcattgggt caccagcaaa tcgcgctgtt  8280
agcgggccca ttaagttctg tctcggcgcg tctgcgtctg gctggctggc ataaatatct  8340
cactcgcaat caaattcagc cgatagcgga acgggaaggc gactggagtg ccatgtccgg  8400
ttttcaacaa accatgcaaa tgctgaatga gggcatcgtt cccactgcga tgctggttgc  8460
caacgatcag atggcgctgg gcgcaatgcg cgccattacc gagtccgggc tgcgcgttgg  8520
tgcggatatc tcggtagtgg gatacgacga taccgaagac agctcatgtt atatcccgcc  8580
gttaaccacc atcaaacagg attttcgcct gctggggcaa accagcgtgg accgcttgct  8640
gcaactctct cagggccagg cggtgaaggg caatcagctg ttgcccgtct cactggtgaa  8700
aagaaaaacc accctggcgc ccaatacgca aaccgcctct ccccgcgcgt tggccgattc  8760
attaatgcag ctggcacgac aggtttcccg actggaaagc gggcagtgag cgcaacgcaa  8820
ttaatgtaag ttagcgcgaa ttgcaagctg gccgacgcgc tgggctacgt cttgctgcgt  8880
tgcgctcact gcccgctttc cagtcgggaa acctgtcgtg ccagctgcat taatgaatcg  8940
gccaacgcgc ggggagaggc ggtttgcgta ttgggcgcat gcataaaaac tgttgtaatt  9000
cattaagcat tctgccgaca tggaagccat cacaaacggc atgatgaacc tgaatcgcca  9060
gcggcatcag caccttgtcg ccttgcgtat aatatttgcc cattcaaata tgtatccgct  9120
catgagacaa taaccctgat aaatgcttca ataatattga aaaaggaaga gtatgagtat  9180
tcaacatttc cgtgtcgccc ttattccctt ttttgcggca ttttgccttc ctgtttttgc  9240
tcacccagaa acgctggtga aagtaaaaga tgctgaagat cagttgggtg cacgagtggg  9300
ttacatcgaa ctggatctca acagcggtaa gatccttgag agttttcgcc ccgaagaacg  9360
ttttccaatg atgagcactt ttaaagttct gctatgtggc gcggtattat cccgtattga  9420
cgccgggcaa gagcaactcg gtcgccgcat acactattct cagaatgact tggttgagta  9480
ctcaccagtc acagaaaagc atcttacgga tggcatgaca gtaagagaat tatgcagtgc  9540
tgccataacc atgagtgata acactgcggc caacttactt ctgacaacga tcggaggacc  9600
gaaggagcta accgcttttt tgcacaacat gggggatcat gtaactcgcc ttgatcgttg  9660
ggaaccggag ctgaatgaag ccataccaaa cgacgagcgt gacaccacga tgcctgtagc  9720
aatggcaaca acgttgcgca aactattaac tggcgaacta cttactctag cttcccggca  9780
acaattaata gactggatgg aggcggataa agttgcagga ccacttctgc gctcggccct  9840
tccggctggc tggtttattg ctgataaatc tggagccggt gagcgtgggt cacgcggtat  9900
cattgcagca ctggggccag atggtaagcc ctcccgtatc gtagttatct acacgacggg  9960
gagtcaggca actatggatg aacgaaatag acagatcgct gagataggtg cctcactgat  10020
taagcattgg taactgtcag accaagttta ctcatatata ctttagattg atttaaaact  10080
tcatttttaa tttaaaagga tctaggtgaa gatccttttt gataatctca tgaccaaaat  10140
ccaggtggca cttttcgggg aaatgtgcgc gcccgcgttc ctgctggcgc tgggcctgtt  10200
tctggcgctg gacttcccgc tgttccgtca gcagcttttc gcccacggcc ttgatgatcg  10260
cggcggcctt ggcctgcata tcccgattca acggccccag ggcgtccaga acgggcttca  10320
ggcgctcccg aaggtctcgg gccgtctctt gggcttgatc ggccttcttg cgcatctcac  10380
gcgctcctgc ggcggcctgt agggcaggct catacccctg ccgaaccgct tttgtcagcc  10440
ggtcggccac ggcttccggc gtctcaacgc gctttgagat tcccagcttt tcggccaatc  10500
cctgcggtgc ataggcgcgt ggctcgaccg cttgcgggct gatggtgacg tggcccactg  10560
gtggccgctc cagggcctcg tagaacgcct gaatgcgcgt gtgacgtgcc ttgctgccct  10620
cgatgccccg ttgcagccct agatcggcca cagcggccgc                        10660
```

```
SEQ ID NO: 15          moltype = DNA  length = 10495
FEATURE                Location/Qualifiers
source                 1..10495
                       mol_type = other DNA
                       note = pBL_IMP_33 (lacZ ampli end)
                       organism = synthetic construct
SEQUENCE: 15
caaaagcaac agcgaggcag catggcgatt tatcacctta cggcgaaaac cggcagcagg  60
tcgggcggcc aatcggccag ggccaaggcc gactacatcc agcgcgaagg caagtatgcc  120
cgcgacatgg atgaagtctt gcacgccgaa tccgggcaca tgccggagtt cgtcgagcgg  180
cccgccgact actgggatgc tgccgacctg tatgaacgcg ccaatgggcg gctgttcaag  240
gaggtcgaat ttgccctgcc ggtcgagctg accctcgacc agcagaaggc gctggcgtcc  300
gagttcgccc agcacctgac cggtgccgag cgcctgccgt atacgctggc catccatgcc  360
ggtggcggcg agaacccgca ctgccacctg atgatctccg agcggatcaa tgacggcatc  420
gagcggcccg ccgctcagtg gttcaagcgg tacaacggca agaccccgga gaagggcggg  480
gcacagaaga ccgaagcgct caagcccaag gcatggcttg agcagacccg cgaggcatgg  540
gccgaccatg ccaaccgggc attagagcgg gctggccacg acgcccgcat tgaccacaga  600
acacttgagg cgcagggcat cgagcgcctg cccggtgttc acctggggcc gaacgtggtg  660
gagatggaag gccggggcat ccgcaccgac cgggcagacg tggccctgaa catcgacacc  720
gccaacgccc agatcatcga cttacaggaa taccgggagg caatagacca tgaacgcaat  780
cgacagagtg aagaaatcca gaggcatcaa cgagttagcg gagcagatcg aaccgctggc  840
ccagagcatg gcgacactgg ccgacgaagc ccggcaggtc atgagccaga ccaagcaggc  900
cagcgaggcg caggcggcgg agtggctgaa agcccagcgc cagacagggg cggcatgggt  960
ggagctggcc aaagagttgc gggaggtagc cgccgaggtg agcagcgccg cgcagagcgc  1020
ccggagcgcg tcgcgggggt ggcactggaa gctatggcta accgtgatgc tggcttccat  1080
gatgcctacg gtggtgctgc tgatcgcatc gttgctcttg ctcgacctga cgccactgac  1140
aaccgaggac ggctcgatct ggctgcgctt ggtggcccga tgaagaacga caggactttg  1200
caggccatag gccgacagct caaggccatg ggctgtgagc gcttcgatat cggcgtcagg  1260
gacgcaccca ccggccagat gatgaaccgg gaatggtcag ccgccgaagt gctccagaac  1320
acgccatggc tcaagcggat gaatgcccag ggcaatgacg tgtatatcag gcccgccgag  1380
caggagcggc atggtctggt gctggtggac gacctcagcg agtttgacct ggatgacatg  1440
aaagccgagg gccgggagcc tgccctggta gtggaaacca gcccgaagaa ctatcaggca  1500
```

```
tgggtcaagg tggccgacgc cgcaggcggt gaacttcggg ggcagattgc ccggacgctg  1560
gccagcgagt acgacgccga cccggccagc gccgacagcc gccactatgg ccgcttggcg  1620
ggcttcacca accgcaagga caagcacacc acccgcgccg gttatcagcc gtgggtgctg  1680
ctgcgtgaat ccaagggcaa gaccgccacc gctggcccgg cgctggtgca gcaggctggc  1740
cagcagatcg agcaggccca gcggcagcag gagaaggccc gcaggctggc cagcctcgaa  1800
ctgcccgagc ggcagcttag ccgccaccgg cgcacggcgc tggacgagta ccgcagcgag  1860
atggccgggc tggtcaagcg cttcggtcat gacctcagca agtgcgactt tatcgccgcg  1920
cagaagctgg ccagccgggg ccgcagtgcc gaggaaatcg gcaaggccat ggccgaggcc  1980
agcccagcgc tggcagagcg caagcccggc cacgaagcgg attacatcga gcgcaccgtc  2040
agcaaggtca tgggtctgcc cagcgtccag cttgcgcggg ccgagctggc acgggcaccg  2100
gcaccccgcc agcgaggcat ggacagggc gggccagatt tcagcatgta gtgcttgcgt  2160
tggtactcac gcctgttata ctatgagtac tcacgcacag aagggggttt tatggaatac  2220
gaaaaaagcg cttcagggtc ggtctacctg atcaaaagtg acaagggcta ttggttgccc  2280
ggtggctttg gttatacgtc aaacaaggcc gaggctggcc gcttttcagt cgctgatatg  2340
gccagcctta accttgacgg ctgcaccttg tccttgttcc gcgaagacaa gcctttcggc  2400
cccggcaagt ttctcggtga ctgatatgaa agaccaaaag gacaagcaga ccggcgacct  2460
gctggccagc cctgacgctg tacgccaagc gcgatatgcc gagcgcatga aggccaaagg  2520
gatgcgtcag cgcaagttct ggctgaccga cgacgaatac gaggcgctgc gcgagtgcct  2580
ggaagaactc agagcggcgc agggcggggg tagtgacccc gccagcgcct aaccaccaac  2640
tgcctgcaaa ggaggcaatc aatggctacc cataagccta tcaatattct ggaggcgttc  2700
gcagcagcgc cgccaccgct ggactacgtt ttgcccaaca tggtggccgg tacggtcggg  2760
gcgctggtgt cgcccggtgg tgccggtaaa tccatgctgg ccctgcaact ggccgcacag  2820
attgcaggcg ggccggatct gctggaggtg ggcgaactgc ccaccggccc ggtgatctac  2880
ctgcccgccg aagacccgcc caccgccatt catcaccgcc tgcacgccct tggggcgcac  2940
ctcagcgccg aggaacggca agccgtggct gacggcctgc tgatccagcc gctgatcggc  3000
agcctgccca acatcatggc cccggagtgg ttcgacggcc tcaagcgcgc cgccgagggc  3060
cgccgcctga tggtgctgga cacgctgcgc cggttccaca tcgaggaaga aaacgccagc  3120
ggccccatgg cccaggtcat cggtcgcatg gaggccatcg ccgccgatac cgggtgctct  3180
atcgtgttcc tgcaccatgc cagcaagggc gcggccatga tgggcgcagg cgaccagcag  3240
caggccagcc ggggcagctc ggtactggtc gataacatcc gctggcagtc ctacctgtcg  3300
agcatgacca gcgccgaggc cgaggaatgg ggtgtggacg acgaccagcg ccggttcttc  3360
gtccgcttcg gtgtgagcaa ggccaactat ggcgcaccgt tcgctgatcg gtggttcagg  3420
cggcatgacg gcggggtgct caagcccgcc gtgctggaga ggcagcgcaa gagcaagggg  3480
gtgccccgtg gtgaagccta agaacaagca cagcctcagc cacgtccggc acgacccggc  3540
gcactgtctg gcccccggcc tgttccgtgc cctcaagcgg ggcgagcgca agcgcagcaa  3600
gctggacgtg acgtatgact acggcgacgg caagcggatc gagttcagcg gcccggagcc  3660
gctgggcgct gatgatctgc gcatcctgca agggctggtg gccatggctg ggcctaatgg  3720
cctagtgctt ggcccggaac ccaagaccga aggcggacgg cagctccggc tgttcctgga  3780
acccaagtgg gaggccgtca ccgctgaatg ccatgtggtc aaaggtagct atcgggcgct  3840
ggcaaaggaa atcggggcag aggtcgatag tggtggggcg ctcaagcaca tacaggactg  3900
catcgagcgc ctttggaagg tatccatcat cgcccagaat ggccgcaagc ggcaggggtt  3960
tcggctgctg tcggagtacg ccagcgacga ggcggacggg cgcctgtacg tggccctgaa  4020
ccccttgatc gcgcaggccg tcatgggtgg cggccagcat gtgcgcatca gcatggacga  4080
ggtgcgggcg ctggacagcg aaaccgcccg cctgctgcac cagcggctgt gtggctggat  4140
cgaccccggc aaaaccggca aggcttccat agataccttg tgcggctatg tctggccgtc  4200
agaggccagt ggttcgacca tgcgcaagcg ccgcaagcgg gtgcgcgagg cgttgccgga  4260
gctggtcgcg ctgggctgga cggtaaccga gttcgcggcg ggcaagtacg acatcacccg  4320
gcccaaggcg gcaggctgac cccccccact ctattgtaaa caagacattt ttatctttta  4380
tattcaatgg cttattttcc tgctaattgg taataccatg aaaaatacca tgctcagaaa  4440
aggcttaaca atattttgaa aaattgccta ctgagcgctg ccgcacagct ccataggccg  4500
ctttcctggc tttgcttcca gatgtatgct cttctgctcc cgaacgccag caagacgtag  4560
cccagcgcgt cggccagctt gcaattcgcg ctaacttaca ttaattgcgt tgcgcgccgg  4620
attatgtccg ctgagtgggt cacggtcccg gatcagttcc cttgcgaagc tgaccgatgt  4680
ttttgtgcca aaagctgttg tggcaaaaaa cggtttgcgc aaagttttgt attacaaaga  4740
atttcacatt ttaaaatatc tttataaatc aatcagttat ttctattttt aagctggcat  4800
ggttatcgct atagggcttg tactactaga gattaaagag gagaaatact agatgagtac  4860
aggcatcgat aaggacgtcc gagagtgttg gggcgtaact gcattatcag cgggtcatca  4920
aattgcaatg aatagcgcgt ttctggatat ggacttgctg ttgtgcgggg aaaccggcac  4980
cggcaaggac acactggcca accgcattca cgagttgtcc agcaggtcgg gaccctttgt  5040
gggcatgaac tgcgccgcca ttcccgagtc gctggcagag agccagttat tcggtgtggt  5100
caacggtgca ttcaccggcg tatgccgggc tcgcgagggc tacatagagg cctccagtgg  5160
tggcaccttg tacctggatg aaatcgacag catgccgttg agcctgcaag ccaaactgct  5220
gcgtgtgttg gagagtcgag gtatcgagcg tctgggctcg accgaattta tcccggtgga  5280
tctgcggatc attgcctcgg cccagcggcc actggatgaa ctggtggaac aaggactttt  5340
ccgtcgcgac ctgtttttc ggctcaacgt gctgacgctt cacttgccag ccttgcgcaa  5400
acgtcgtgaa cagatcctgc cattgttcga ccagttcacc cagggtatcg ctgccgagtt  5460
cggacgtccc gctcctgcgc tggacagcgg gcgtgtgcag ctgctgctca gccacgactg  5520
gccgggcaac atccgcgaat tgaagtctgc ggccaagcgc ttcgtactcg gcttcccctt  5580
gctgggcgcc gaccctgtgg aagcgcttga ccctgccacg gggctgcgca cgcaaatgcg  5640
catcatcgag aaaatgctca tccaggatgc cttgaagcgg cacaggcaca atttcgacgc  5700
ggtgcttcag gagttggagt tgccaagacg caccctgtat caccgcatga aggaactggg  5760
agttgcagcg ccgatcgctg cgacggccgg ggtctaataa ccaggcatca aagaggagaa  5820
aatgagtctt gatgaaaggt ttgaggatga tctggacgag gagcgggttc cgaatctggg  5880
gatagttgcc gaaagtattt cgcaactggg tatcgacgtg ctgctatcgg gtgagaccgg  5940
cacgggcaaa gacacgattg cccgacggat tcatgagatg tcaggccgca aagggcgcct  6000
ggtggcgatg aattgcgcgg ccattccgga gtccctcgcc gagagcgagt tattcggcgt  6060
ggtcagcggt gcctacaccg gcgctgatcg ctccagagtc ggttatgtcg aagcggcgca  6120
gggcggcacg ctgtacctgg atgagatcga tagcatgccg ctgagcctgc aagccaaatt  6180
gctgagggtg ctggaaaccc gagcgcttga acggctgggt tcgacgtcga cgatcaagct  6240
```

-continued

```
ggatatctgc gtgatcgcct ccgcccaatg ctcgctggac gacgccgtcg agcgggggca  6300
gtttcgtcgc gatctgtatt ttcgcctgaa cgtcctgaca ctcaagcttc ctccgctacg  6360
taaccagtct gatcgcatag ttcccctgtt cacacgtttt acggccgccg ccgcgaggga  6420
gctcggtgtt cccgttcccg atgtttgccc actgctgcac aaagtgctgc tgggccacga  6480
ctggcccggc aatatccgtg agctcaaggc ggcagccaaa cgccatgtgc tgggtttccc  6540
cttgctgggc gccgagccgc agggcgaaga gcacttggcc tgtgggctca aatcgcaatt  6600
gcgagtgatc gaaaaagccc tgattcagga gtcgctcaag cgccacgaca attgtgtgga  6660
ttcggtaagc ctggaactgg acgtgccacg ccgtacgctc tatcgacgca tcaaagaatt  6720
gcagatctaa tgctgccacc gcaaagagga gaaatactag atgaccatga ttacgccaag  6780
cttgcatgcc tgcaggtcga ctctagagga tccccgggta ccgagctcga attcactggc  6840
cgtcgtttta caacgtcgtg actgggaaaa ccctggcgtt acccaactta atcgccttgc  6900
agcacatccc cctttcgcca gctggcgtaa tagcgaagag gcccgcaccg atcgcccttc  6960
ccaacagttg cgcagcctga atggcgaatg gcgcctgatg cggtattttc tccttacgca  7020
tctgtgcggt atttcacacc gcatatggtg cactctcagt acaatctgct ctgatgccgc  7080
ataataatac tagagccagg catcaaataa aacgaaaggc tcagtcgaaa gactgggcct  7140
ttcgttttat ctgttgtttg tcggtgaacg ctctctacta gagtcacact ggctcacctt  7200
cgggtgggcc tttctgcgtt tatatactag tagcggccgc tgcagtccgg caaaaaaggg  7260
caaggtgtca ccaccctgcc ctttttcttt aaaaccgaaa agaatgtgga caaattcttc  7320
caactgatcc gcgagcttca cgctgccgca agcactcagg gcgcaagggc tgctaaagga  7380
agcggaacac gtagaaagcc agtccgcaga aacggtgctg accccggatg aatgtcagct  7440
actgggctat ctggacaagg gaaaacgcaa gcgcaaagag aaagcaggta gcttgcagtg  7500
ggcttacatg gcgatagcta gactgggcgg ttttatggac agcaagcgaa ccggaattgc  7560
cagctggggc gccctctggt aaggttggga agccctgcaa agtaaactgg atggctttct  7620
tgccgccaag gatctgatgg cgcaggggat caagatctga tcaagagaca ggatgaggat  7680
cgtttcgcat gattgaacaa gatggattgc acgcaggttc tccggccgct tgggtggaga  7740
ggctattcgg ctatgactgg gcacaacaga caatcggctg ctctgatgcc gccgtgttcc  7800
ggctgtcagc gcaggggcgc ccggttcttt ttgtcaagac cgacctgtcc ggtgccctga  7860
atgaactgca ggacgaggca gcgcggctat cgtggctggc cacgacgggc gttccttgcg  7920
cagctgtgct cgacgttgtc actgaagcgg gaagggactg gctgctattg ggcgaagtgc  7980
cggggcagga tctcctgtca tctcaccttg ctcctgccga gaaagtatcc atcatggctg  8040
atgcaatgcg gcggctgcat acgcttgatc cggctacctg cccattcgac caccaagcga  8100
aacatcgcat cgagcgagca cgtactcgga tggaagccgg tcttgtcgat caggatgatc  8160
tggacgaaga gcatcagggg ctcgcgccag ccgaactgtt cgccaggctc aaggcgcgca  8220
tgcccgacgg cgaggatctc gtcgtgaccc atggcgatgc ctgcttgccg aatatcatgg  8280
tggaaaatgg ccgcttttct ggattcatcg actgtggccg gctgggtgtg gcggaccgct  8340
atcaggacat agcgttggct acccgtgata ttgctgaaga gcttggcggc gaatgggctg  8400
accgcttcct cgtgctttac ggtatcgccg ctcccgattc gcagcgcatc gccttctatc  8460
gccttcttga cgagttcttc tgagcgggac tctggggttc gaaatgaccg accaagcgac  8520
gcccaacctg ccatcacgag atttcgattc caccgccgcc ttctatgaaa ggttgggctt  8580
cggaatcgtt ttccgggacg ccggctggat gatcctccag cgcggggatc tcatgctgga  8640
gttcttcgcc caccccgggc tcgatcccct cgcgagttgg ttcagctgct gcctgaggct  8700
ggacgacctc gcggagttct accggcagtg caaatccgtc ggcatccagg aaaccagcag  8760
cggctatccg cgcatccatg cccccgaact gcaggagtgg ggaggcacga tggccgcttt  8820
ggtcgacgga tcagtgaggg tttgcaactg cgggtcaagg atctggattt cgatcacggc  8880
acgatcatcg tgcgggaggg caagggctcc aaggatcggg ccttgatgtt acccgagagc  8940
ttggcaccca gcctgcgcga gcaggggaat tgatccggtg gatgaccttt tgaatgacct  9000
ttaatagatt atattactaa ttaattgggg accctagagg tcccctttttt tattttaaaa  9060
atttttcac aaaacggttt acaagcataa agctaaacgt ggccaatatg gacaacttct  9120
tcgcccccgt tttcaccatg ggcaaatatt atacgcaagg cgacaaggtg ctgatgccgc  9180
tggcgattca ggttcatcat gccgtttgtg atggcttcca tgtcggcaga atgcttaatg  9240
aattacaaca gtactgcgat gagtggcagg gcggggcgta atttttttaa ggcagttatt  9300
gtcttcaaat tcccgttgca catagcccgg caattccttt ccctgctctg ccataagcgc  9360
agcgaatgcc gggtaatact cgtcaacgat ctgatagaga agggtttgct cgggtcggtg  9420
gctctggtaa cgaccagtat cccgatcccg gctggccgtc ctggccgcca catgaggcat  9480
gttccgcgtc cttgcaatac tgtgtttaca tacagtctat cgcttagcgg aaagttcttt  9540
taccctcagc cgaaatgcct gccgttgcta gacattgcca gccagtgccc gtcactcccg  9600
tactaactgt cacgaacccc tgcaataact gtcacgcccc cctgcaataa ctgtcacgaa  9660
cccctgcaat aactgtcacg cccccaaacc tgcaaaccca gcaggggcgg gggctggcgg  9720
ggtgttggaa aaatccatcc atgattatct aagaataatc cactaggcgc ggttatcagc  9780
gcccttgtgg ggcgctgctg cccttgccca atatgcccgg ccagaggccg gatagctggt  9840
ctattcgctg cgctaggcta cacaccgccc caccgctgcg cggcaggggg aaaggcgggc  9900
aaagcccgct aaaccccaca ccaaaccccg cagaaatacg ctggagcgct tttagccgct  9960
ttagcggcct ttcccctac ccgaagggtg gggcgcgtg tgcagccccg cagggcctgt  10020
ctcggtcgat cattcagccc ggctcatcct tctggcgtgg cggcagaccg aacaaggcgc  10080
ggtcgtggtc gcgttcaagg tacgcatcca ttgccgccat gagccgatcc tccggccact  10140
cgctgctgtt caccttggcc aaaatcatgg cccccaccag caccttgcgc cttgtttcgt  10200
tcttgcgctc ttgctgctgt tcccttgccc gctcccgctg aatttcggca ttgattcgcg  10260
ctcgttgttc ttcgagcttg gccagccgat ccgccgcctt gttgctcccc ttaaccatct  10320
tgacacccca ttgttaatgt gctgtctcgt aggctatcat ggaggcacag cggcggcaat  10380
cccgacccta ctttgtaggg gagggcgcac ttaccggttt ctcttcgaga aactggccta  10440
acggccaccc ttcgggcggt gcgctctccg agggccattg catggagccg aaaag       10495
```